United States Patent
Ruijssenaars

(10) Patent No.: US 10,457,965 B2
(45) Date of Patent: Oct. 29, 2019

(54) DEHYDROGENASE-CATALYSED PRODUCTION OF FDCA

(71) Applicant: Purac Biochem B.V., Gorinchem (NL)

(72) Inventor: Harald Johan Ruijssenaars, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 15/550,438

(22) PCT Filed: Feb. 17, 2016

(86) PCT No.: PCT/NL2016/050108
§ 371 (c)(1),
(2) Date: Aug. 11, 2017

(87) PCT Pub. No.: WO2016/133384
PCT Pub. Date: Aug. 25, 2016

(65) Prior Publication Data
US 2018/0030488 A1 Feb. 1, 2018

(30) Foreign Application Priority Data

Feb. 17, 2015 (EP) ................................. 15155401

(51) Int. Cl.
| | | |
|---|---|---|
| C12N 1/20 | (2006.01) |
| C12P 17/04 | (2006.01) |
| C12N 9/06 | (2006.01) |
| C08G 63/181 | (2006.01) |
| C12N 9/02 | (2006.01) |

(52) U.S. Cl.
CPC ............ *C12P 17/04* (2013.01); *C08G 63/181* (2013.01); *C12N 9/0008* (2013.01); *C12N 9/0016* (2013.01); *C12Y 102/00* (2013.01)

(58) Field of Classification Search
CPC ... C12N 9/0002; C12N 9/0016; C12Y 102/00
USPC .................... 435/190, 252.3, 320.1
See application file for complete search history.

(56) References Cited

U.S. PATENT DOCUMENTS

2018/0265896 A1* 9/2018 de Bont ............... C12N 9/0006

FOREIGN PATENT DOCUMENTS

| WO | WO-2011/026913 A1 | 3/2011 |
| WO | WO-2012/064195 A2 | 5/2012 |

OTHER PUBLICATIONS

Database Geneseq [Online], "2-hydroxytetraocosenoic acid production-related gene, SEQ:39759", XP002738394, retrieved from EBI accession No. GSN:AXE21543, Oct. 14, 2010.
Database UniProt[Online], "SubName: Full=Alcohol dehydrogenase {ECO:0000313 | EMBL:AEG14239.1}; EC=1.1.1.1 {ECO:0000313 | EMBL:AEG14239};", XP002738395, retrieved from EBI accession No. UniProt:F6CQG2, Jul. 27, 2011.
Database UniProt[Online], "SubName: Full=Alcohol dehydrogenase {ECO:0000313 { EMBL:BAF58676.1};", XP002738397, retrieved from EBI accession No. UniProt:A5D4Z8, Jun. 12, 2007.
Database UniProt[Online], "SubName: Full=Alcohol dehydrogenase {ECO:0000313 { EMBL:EST53419.1}; Vihsleekgl HFQIYADVEP DPSLETIQAG AAMFQQQSFD CMVAIGGGSP IDTAKGIRVL", XP002738396, retrieved from EBI accession No. UniProt:V6M4A5, Feb. 19, 2014.
International Search Report issued in International Patent Application No. PCT/NL2016/050108, dated Aug. 8, 2016.

* cited by examiner

*Primary Examiner* — Tekchand Saidha
(74) *Attorney, Agent, or Firm* — Gilberto M. Villacorta; SUnit Talapatra; Foley & Lardner LLP

(57) ABSTRACT

The invention relates to a cell expressing a polypeptide having 5-hydroxymethyl-2-furancarboxylic acid dehydrogenase activity, as well as to a cell expressing a polypeptide having furanic compound transport capabilities. The invention also relates to a process for the production of 2,5-furandicarboxylic acid (FDCA) wherein the cells of the invention are used for oxidation of a furanic precursors of FDCA.

21 Claims, 4 Drawing Sheets

Specification includes a Sequence Listing.

DEHYDROGENASE-CATALYSED PRODUCTION OF FDCA

CROSS-REFERENCE TO RELATED APPLICATIONS

This application is the National Phase of International Patent Application No. PCT/NL2016/050108, filed Feb. 17, 2016, published on Aug. 25, 2016 as WO 2016/133384 A1, which claims priority to European Patent Application No. 15155401.1, filed Feb. 17, 2015. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Aug. 8, 2017, is named 069818-3020_SequenceListing.txt and is 108 KB.

FIELD OF THE INVENTION

The invention relates to the fields of enzymology, molecular genetics, biotransformation and fermentation technology. In particular, the invention relates to dehydrogenases that oxidize 5-(hydroxymethyl)-2-furoic acid into 5-formyl-2-furoic acid, and to polynucleotides encoding such dehydrogenases and their use in the biotransformation of hydroxymethylfurfural into 2,5-furandicarboxylic acid.

BACKGROUND OF THE INVENTION 2,5-furandicarboxylic acid (FDCA) is a monomeric compound which can be applied in the production of polyesters which have a tremendous economic impact. A very important compound in the field is polyethyleneterephthalate (PET) which is produced from terephthalic acid (PTA) and ethylene glycol. FDCA may substitute for PTA in the polyester PET in which case polyethylenefurandicarboxylate (PEF) results. PEF has a good potential in replacing PET in the large polyester market. Not only because it has superior properties when compared to PET, but also because it can be derived from renewable feedstocks. FDCA can be produced from sugars either chemically (De Jong et al 2012. In: Biobased Monomers, Polymers, and Materials; Smith, P., et al.; ACS Symposium Series; American Chemical Society: Washington, D.C.) or in a combined chemical-biological route (Wiercks et al 2011. Appl Microbiol Biotechnol 92:1095-1105). In the latter case, a monomeric sugar such as glucose or fructose is chemically transformed into 5-(hydroxymethyl)-2-furaldehyde (HMF) which subsequently can be oxidized by enzymes into FDCA.

A biological route for producing FDCA from HMF has been developed based on the isolation of the HMF-degrading strain of *Cupriavidus basilensis* HMF14 (Wierckx et al 2010. Microbial Technology 3:336-343). A cluster of genes encoding enzymes involved in the HMF degradation route in *C. basilensis* HMF14 was identified and relevant genes were heterologously expressed in a *Pseudomonas putida* strain (Koopman et al 2010. PNAS 107:4919-4924) which thereby acquired the ability to metabolize HMF. The first oxidative step in the degradation route involved the formation of 5-(hydroxymethyl)-2-furoic acid (HMFCA) which in turn was oxidized into 5-formyl-2-furoic acid (FFA) and further into FDCA. In subsequent work (Koopman et al 2010. Bioresource Technology 101:6291-6296; and WO 2011/026913), only the hmfH gene of *C. basilensis* HMF14 that encodes the enzyme HMF oxidoreductase was introduced into *P. putida*. The oxidoreductase acts as an oxidase mainly at HMFCA, but it also may oxidize HMF or FFA. The heterologous expression of only the hmfH gene enables *P. putida* to produce FDCA from HMF. In further optimization work (Wierckx et al 2011, supra; and WO 2012/064195), two additional genes were expressed in *P. putida* that encode for an HMFCA transporter and for an aldehyde dehydrogenase with unknown specificity, respectively.

However, the oxidase-catalysed route for the production of FDCA from HMF has several inherent disadvantages as compared to a dehydrogenase-catalysed route, which include at least the production of toxic $H_2O_2$, the lack of energy gain from the oxidative step and the poor affinity for $O_2$ and associated high oxygen demand of the system. It is therefore an object of the present invention to address these disadvantages by providing means and methods for a novel dehydrogenase-catalysed route for the production of FDCA from furanic precursors such as HMF, as well as providing means and methods for using a novel HMFCA transporter in such processes.

SUMMARY OF THE INVENTION

In a first aspect the invention pertains to a cell comprising an expression construct for expression of a nucleotide sequence encoding an dehydrogenase having an amino acid sequence with at least 45% identity with any one of the amino acid sequence of SEQ ID NO: 1 to 11, wherein, the expression construct is expressible in the cell and expression of the dehydrogenase confers to or increases in the cell the ability to oxidize 5-hydroxymethyl-2-furancarboxylic acid (HMFCA) to 5-formyl-2-furoic acid (FFA), as compared to a corresponding wild type cell lacking the expression construct. Preferably, the cell further has: a) an aldehyde dehydrogenase activity that oxidizes furanic aldehydes to the corresponding furanic carboxylic acids, wherein preferably the cell comprises a second expression construct for expression of a nucleotide sequence encoding an aldehyde dehydrogenase comprising an amino acid sequence with at least 45% identity with any one of the amino acid sequence SEQ ID NO's: 24, 25, 26, 27, 28, 29 and 30, wherein, the second expression construct is expressible in the cell and expression of the aldehyde dehydrogenase confers to or increases in the cell at least one of the abilities of i) oxidizing 5-hydroxymethylfurfural (HMF) to HMFCA, ii) oxidizing DFF to FFA, and iii) oxidizing FFA into FDCA, as compared to a corresponding wild type cell lacking the second expression construct; and, b) the ability of transporting furanic compounds into and/or out of the cell, wherein preferably, the cell comprises a third expression construct for expression of a nucleotide sequence encoding a polypeptide having the ability to transport at least HMFCA into the cell, which polypeptide comprises an amino acid sequence with at least 45% identity with any one of the amino acid sequence SEQ ID NO's: 17, 31, 32, 33 and 34, wherein, the third expression construct is expressible in the cell and expression of the polypeptide confers to or increases in the cell the ability to transport at least HMFCA into the cell, as compared to a corresponding wild type cell lacking the third expression construct.

In another aspect, the invention pertains to a cell comprising an expression construct for expression of a nucleotide sequence encoding a polypeptide having the ability to transport at least HMFCA into the cell, the polypeptide comprising an amino acid sequence with at least 86.5% identity with the amino acid sequence of SEQ ID NO: 17, wherein, the expression construct is expressible in the cell and expression of the polypeptide confers to or increases in the cell the at least ability to transport at least HMFCA into the cell, as compared to a corresponding wild type cell lacking the expression construct, and wherein the cell further comprises enzymes for converting HMF into FDCA, wherein the enzymes for converting HMF into FDCA preferably include at least one of: a) alcohol dehydrogenase that oxidizes HMFCA to FFA and an aldehyde dehydrogenase activity that oxidizes furanic aldehydes to the corresponding furanic carboxylic acids; and, b) an oxidoreductase that oxidizes one or more of HMF, 2,5-dihydroxymethyl furan, HMFCA, FFA and 2,5-diformyl furan to FDCA and optionally an aldehyde dehydrogenase activity that oxidizes furanic aldehydes to the corresponding furanic carboxylic acids.

A cell according to the invention preferably is a microbial cell, such as a bacterial, yeast or filamentous fungal cell. A yeast or filamentous fungal cell of the invention preferably is selected from a genus from the group consisting of *Candida, Hansenula, Kluyveromyces, Pichia, Saccharomyces, Schizosaccharomyces, Yarrowia, Acremonium, Agaricus, Aspergillus, Aureobasidium, Myceliophthora, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium,* and *Trichoderma*, most preferably a yeast or filamentous fungal cell selected from a species from the group consisting of from *Kluyveromyces lactis, S. cerevisiae, Hansenula polymorpha, Yarrowia lipolytica, Pichia pastoris, Aspergillus niger, Aspergillus awamori, Aspergillus foetidus, Aspergillus sojae, Aspergillus fumigatus, Talaromyces emersonii, Aspergillus oryzae, Myceliophthora thermophila, Trichoderma reesei* and *Penicillium chrysogenum*. A bacterial cell of the invention preferably is selected from a genus from the group consisting of *Escherichia, Anabaena, Aeribacillus, Aneurinibacillus, Burkholderia, Bradyrhizobium, Caulobacter, Cupriavidus, Desulfotomaculum, Desulfurispora, Gluconobacter, Rhodobacter, Pelotomaculum, Pseudomonas, Paracoccus, Bacillus, Geobacillus, Brevibacillus, Brevibacterium, Corynebacterium, Rhizobium (Sinorhizobium), Flavobacterium, Klebsiella, Enterobacter, Lactobacillus, Lactococcus, Methylobacterium, Ralstonia, Rhodopseudomonas, Staphylococcus* and *Streptomyces*, more preferably a bacterial cell selected from a species from the group consisting of *A. pallidus, A. terranovensis, B. subtilis, B. amyloliquefaciens, B. coagulans, B. kribbensis, B. licheniformis, B. puntis, B. megaterium, B. halodurans, B. pumilus, B. thermoruber, B. panacihumi, C. basilensis, D. kuznetsovii, D. thermophila, G. kaustophilus, Gluconobacter oxydans, Caulobacter crescentus CB 15, Methylobacterium extorquens, Rhodobacter sphaeroides, Pelotomaculum thermopropionicum, Pseudomonas zeaxanthinifaciens, Pseudomonas putida, Paracoccus denitrificans, E. coli, C. glutamicum, Staphylococcus carnosus, Streptomyces lividans, Sinorhizobium melioti* and *Rhizobium radiobacter.*

In a further aspect, the invention relates to a process for preparing a polypeptide having a HMFCA dehydrogenase activity as defined in the above aspects, and/or for preparing a polypeptide having furanic compound transport capabilities as defined in the above aspects. The method preferably comprising the step of cultivating a cell as defined in the above aspects, under conditions conducive to expression of the polypeptide(s) and, optionally, recovering the polypeptide(s).

In another aspect, the invention relates to a process for oxidizing HMFCA to FFA, the process comprising the step of incubating a cell according to any one of the above aspects in the presence of HMFCA, preferably under conditions conducive to the oxidation of HMFCA by the cell.

In yet another aspect, the invention relates to a process for producing FDCA, the process comprising the step of incubating a cell according to any one of the above aspects, in a medium comprising one or more furanic precursors of FDCA, preferably under conditions conducive to the oxidation of furanic precursors of FDCA by the cell to FDCA, and, optionally recovery of the FDCA, wherein preferably, at least one furanic precursor of FDCA is selected from the group consisting of HMF, 2,5-dihydroxymethyl furan (DHF, or HMF-OH), HMFCA, FFA and 2,5-diformyl furan (DFF), of which HMF is most preferred, wherein the furanic precursors of FDCA are obtained from one or more hexose sugars, preferably one or more hexose sugars obtained from lignocellulosic biomass, preferably by acid-catalyzed dehydration, and, wherein preferably the FDCA is recovered from the medium by a process comprising acid or salt precipitation followed by cooling crystallization and/or solvent extraction.

In a further aspect, the invention relates to a process for producing a polymer from one or more FDCA monomers, the process comprising the steps of: a) preparing a FDCA monomer in a process according to the above aspect; and, producing a polymer from the FDCA monomer obtained in a).

The invention also relates to the use of a cell according to any of the above aspects, for the biotransformation of one or more of furanic precursors to FDCA to FDCA, wherein preferably, at least one furanic precursor of FDCA is selected from the group consisting of HMF, DHF, HMFCA, FFA and DFF, of which HMF is most preferred.

In one other aspect the invention relates to a polypeptide having HMFCA dehydrogenase activity, which polypeptide comprises an amino acid sequence that has at least 81.85% sequence identity with the amino acid sequence of SEQ ID NO: 1. In this aspect this invention also relates to a nucleic acid molecule comprising at least one of: a) a nucleotide sequence encoding a polypeptide having HMFCA dehydrogenase activity, which polypeptide comprises an amino acid sequence that has at least 81.85% sequence identity with the amino acid sequence of SEQ ID NO: 1; b) a nucleotide sequence set out in SEQ ID NO: 12 or 13; c) a fragment of a nucleotide sequence as defined in (a) or (b) which is at 10, 15, 20, 30, 50 or 100 nucleotides in length; d) a nucleotide sequence the sequence of which differs from the sequence of a nucleotide sequence of b) or c) due to the degeneracy of the genetic code; and, e) a nucleotide sequence which is the reverse complement of a nucleotide sequence as defined in a) to c), wherein, preferably the nucleic acid molecule is a vector. In this aspect, the invention further relates to a cell comprising at least one of a polypeptide of this aspect, and a nucleic acid molecule of this aspect, wherein preferably the cell is a cultured cell.

In a final aspect the invention relates to a polypeptide having the ability to transport at least HMFCA into the cell, which polypeptide comprises an amino acid sequence that has at least 86.5% sequence identity with the amino acid sequence of SEQ ID NO: 17. In this aspect, the invention also relates to a nucleic acid molecule comprising at least one of: a) a nucleotide sequence encoding a polypeptide having the ability to transport at least HMFCA into the cell, which polypeptide comprises an amino acid sequence that has at least 86.5% sequence identity with the amino acid sequence of SEQ ID NO: 17; b) a nucleotide sequence set out in SEQ ID NO: 18; c) a fragment of a nucleotide sequence as defined in (a) or (b) which is at 10, 15, 20, 30, 50 or 100 nucleotides in length; d) a nucleotide sequence the sequence of which differs from the sequence of a nucleotide sequence of b) or c) due to the degeneracy of the genetic code; and, e) a nucleotide sequence which is the reverse complement of a nucleotide sequence as defined in a) to d), wherein, preferably the nucleic acid molecule is a vector. In this aspect, the invention further relates to a cell comprising at least one of a polypeptide of this aspect, and a nucleic acid molecule of this aspect, wherein preferably the cell is a cultured cell.

DESCRIPTION OF THE INVENTION

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.nchi.nlm.nib.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagines and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

As used herein, the term "selectively hybridizing", "hybridizes selectively" and similar terms are intended to describe conditions for hybridization and washing under which nucleotide sequences at least 66%, at least 70%, at least 75%, at least 80%, more preferably at least 85%, even more preferably at least 90%, preferably at least 95%, more preferably at least 98% or more preferably at least 99% homologous to each other typically remain hybridized to each other. That is to say, such hybridizing sequences may share at least 45%, at least 50%, at least 55%, at least 60%, at least 65, at least 70%, at least 75%, at least 80%, more preferably at least 85%, even more preferably at least 90%, more preferably at least 95%, more preferably at least 98% or more preferably at least 99% sequence identity.

A preferred, non-limiting example of such hybridization conditions is hybridization in 6× sodium chloride/sodium citrate (SSC) at about 45° C., followed by one or more washes in 1×SSC, 0.1% SDS at about 50° C., preferably at about 55° C., preferably at about 60° C. and even more preferably at about 65° C.

Highly stringent conditions include, for example, hybridization at about 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), Sambrook and Russell (2001) "Molecular Cloning: A Laboratory Manual ($3^{rd}$ edition), Cold Spring Harbor Laboratory, Cold Spring Harbor Laboratory Press, New York 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but have been obtained from another cell or synthetically or recombinantly produced. Generally, though not necessarily, such nucleic acids encode proteins, i.e. exogenous proteins, that are not normally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The "specific activity" of an enzyme is herein understood to mean the amount of activity of a particular enzyme per amount of total host cell protein, usually expressed in units of enzyme activity per mg total host cell protein. In the context of the present invention, the specific activity of a particular enzyme may be increased or decreased as compared to the specific activity of that enzyme in an (otherwise identical) wild type host cell.

"Furanic compounds" are herein understood to be 2,5-furan-dicarboxylic acid (FDCA) as well as any compound having a furan group which may be oxidized to FDCA, the latter being referred to herein as a "precursor of FDCA" or a "furanic precursor of FDCA". Precursors of FDCA at least include: 5-hydroxymethylfurfural (HMF), 2,5-dihydroxymethyl furan (DHF or HMF-OH) or 2,5-bis(hydroxymethyl) furan (BHF), 5-hydroxymethyl-2-furancarboxylic acid or 5-hydroxymethyl-2-furoic acid (HMFCA), 5-formyl-2-furoic acid (FFA), and 2,5-diformyl furan (DFF). It is further understood that in the "furanic compounds", the furan ring or any or its substitutable sidegroup may be substituted, e.g. with OH, C1-C10 alkyl, alkyl, allyl, aryl or RO-ether moiety, including cyclic groups, in the furan ring on any available position.

Any reference to nucleotide or amino acid sequences accessible in public sequence databases herein refers to the version of the sequence entry as available on the filing date of this document.

DETAILED DESCRIPTION OF THE INVENTION

Cells Expressing an HMFCA Dehydrogenase

In a first aspect, the invention pertains to a cell that has the ability of oxidizing 5-hydroxymethyl-2-furancarboxylic acid (HMFCA) to 5-formylfuroic acid (FFA). The ability of oxidizing HMFCA to FFA is preferably conferred to the cell or increased in the cell by transformation of the cell with a nucleic acid construct comprising a nucleotide sequence encoding a dehydrogenase that has the ability to oxidize HMFCA to FFA. The dehydrogenase preferably is an alcohol dehydrogenase (i.e. having EC 1.1 activity). Thus, the cell is preferably a cell comprising an expression construct for expression of a nucleotide sequence encoding a dehydrogenase that has the ability to oxidize HMFCA to FFA. In a preferred cell of the invention, the expression construct is expressible in the cell and expression of the dehydrogenase preferably confers to or increases in the cell the ability to oxidize HMFCA to FFA, as compared to a corresponding cell lacking the expression construct, e.g. a wild type cell. The specific activity of the enzyme that oxidizes HMFCA to FFA is preferably increased in the cell by at least a factor 1.05, 1.1, 1.2, 1.5, 2.0, 5.0, 10, 20, 50 or 100 as compared to a corresponding cell lacking the expression construct.

A dehydrogenase that has the ability to oxidize HMFCA to FFA is thus an alcohol dehydrogenase that has HMFCA dehydrogenase activity. Whether or not a polypeptide has HMFCA dehydrogenase activity can be assayed by expression of the polypeptide in a suitable host cell that is incapable of oxidizing HMFCA to FFA and detecting whether or not expression of the polypeptide confers to the cell the ability to oxidize HMFCA to FFA. Preferably, HMFCA dehydrogenase activity is assayed as described in Example IV herein, whereby a nucleotide sequence encoding the polypeptide to be assayed for HMFCA dehydrogenase activity replaces the *C. basilensis* hmfH gene in pBT'h-mfH-adh (described in WO2012/064195), after which the plasmid comprising coding sequence of the polypeptide to be assayed for HMFCA dehydrogenase activity is introduced into *P. putida* KT2440Δgcd containing pJNNhmfT1 (t) (described in WO2012064195). The *P. putida* transformants expressing the polypeptide to be assayed for HMFCA dehydrogenase activity are incubated with HMF and samples are drawn at regular intervals for analysis of FDCA. An increase of production of FDCA, as compared to corresponding *P. putida* transformants lacking the polypeptide to be assayed for HMFCA dehydrogenase activity (and the hmfH gene) is taken as an indication that the polypeptide has HMFCA dehydrogenase activity.

The HMFCA dehydrogenase expressed in the cell of the invention preferably is a dehydrogenase that is dependent on a cofactor selected from an adenine dinucleotide, such as NADH or NADPH, a flavin adenine dinucleotide (FAD), a flavin mononucleotide (FMN), and pyrroloquinoline quinolone (PQQ).

The HMFCA dehydrogenase expressed in the cell of the invention further preferably is an alcohol dehydrogenase that (also) has the ability of oxidizing other furanic alcohols, preferably furanic alcohols with an hydroxy group in the 2-position, to the corresponding aldehydes. Thus, HMFCA dehydrogenase preferably has the ability of oxidizing 5-hydroxymethylfurfural (HMF) to 2,5-diformyl furan (DFF).

In one embodiment the nucleotide sequence encoding the dehydrogenase with the ability to oxidize HMFCA to FFA is selected from the group consisting of:

(a) a nucleotide sequence encoding a polypeptide with HMFCA dehydrogenase activity, which polypeptide comprises an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 81.65, 81.7, 81.8, 81.85, 82, 83, 84, 85, 86, 87, 88, 89, 90, 91, 92, 93, 94, 95, 95, 96, 97, 98, 99 or 100% sequence identity with the amino acid sequence of any one of SEQ ID NO: 1 (*Aeribacillus pallidus*), SEQ ID NO: 2 (*Bacillus kribbensis*), SEQ ID NO: 3 (*Geobacillus kaustophilus*), SEQ ID NO: 4 (*Aneurinibacillus terranovensis*), SEQ ID NO: 5

(*Brevibacillus thermoruber*), SEQ ID NO: 6 (*Brevibacillus panacihumi*), SEQ ID NO: 7 (*Bacillus* sp. FJAT-14578), SEQ ID NO: 8 (*Desulfotomaculum kuznetsovii*), SEQ ID NO: 9 (*Desulfurispora thermophila*), SEQ ID NO: 10 (*Bacillus* sp. L1(2012)) and SEQ ID NO: 11 (*Pelotomaculum thermopropionicum*);

(b) a nucleotide sequence the complementary strand of which hybridises to a nucleotide sequence of (a); and, (c) a nucleotide sequence the sequence of which differs from the sequence of a nucleotide sequence of (b) due to the degeneracy of the genetic code.

A preferred nucleotide sequence of the invention thus encodes a HMFCA dehydrogenase with an amino acid sequence that is identical to that of a HMFCA dehydrogenase that is obtainable from (or naturally occurs in) a bacterium of the Orders Bacillales or Clostridiales. In one preferred embodiment, the bacterium is of the Family Bacillaceae, more preferably the bacterium is of the genera *Aeribacillus*, *Geobacillus* and *Bacillus*, of which the species *Aeribacillus pallidus*, *Bacillus kribbensis*, *Geobacillus kaustophilus*, *Aneurinibacillus terranovensis*, *Bacillus* sp. FJAT-14578 and *Bacillus* sp. L1(2012) are most preferred. In another preferred embodiment, the bacterium is of the Family Paenibacillaceae, more preferably a bacterium of the genera *Aneurinibacillus* and *Brevibacillus*, of which the species *Aneurinibacillus terranovensis*, *Brevibacillus thermoruber* and *Brevibacillus panacihumi*, are most preferred. In yet another preferred embodiment, the bacterium is of the Family Peptococcaceae, more preferably the bacterium is of the genera *Desulfotomaculum*, *Desulfurispora* and *Pelotomaculum*, of which the species *Desulfotomaculum kuznetsovii*, *Desulfurispora thermophila* and *Pelotomaculum thermopropionicum* are most preferred.

In one embodiment, a preferred nucleotide sequence of the invention encodes a HMFCA dehydrogenase from a mesophilic bacterium, i.e. a bacterium that grows best in moderate temperature, typically between 20 and 45° C. Preferably, nucleotide sequence of the invention encodes a mesophilic HMFCA dehydrogenase with optimal activity and stability in the range between 20 and 45° C. Examples of such mesophilic dehydrogenases are e.g. the dehydrogenase from *Bacillus kribbensis* (30° C.), *Aneurinibacillus terranovensis* (40° C.), *Brevibacillus thermoruber* (45° C.), *Brevibacillus panacihumi* (30° C.), *Bacillus* sp. FJAT-14578 (30° C.) and *Bacillus* sp. L1(2012) (30-50° C.) and dehydrogenase related thereto.

In one embodiment, a preferred nucleotide sequence of the invention encodes a HMFCA dehydrogenase from a thermophilic bacterium, i.e. a bacterium that grows best in relatively high temperatures, typically between higher than 45 and 122° C. Preferably, nucleotide sequence of the invention thus encodes a thermophilic HMFCA dehydrogenase with optimal activity and stability in the range between higher than 45 and 122° C. Examples of such thermophilic dehydrogenases are e.g. the dehydrogenase from *Aeribacillus pallidus* (55° C.), *Geobacillus kaustophilus* (55° C.), *Desulfotomaculum kuznetsovii* (60° C.), *Desulfurispora thermophila* (50° C.), *Pelotomaculum thermopropionicum* (55° C.) and *Bacillus* sp. L1(2012) (30-50° C.) and dehydrogenase related thereto.

In one embodiment the nucleotide sequence encodes a polypeptide with HMFCA dehydrogenase activity as it occurs in nature, e.g. as it can isolated from a wild type source organism. Alternatively, the nucleotide sequence can encode engineered forms of any of the HMFCA dehydrogenase defined above and that comprise one or more amino acid substitutions, insertions and/or deletions as compared to the corresponding naturally occurring HMFCA dehydrogenase but that are within the ranges of identity or similarity as defined herein. Therefore, in one embodiment the nucleotide sequence of the invention encodes a HMFCA dehydrogenase the amino acid sequence of which at least comprises in each of the invariable positions (that are indicated in Table 2 with a "*"), the amino acid present in a invariable position. Preferably, the amino acid sequence also comprises in the strongly conserved positions (that are indicated in Table 2 with a ":") one of the amino acids present in a strongly conserved position. More preferably, the amino acid sequence further also comprises in the less strongly conserved positions (that are indicated in Table 2 with a ".") one of the amino acids present in a less strongly conserved position. Amino acid substitutions outside of these invariable and conserved positions are less unlikely to affect HMFCA dehydrogenase activity.

The nucleotide sequences of the invention, encoding polypeptides with HMFCA dehydrogenase activity, are obtainable from genomic and/or cDNA of a fungus, yeast or bacterium, e.g. one that belongs to the same phylum, class or genus as the source organisms described above, using methods for isolation of nucleotide sequences that are well known in the art per se (see e.g. Sambrook and Russell (2001) "Molecular Cloning: A Laboratory Manual ($3^{rd}$ edition), Cold Spring Harbor Laboratory, Cold Spring Harbor Laboratory Press, New York). The nucleotide sequences of the invention are e.g. obtainable in a process wherein a) degenerate PCR primers (designed on the basis of conserved amino acid sequences) are used on genomic and/or cDNA of a suitable organism to generate a PCR fragment comprising part of the nucleotide sequences encoding the polypeptides with HMFCA dehydrogenase activity; b) the PCR fragment obtained in a) is used as probe to screen a cDNA and/or genomic library of the organism; and c) producing a cDNA or genomic DNA comprising the nucleotide sequence encoding a polypeptide with HMFCA dehydrogenase activity.

To increase the likelihood that a HMFCA dehydrogenase of the invention is expressed at sufficient levels and in active form in the transformed cells of the invention, the nucleotide sequence encoding these enzymes, as well as other enzymes of the invention (see below), are preferably adapted to optimise their codon usage to that of the host cell in question. The adaptiveness of a nucleotide sequence encoding a polypeptide to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences as listed in SEQ ID NO's: 13 or 14, which have been codon optimised for expression in *P. putida* cells.

The host cell to be transformed with a nucleic acid construct for expression of the nucleotide sequence encoding a HMFCA dehydrogenase of the invention can in principle be any host cell in which the HMFCA dehydrogenase invention can suitably be expressed, preferably in functional, i.e. active form. The host cell of the invention, preferably is a host capable of active or passive transport of furanic compounds into as well as out of the cell. A preferred host cell of the invention lacks or has no detectable activities that decarboxylate carboxylated furanic compounds, such as in particular HMFCA, FFA and FDCA. Such a host cell preferably naturally lacks the ability to decarboxylate carboxylated furanic compounds.

Preferably the host cell is a cultured cell, e.g. a cell that may be cultured in a fermentation process, preferably in submerged fermentation.

According to an embodiment, the host cell according to the invention is a eukaryotic host cell. Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. 519 and Sf21 cells and derivatives thereof.

Preferably, however, the host cell is a microbial cell. The cell can be eukaryotic microbial cell, preferably a fungal cell, such as e.g. a yeast or filamentous fungal cell. Preferred yeast host cells include e.g. cells from yeasts from genera such as *Candida, Hansenula, Kluyveromyces, Pichia, Saccharomyces, Schizosaccharomyces*, and *Yarrowia*. More preferably yeasts from species such as *Kluyveromyces lactis, S. cerevisiae, Hansenula polymorpha, Yarrowia lipolytica* and *Pichia pastoris*. Preferred filamentous fungal cells include e.g. cells from filamentous fungal from genera such as *Acremonium, Agaricus, Aspergillus, Aureobasidium, Myceliophthora, Chrysosprorium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium*, and *Trichoderma*. Preferred filamentous fungal cells belong to a species of an *Aspergillus, Myceliophthora, Penicillium, Myceliophthora, Talaromyces* or *Trichoderma* genus, and most preferably a species selected from *Aspergillus niger, Aspergillus awamori, Aspergillus foetidus, Aspergillus sojae, Aspergillus fumigatus, Talaromyces emersonii, Aspergillus oryzae, Myceliophthora thermophila, Trichoderma reesei* and *Penicillium chrysogenum*.

The microbial host cell can also be a prokaryotic cell, preferably a bacterial cell. The term "bacterial cell" includes both Gram-negative and Gram-positive microorganisms. Suitable bacteria may be selected from the genera *Escherichia, Anabaena, Aeribacillus, Aneurinibacillus, Burkholderia, Bradyrhizobium, Caulobacter, Cupriavidus, Desulfotomaculum, Desulfurispora, Gluconobacter, Rhodobacter, Pelotomaculum, Pseudomonas, Paracoccus, Bacillus, Geobacillus, Brevibacillus, Brevibacterium, Corynebacterium, Rhizobium (Sinorhizobium), Flavobacterium, Klebsiella, Enterobacter, Lactobacillus, Lactococcus, Methylobacterium, Ralstonia, Rhodopseudomonas, Staphylococcus* and *Streptomyces*. Preferably, the bacterial cell is selected from a species from the group consisting of *A. pallidus, A. terranovensis, B. subtilis, B. amyloliquefaciens, B. coagulans, B. kribbensis, B. licheniformis, B. puntis, B. megaterium, B. halodurans, B. pumilus, B. thermoruber, B. panacihumi, C. basilensis, D. kuznetsovii, D. thermophila, G. kaustophilus, Gluconobacter oxydans, Caulobacter crescentus CB 15, Methylobacterium extorquens, Rhodobacter sphaeroides, Pelotomaculum thermopropionicum, Pseudomonas zeaxanthinifaciens, Pseudomonas putida, Paracoccus denitrificans, E. coli, C. glutamicum, Staphylococcus carnosus, Streptomyces lividans, Sinorhizobium melioti* and *Rhizobium radiobacter*. Within the species *Pseudomonas putida*, the strains *P. putida* S12 and *P. putida* KT2440 are preferred.

For specific uses of a compound produced in a host cell according to the invention, the selection of the host cell may be made according to such use. Where e.g. the compound produced in a host cell according to the invention is to be used in food applications, a host cell may be selected from a food-grade organism such as *Saccharomyces cerevisiae*. Specific uses include, but are not limited to, food, (animal) feed, pharmaceutical, agricultural such as crop-protection, and/or personal care applications.

The expression construct for expression of a nucleotide sequence encoding a HMFCA dehydrogenase of the invention, preferably is an expression construct that is heterologous or exogenous to the host cell transformed with the construct. A construct is herein understood to be heterologous or exogenous to the host cell comprising the construct when the construct comprises at least one sequence or sequence element that does not naturally occur in the host cell and/or when construct comprises at least two sequence elements in a combination and/or order that does not naturally occur in the host cell, even if the elements themselves do naturally occur in the host cell.

Vectors and expression constructs for expression of a nucleotide sequence encoding a HMFCA dehydrogenase of the invention in appropriate host cells are described in more detail herein below.

A transformed cell expressing an HMFCA dehydrogenase of the invention, further preferably has aldehyde dehydrogenase activity (i.e. having EC 1.2 activity). Preferably, the aldehyde dehydrogenase activity is capable of converting furanic aldehydes. More preferably the aldehyde dehydrogenase activity is capable of oxidizing furanic aldehydes to the corresponding furanic carboxylic acids. More specifically, the aldehyde dehydrogenase activity is preferably capable of at least one of i) oxidizing HMF to HMFCA, ii) oxidizing 2,5-diformyl furan (DFF) to 5-formyl-2-furoic acid (FFA), and iii) FFA into FDCA. Such furanic aldehyde dehydrogenase activity can be an endogenous activity of the cell or it can be an exogenous activity conferred to the cell. Preferably, the furanic aldehyde dehydrogenase activity is conferred to or increased in the cell by transformation of the cell with a second expression construct. In a preferred cell of the invention, the second expression construct is expressible in the cell and expression of the furanic aldehyde dehydrogenase preferably confers to or increases in the cell the ability to oxidize at least one of i) oxidizing HMF to HMFCA, ii) oxidizing DFF to FFA, and iii) oxidizing FFA into FDCA, as compared to a corresponding cell lacking the expression construct, e.g. a wild type cell. The specific activity of the furanic aldehyde dehydrogenase is preferably increased in the cell by at least a factor 1.05, 1.1, 1.2, 1.5, 2.0, 5.0, 10, 20, 50 or 100 as compared to a corresponding cell lacking the expression construct. The second expression construct preferably comprises a nucleotide sequence encoding a polypeptide:

a) having at least one of the abilities of i) oxidizing HMF to HMFCA, ii) oxidizing DFF to FFA, and, iii) oxidizing FFA into FDCA; and, b) comprising an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of any one of SEQ ID NO's: 24, 25, 26, 27, 28, 29 and 30.

The ability of a polypeptide to oxidize at least one of i) HMF to HMFCA, ii) oxidizing DFF to FFA, and iii) FFA to FDCA, may be assayed by co-expression of a nucleotide sequence encoding the polypeptide in a *P. putida* host cell, preferably an *P. putida* KT2440 host cell, together with the HmfH and HmfT1 genes from *C. basilensis* HMF 14, incubating the *P. putida* cells in 10 mM HMF and detecting an increase in the accumulation FDCA as compared to corresponding *P. putida* cells that do not express the polypeptide, e.g. as described in Example IV of WO2012/064195. The ability of a polypeptide to oxidize HMF to HMFCA may also be assayed as described by Koopman et al 2010, PNAS supra). Strains expressing the HmfT1 gene from *C. basilensis* HMF14 are herein understood to express a gene product having the amino acid sequence of SEQ ID NO: 31.

A transformed cell expressing an HMFCA dehydrogenase of the invention, further preferably has the ability of transporting furanic compounds into and/or out of the cell. Preferably the cell has the ability to transport furanic compounds that are precursors for FDCA into the cell and preferably the ability to transport FDCA out of the cell. Such furanic compound transport capabilities can be an endogenous capabilities of the cell and/or they can be an exogenous capabilities conferred to the cell. Thus, a preferred cell of the invention expresses a polypeptide having furanic compound transport capabilities. More preferably, the cell expresses a polypeptide having HMFCA transport capabilities. HMFCA transport capabilities are understood to at least include the capability to transport HMFCA into the cell. Expression of a polypeptide having HMFCA transport capabilities will increase transport of HMFCA into the cell, which increases its availability for intracellular conversion to FDCA. Thus HMFCA bioconversion can be improved.

Preferably, the ability to transporting furanic compounds into and/or out of the cell is conferred to or increased in the cell by transformation of the cell with a third expression construct. In a preferred cell of the invention, the third expression construct is expressible in the cell and expression of the furanic compound transporter preferably confers to or increases in the cell the ability to transport at least HMFCA into the cell, compared to a corresponding cell lacking the expression construct, e.g. a wild type cell. The third expression construct preferably comprises a nucleotide sequence encoding a polypeptide:

a) having at least HMFCA transport capability; and,
b) comprising an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of any one of SEQ ID NO's: 17, 31, 32, 33 and 34.

The ability of a polypeptide to transport furanic compounds, in particular HMFCA, into the cell may be assayed by co-expression of a nucleotide sequence encoding the transporter polypeptide in a *P. putida* host cell, preferably a *P. putida* KT2440 host cell, together with the HmfH gene from *C. basilensis* HMF 14 and a gene encoding a furanic aldehyde dehydrogenase associated with the HMF-degradation operon from *C. basilensis* HMF 14 (having the amino acid sequence of SEQ ID NO: 19 of WO2012/064195), incubating the *P. putida* cells in 10 mM HMF and detecting an increase in the accumulation FDCA as compared to corresponding *P. putida* cells that do not express the transporter polypeptide, e.g. as described in Example IV of WO2012/064195.

In one embodiment the nucleotide sequence encodes a polypeptide having HMFCA transport capability as it occurs in nature, e.g. as it can isolated from a wild type source organism. Alternatively, the nucleotide sequence can encode engineered forms of any of the polypeptides having HMFCA transport capability as defined above and that comprise one or more amino acid substitutions, insertions and/or deletions as compared to the corresponding naturally occurring polypeptide having HMFCA transport capability but that are within the ranges of identity or similarity as defined herein. Therefore, in one embodiment the nucleotide sequence of the invention encodes a polypeptide having HMFCA transport capability the amino acid sequence of which at least comprises in each of the invariable positions (that are indicated in Table 3 with a "*"), the amino acid present in a invariable position. Preferably, the amino acid sequence also comprises in the strongly conserved positions (that are indicated in Table 3 with a ":") one of the amino acids present in a strongly conserved position. More preferably, the amino acid sequence further also comprises in the less strongly conserved positions (that are indicated in Table 3 with a ".") one of the amino acids present in a less strongly conserved position. Amino acid substitutions outside of these invariable and conserved positions are less unlikely to affect the HMFCA transport capability.

The nucleotide sequences of the invention, encoding polypeptide having HMFCA transport capability, are obtainable from genomic and/or cDNA of a fungus, yeast or bacterium, e.g. one that belongs to the same phylum, class or genus as the source organisms described above, using methods for isolation of nucleotide sequences that are well known in the art per se, in a similar manner as described above for the nucleotide sequences encoding HMFCA dehydrogenases of the invention.

Cells Expressing a Transporter of Furanic Compounds

In a second aspect, the invention pertains to a cell expressing a nucleotide sequence encoding a polypeptide having furanic compound transport capabilities. Preferably the cell is transformed with an expression construct for expression of a nucleotide sequence encoding a polypeptide having furanic compound transport capabilities. The polypeptide having furanic compound transport capabilities preferably is a polypeptide having HMFCA transport capabilities, which at least includes the capability to transport HMFCA into the cell. Preferably the cell comprises an expression construct for expression of a nucleotide sequence encoding a polypeptide having the ability to transport at least HMFCA into the cell, the polypeptide comprising an amino acid sequence with at least 86.5, 87, 88, 89, 90, 91, 92, 93, 94, 95, 95, 96, 97, 98, 99 or 100% identity with the amino acid sequence of SEQ ID NO: 17, wherein, the expression construct is expressible in the cell and expression of the polypeptide confers to or increases in the cell the ability to transport at least HMFCA into the cell, as compared to a corresponding wild type cell lacking the expression construct. The ability of a polypeptide to transport furanic compounds, in particular HMFCA, into the cell may be assayed as described above.

Preferably, a transformed cell expressing a transporter of furanic compounds of this aspect of the invention further comprises enzyme activities for converting HMF into FDCA, wherein the activities for converting HMF into FDCA preferably include at least one of:

a) an alcohol dehydrogenase that oxidizes HMFCA to FFA and an aldehyde dehydrogenase activity that oxidizes furanic aldehydes to the corresponding furanic carboxylic acids; and,
b) an oxidoreductase, preferably an oxidase, that oxidizes one or more of HMF, 2,5-dihydroxymethyl furan, HMFCA, FFA and 2,5-diformyl furan to FDCA and optionally an aldehyde dehydrogenase activity that oxidizes furanic aldehydes to the corresponding furanic carboxylic acids.

The alcohol dehydrogenase that oxidizes HMFCA to FFA and the aldehyde dehydrogenase activity that oxidizes furanic aldehydes preferably are as defined herein above. The oxidoreductase that oxidizes one or more of HMF, 2,5-dihydroxymethyl furan, HMFCA, FFA and 2,5-diformyl furan to FDCA preferably is an oxidoreductase having both EC 1.1 and EC 1.2 activities, as described in WO2011/026913.

Unless otherwise specified, a transformed cell expressing a transporter of furanic compounds of this aspect of the invention further may have the features of a cell expressing an HMFCA dehydrogenase of the first aspect of the invention as defined above.

Vectors and Constructs and Method for Expression of Polypeptides of the Invention Another aspect of the invention pertains to nucleic acid constructs, such as vectors, including cloning and expression vectors, comprising a polynucleotide of the invention, e.g. a nucleotide sequence encoding a HMFCA dehydrogenase or a transporter of the invention or a functional equivalent thereof and methods of growing, transforming or transfecting such vectors in a suitable host cell, for example under conditions in which expression of a polypeptide of the invention occurs. As used herein, the terms "vector" and "construct" are used interchangeably and refers to a constructed nucleic acid molecule comprising and preferably capable of transporting a polynucleotide of the invention.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described above.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome (s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell.

A vector of the invention may comprise two or more, for example three, four or five, polynucleotides of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operably linked to the nucleic acid sequence to be expressed. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide. The term "regulatory sequence" or "control sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990). The term regulatory or control sequences includes those sequences which direct constitutive expression of a nucleotide sequence in many types of host cells and those which direct expression of the nucleotide sequence only in a certain host cell (e.g. tissue-specific regulatory sequences).

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; (2) translation initiation sequences, such as the eukaryotic Kozak consensus sequence or the prokaryotic Ribosome Binding Site/Shine-Dalgarno sequence, (3) optionally, a signal sequence capable of directing secretion of the polypeptide from the given host cell into a culture medium; (4) a DNA sequence of the invention encoding a mature and preferably active form of a polypeptide of the invention; and preferably also (5) a transcription termination region (terminator) capable of terminating transcription downstream of the nucleotide sequence encoding the polypeptide.

Downstream of the nucleotide sequence according to the invention there may be a 3' untranslated region containing one or more transcription termination sites (e. g. a terminator). The origin of the terminator is less critical. The terminator can, for example, be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide of the invention may also be achieved by the selection of heterologous regulatory regions, e. g. promoter, secretion leader and/or terminator regions, which may serve to increase expression and, if desired, secretion levels of the protein of interest from the expression host and/or to provide for the inducible control of the expression of a polypeptide of the invention.

It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein (e.g. HMFCA dehydrogenase or a transporter of the invention, mutant forms thereof, fragments, variants or functional equivalents thereof, fusion proteins, etc.).

As set out above, the term "control sequences" or "regulatory sequences" is defined herein to include at least any component which may be necessary and/or advantageous for the expression of a polypeptide. Any control sequence may be native or foreign to the nucleic acid sequence of the invention encoding a polypeptide. Such control sequences may include, but are not limited to, a promoter, a leader, optimal translation initiation sequences (as described in Kozak, 1991, J. Biol. Chem. 266:19867-19870) or the prokaryotice Shine-Delgarno sequences, a secretion signal sequence, a pro-peptide sequence, a polyadenylation sequence, a transcription terminator. At a minimum, the control sequences typically include a promoter and translational initiation and stop signals.

A stably transformed microorganism is one that has had one or more DNA fragments introduced such that the introduced molecules are maintained, replicated and segregated in a growing culture. Stable transformation may be due to multiple or single chromosomal integration (s) or by (an) extrachromosomal element(s) such as (a) plasmid vector(s). A plasmid vector is capable of directing the expression of polypeptides encoded by particular DNA fragments.

Expression may be constitutive or regulated by inducible (or repressible) promoters that enable high levels of transcription of functionally associated DNA fragments encoding specific polypeptides.

Regardless of the exact mechanism utilized for expression of polypeptides of the invention, it is contemplated that such expression is transferable by the introduction of genes encoding these polypeptides into another host cell by methods known in the art. Genetic elements as herein defined include nucleic acids (generally DNA or RNA) having expressible coding sequences for products such as proteins, specifically enzymes, apoproteins or antisense RNA, which express or regulate expression of relevant polypeptides. The expressed proteins can function as enzymes, repress or derepress enzyme activity or control expression of enzymes or function as transporter of compounds, e.g. metabolites. Recombinant DNA encoding these expressible sequences can be either chromosomal (integrated into the host cell chromosome by, for example, homologous recombination) or extra-chromosomal (for example, carried by one or more plasmids, cosmids and other vectors capable of self replication). It is understood that the recombinant DNA utilized for transforming the host cell in accordance with this invention can include, in addition to structural genes and transcription factors, expression control sequences, including promoters, repressors and enhancers, that act to control expression or derepression of coding sequences for proteins, apoproteins or antisense RNA. For example, such control sequences can be inserted into wild-type host cells to promote overexpression of selected polypeptides already encoded in the host cell genome, or alternatively they can be used to control synthesis of extrachromosomally encoded polypeptides.

Recombinant DNA can be introduced into the host cell by any means, including, but not limited to, plasmids, cosmids, phages, yeast artificial chromosomes or other vectors that mediate transfer of genetic elements into a host cell. These vectors can include an origin of replication, along with cis-acting control elements that control replication of the vector and the genetic elements carried by the vector. Selectable markers can be present on the vector to aid in the identification of host cells into which genetic elements have been introduced.

Means for introducing genetic elements into a host cell (e.g. cloning) are well known to the skilled artisan. One can utilize an extrachromosomal multi-copy plasmid vector to insert the genetic elements in accordance with the present invention. Plasmid-borne introduction of the genetic element into host cells involves an initial cleaving of a plasmid vector with a restriction enzyme, followed by ligation of the plasmid and genetic elements encoding for the targeted enzyme species in accordance with the invention. Upon recircularization of the ligated recombinant plasmid, infection (e.g., packaging in phage lambda) or other mechanism for plasmid transfer (e.g., electroporation, microinjection, etc.) is utilized to transfer the plasmid into the host cell. Plasmids suitable for insertion of genetic elements into the host cell are well known to the skilled artisan.

Other gene cloning methods include, but are not limited to, direct integration of the genetic material into the chromosome. This can occur by a variety of means, including cloning the genetic elements described herein on non-replicating plasmids flanked by homologous DNA sequences of the host chromosome; upon transforming said recombinant plasmid into a host the genetic elements can be introduced into the chromosome by DNA recombination. Such recombinant strains can be recovered if the integrating DNA fragments contain a selectable marker, such as antibiotic resistance. Alternatively, the genetic elements can be directly introduced into the chromosome of a host cell without use of a non-replicating plasmid. This can be done by synthetically producing DNA fragments of the genetic elements in accordance to the present invention that also contain homologous DNA sequences of the host chromosome. Again if these synthetic DNA fragments also contain a selectable marker, the genetic elements can be inserted into the host chromosome.

The invention further relates to method for the preparation of a polypeptide having a HMFCA dehydrogenase activity of the invention and/or a polypeptide having furanic compound transport capabilities of the invention, which method comprises cultivating a cell according to the invention under conditions conducive to expression of the polypeptide and, optionally, recovering the expressed polypeptide, as well as to a polypeptide obtainable by such a method.

Processes for the Oxidation of Furanic Compounds

In a further aspect, the invention pertains to processes for oxidizing furanic compounds. In particular the invention pertain to process wherein furanic precursors of FDCA are oxidized. A process of the invention may comprise a single oxidation reaction step resulting in a product (e.g. the oxidation of HMFCA to FFA). Alternatively a process of the invention may comprise more than one oxidation reaction step, each step resulting in an intermediate, where the last intermediate is the final product. Examples of such a series of steps, wherein HMF is oxidized in sequential oxidation steps to FDCA include e.g.: 1) HMF is first oxidized to HMFCA, which in a second step is oxidized to FFA, which is then finally oxidized to FDCA, or alternatively, as described by Dijkman et al. (2014, Angew. Chem. 53 (2014) 6515-8) 2) HMF is first oxidized to DFF, which in a second step is oxidized to FFA, which is then finally oxidized to FDCA. Thus, in a preferred process of the invention one or more furanic precursors of FDCA are oxidized in a series of steps to ultimately FDCA.

In one embodiment, the invention relates to processes comprising at least the oxidation of HMFCA to FFA. Preferably, the process is a process for oxidizing HMFCA to FFA, wherein the process comprises the step of incubating a cell in the presence of HMFCA, wherein the cell is a cell expressing an HMFCA dehydrogenase as herein defined above, or a cell expressing polypeptide having furanic compound transport capabilities and further comprising a HMFCA dehydrogenase or oxidase activities as herein defined above. Preferably the cell is incubated in the presence of HMFCA under conditions conducive to the oxidation of HMFCA by the cell, as e.g. specified below.

In another embodiment, the invention relates to processes for producing FDCA. A process for producing FDCA preferably comprises the step of incubating a cell in a medium comprising one or more furanic precursors of FDCA, wherein the cell is a cell expressing an HMFCA dehydrogenase as herein defined above, or a cell expressing polypeptide having furanic compound transport capabilities and further comprising a HMFCA dehydrogenase or oxidase activities as herein defined above. Preferably the cell is incubated in the presence of HMFCA under conditions conducive to the oxidation furanic precursors of FDCA by the cell to FDCA, as e.g. specified below.

Preferably in the process, at least one furanic precursor of FDCA is selected from the group consisting of HMF, DHF, HMFCA, FFA and DFF, of which HMF is most preferred. The furanic precursors of FDCA are preferably obtained from one or more hexose sugars, preferably by acid-catalyzed dehydration, e.g. by heating in presence of acid, in a conventional manner. The technology to generate HMF from fructose is well established and robust (see e.g. van Putten et al., 2013, Chem. Rev. 113, 1499-1597). Also glucose-rich feedstock can be utilized, but the thermochemical formation of HMF proceeds more efficiently from fructose. Therefore, an additional enzymatic step can be included to convert glucose to fructose, using glucose isomerase. The latter process is well-established in food industry e.g. for producing high fructose corn syrup (HFCS) from hydrolysed starch. Glucose can also be chemically isomerized to fructose using combinations of catalysts and solvents as e.g. described in van Putten et al. (2013, supra).

The hexose sugars will usually be obtained from biomass. The term "biomass" is understood to mean the biodegradable fraction of products, waste and residues from biological origin from agriculture (including vegetal, such as crop residues, and animal substances), forestry (such as wood resources) and related industries including fisheries and aquaculture, as well as biodegradable fraction of industrial and municipal waste, such as municipal solid waste or wastepaper. In a preferred embodiment, the biomass is plant biomass, more preferably a (fermentable) hexose/glucose/sugar-rich biomass, such as e.g. sugarcane, a starch-containing biomass, for example, wheat grain, or corn straw, or even cereal grains, such as corn, wheat, barley or mixtures thereof. Preferred are agricultural crops naturally rich in fructans (e.g., topinambur or chicory roots).

The hexose sugars can be obtained by hydrolysis of such biomass Methods for hydrolysis of biomass are known in the art per se and include the use of e.g. vapour and/or carbohydrases such as glucoamylases.

Another preferred type of biomass for use in the process of the invention is a so-called "second generation" lignocellulosic feedstock, which are preferred if large volumes of FDCA are to be produced in a more sustainable way. Lignocellulosic feedstocks can be obtained from dedicated energy crops, e.g. grown on marginal lands, thus not competing directly with food crops. Or lignocellulosic feedstocks can be obtained as by-products, e.g. municipal solid wastes, wastepaper, wood residues (including sawmill and paper mill discards) and crop residues can be considered. Examples of crop residues include bagasse from sugar cane and also several corn and wheat wastes. In the case of corn by-products, three wastes are fiber, cobs and stover. Furthermore, forestry biomass may be used as feedstock. In order to convert second generation feedstocks into fermentation products of the invention, the cellulose and hemicellulose need to be released as monosaccharides. Hereto, either thermochemical approaches (usually referred to as pretreatment), enzymatic approaches or a combination of the two methodologies are applied. A pretreatment can serve to either completely liberate the sugars, or to make the polymeric compounds more accessible to subsequent enzymatic attack. Different types of pretreatment include liquid hot water, steam explosion, acid pretreatment, alkali pretreatment, and ionic liquid pretreatments. The relative amounts of the various compounds will depend both on the feedstock used and the pretreatment employed. For release of monosaccharide sugars from such lignocellulosic feedstock, appropriate carbohydrases are employed, including e.g. arabinases, xylanases, glucanases, amylases, cellulases, glucanases and the like.

The process of the invention further preferably comprises the step of recovery of the oxidation product(s) produced in the process, such as FDCA, or HMFCA. Preferably, the oxidation product is recovered from the medium in which the cell carrying out the oxidation steps is incubated. Oxidation products such as FDCA, HMFCA, etc. may be recovered from the reaction mixture or medium by e.g. (acid or salt) precipitation, subsequent cooling crystallisation, and separation of the crystallized oxidation product, e.g., crystallized FDCA. However, other recovery methods are suitable, such as e.g. acid or salt precipitation and solvent extraction, as known in the art. Salt precipitation for recovery of FDCA can e.g. be performed using divalent (metal) cations, such as e.g. $Mg^{2+}$.

The oxidation reactions are preferably conducted at temperature most optimal to the cell and the oxidoreductase enzymes contained is the cell. Thus, in case of thermophilic cells and enzymes the temperature preferably is than 45° C. or higher, e.g. in the range between 45 and 122° C., e.g. higher than 50, 55, 60 or 65° C. However, in the case of a mesophilic cell containing enzymes from mesophiles, the oxidation reactions are preferably conducted at a relatively mild temperature, e.g. 10-80° C., more preferably 20-45° C., most preferably around from 25-40° C.

The oxidation reactions are preferably conducted at a pH where FDCA is either in a neutral form or in a fully dissociated form, such that salt formation may be controlled. In view of the presence of two acid moieties in FDCA there are two separate preferred pH ranges. The pH during the reaction may be from pH 1 to 6, preferably from pH 1 to 4, most preferably from pH 1 to 3. Alternatively the pH during the reaction may be from pH 5 to 9, preferably from pH 5 to 8, most preferably from pH 5 to 7. The skilled person will understand that the requirements of the host cell will also influence the selection of a suitable pH value for the process. Selection of pH values that are appropriate for a particular host cell is within the ambit of the skilled person and may be derived from standard text books. For *Pseudomonas putida*, including e.g. *Pseudomonas putida* S12 or KT2440 strains, the preferred pH range is from pH 5 to 7.

The reaction time may be 6-150 hrs, more preferably 6-18 hrs. Preferably oxygen is supplied to the cells in the reaction medium from an oxygen source, such as molecular oxygen, e.g. as pure oxygen or in air, or water, or a different source of oxygen depending on the requirements of the furanic oxidizing enzyme. Air may be used conveniently as a source of molecular oxygen.

The reactor may be any suitable (aerated) bioreactor. It may be operated in batch, continuous or preferably in fed-batch.

The processes of the invention for oxidizing furanic compounds may advantageously be applied for the elimination of furanic compounds from feedstocks wherein furanic compounds are considered to be detrimental, such as feedstocks for fermentations for the production of biofuels and biochemicals. More preferably, the processes for oxidizing furanic compounds are applied in the bioproduction of FDCA as a monomeric precursor for the production of polyesters (plastics), wherein FDCA may substitute for PTA in the polyester PET in which case biobased polyethylene-furandicarboxylate (PEF) results. FDCA may also be used as a substrate for a large variety of valuable compounds, including e.g. as substrate for the production of succinic acid, 2,5-bis(aminomethyl)-tetrahydrofuran, 2,5-dihydroxymethyl-tetrahydrofuran, 2,5-dihydroxymethylfuran and 2,5-furandicarbaldehyde. FDCA may be used in the production of coatings, e.g. in alkyd resin and thermoplastic coatings. It may also be used as a xylene equivalent in biofuels and as solvent. FDCA may be esterified, and the esters may be used as plasticizers. FDCA may converted to its diol, that may be used in PET-like polyesters and polyurethanes. Further FDCA may be converted into its diamine, the diamine may be used as chain extender and the diamine may be converted into di-isocyanate, which can be used in the production of polyurethanes.

Thus, in a further aspect the invention relates to a process for producing a polymer from one or more FDCA monomers, the process comprising the steps of: a) preparing a FDCA monomer in an oxidation process of the invention as described above; and, b) producing a polymer from the FDCA monomer obtained in a). Preferably the polymer is polyethylenefurandicarboxylate (PEF).

In yet another aspect, the invention pertains to the use of a cell of the invention, for the biotransformation of one or more of furanic precursors to FDCA to FDCA, wherein the cell is a cell expressing an HMFCA dehydrogenase as herein defined above, or a cell expressing polypeptide having furanic compound transport capabilities and further comprising a HMFCA dehydrogenase or oxidase activities as herein defined above. Preferably, at least one furanic precursor of FDCA that is biotransformed to FDCA is selected from the group consisting of HMF, DHF, HMFCA, FFA and DFF, of which HMF is most preferred.

HMFCA Dehydrogenase Polypeptides and Nucleic Acids Encoding HMFCA Dehydrogenases In a further aspect the invention relates to a polypeptide having HMFCA dehydrogenase activity. The polypeptide having HMFCA dehydrogenase activity comprises or consist of an amino acid sequence that has at least 81.65, 81.7, 81.8, 81.85, 82, 83, 84, 85, 86, 87, 88, 89, 90, 91, 92, 93, 94, 95, 95, 96, 97, 98, 99 or 100% sequence identity with the amino acid sequence of SEQ ID NO: 1 (*Aeribacillus pallidus*) but is otherwise as herein defined above. Preferably the polypeptide is an isolated polypeptide.

The invention further relates to a nucleic acid molecule comprising at least one of:
a) a nucleotide sequence encoding a polypeptide having HMFCA dehydrogenase activity, which polypeptide comprises or consist of an amino acid sequence that has at least 81.65, 81.7, 81.8, 81.85, 82, 83, 84, 85, 86, 87, 88, 89, 90, 91, 92, 93, 94, 95, 95, 96, 97, 98, 99 or 100% sequence identity with the amino acid sequence of SEQ ID NO: 1;
b) a nucleotide sequence set out in SEQ ID NO: 12 or 13;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In yet another aspect, the invention pertains to a cell comprising at least one of i) a polypeptide having HMFCA dehydrogenase activity as defined above in this section, and ii) a nucleic acid molecule as defined above in this section. Preferably the cell is a cell comprising or transformed with a nucleotide sequence as defined in a) to e) above in this section, or a vector comprising such a nucleotide sequence. The cell preferably is an isolated cell or a cultured cell, the cell preferably is otherwise as described herein above and preferably the cell comprises one or more of the genetic modifications described herein above. The cell can be applied in any of the methods, processes and uses as described above.

Furanic Compound Transporter Polypeptides and Nucleic Acids Encoding Such Transporter Polypeptides In a again a further aspect the invention relates to a polypeptide having furanic compound transport capabilities. The polypeptide preferably at least has the capability to transport HMFCA into the cell. Preferably the polypeptide comprises or consist of an amino acid sequence that has at least 86.5, 87, 88, 89, 90, 91, 92, 93, 94, 95, 95, 96, 97, 98, 99 or 100% sequence identity with the amino acid sequence of SEQ ID NO: 17 (*Aeribacillus pallidus*) but is otherwise as herein defined above. Preferably the polypeptide is an isolated polypeptide.

The invention further relates to a nucleic acid molecule comprising at least one of:
  a) a nucleotide sequence encoding a polypeptide having the ability to transport at least HMFCA into the cell, which polypeptide comprises or consist of an amino acid sequence that has at least 86.5, 87, 88, 89, 90, 91, 92, 93, 94, 95, 95, 96, 97, 98, 99 or 100% sequence identity with the amino acid sequence of SEQ ID NO: 17;
  b) a nucleotide sequence set out in SEQ ID NO: 18;
  c) a fragment of a nucleotide sequence as defined in (a) or (b) which is at 10, 15, 20, 30, 50 or 100 nucleotides in length;
  d) a nucleotide sequence the sequence of which differs from the sequence of a nucleotide sequence of b) or c) due to the degeneracy of the genetic code; and,
  e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In yet another aspect, the invention pertains to a cell comprising at least one of i) a polypeptide having furanic compound transport capabilities as defined above in this section, and ii) a nucleic acid molecule as defined above in this section. Preferably the cell is a cell comprising or transformed with a nucleotide sequence as defined in a) to e) above in this section, or a vector comprising such a nucleotide sequence. The cell preferably is an isolated cell or a cultured cell, the cell preferably is otherwise as described herein above and preferably the cell comprises one or more of the genetic modifications described herein above. The cell can be applied in any of the methods, processes and uses as described above.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Figure 1A:
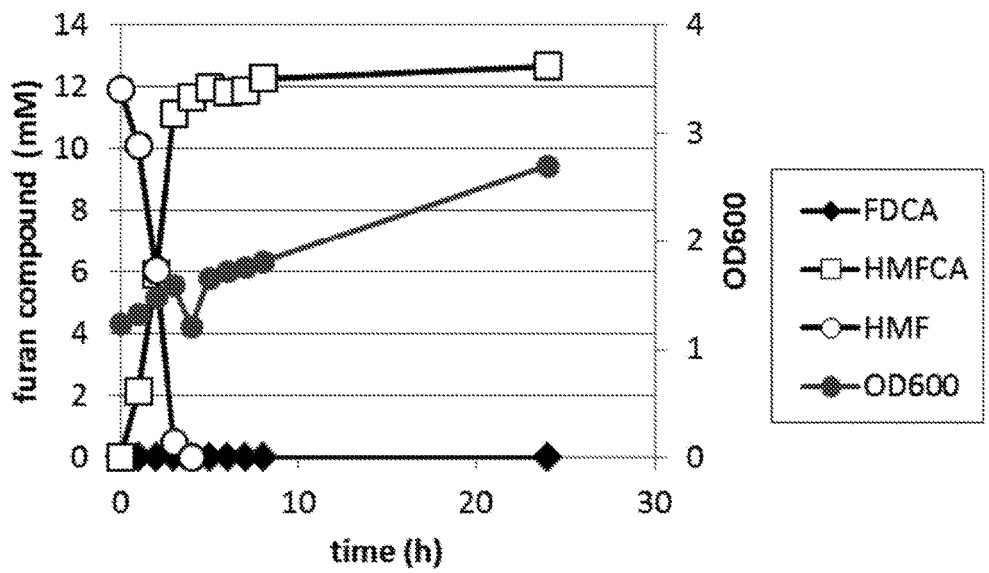
FIG. 1A: Biotransformation of HMF by *P. putida* CA2046 (*P. putida*; open circle: HMF (5-hydroxymethylfurfural); open square: HMFCA (5-hydroxymethylfuroic acid); filled diamond: FDCA (2,5-furan dicarboxylic acid); filled grey circle: OD600.

General Methodology
Strains and Plasmids

*Pseudomonas putida* S12Δgcd or *P. putida* KT2440Δgcd (glucose-dehydrogenase deficient mutants of *P. putida* S12 (ATCC 700801), resp., *P. putida* KT2440 (DSM6125)), or wild type *P. putida* S12, were used as the host for expression of the yiaY gene from *Aeribacillus pallidus* strain CA1828 (see below). *Escherichia coli* strain TG90 was used for general cloning purposes.

For episomal expression of the *A. pallidus* gene the pBBR1MCS-derived pBT'mcs (Koopman et al., 2010a, Biores Technol 101: 6291-6196) was used. In pBT'mcs the expression of the target gene is driven from the constitutive tac promoter.

Media & Culture Conditions

Mesophile mineral salts medium (MMM) contained the following (per liter of demineralized water): 15.52 g of $K_2HPO_4$, 6.52 g of $NaH_2PO_4$, 2.0 g of $(NH_4)_2SO_4$, 0.1 g of $MgCl_2.6H_2O$, 10 mg of EDTA, 2 mg of $ZnSO_4.7H_2O$, 1 mg of $CaCl_2.2H_2O$, 5 mg of $FeSO_4.7H_2O$, 0.2 mg of $Na_2MoO_4.2H_2O$, 0.2 mg of $CuSO_4.5H_2O$, 0.4 mg of $CoCl_2.6H_2O$, and 1 mg of $MnCl_2.2H_2O$, supplemented with a carbon source as specified.

Thermophile mineral salts medium (TMM) contained the following (per liter of demineralized water): 10 g of Bis-Tris, 10 µM $FeSO_4.7H2O$, 4 mM tricine, 1.32 mM K2HPO4, 9.53 mM NH4Cl, 0.2 g yeast extract, 5 g of NaCl, 1.47 g of Na2SO4, 0.08 g of NaHCO3, 0.25 g of KCl, 1.87 g of MgCl2.6H2O, 0.41 g of CaCl2.2H2O, 0.008 g of SrCl2.6H2O, 0.008 g of H3BO3, 0.90 g of NaNO3, and 1 ml of vitamin solution (Thiamine, 0.1 g/L; Riboflavin, 0.1 g/L; Nicotinic acid, 0.5 g/L, Panthothenic acid, 0.1 g/L; Pyridoxamine-HCl, 0.5 g/L; Pyridoxal-HCl, 0.5 g/L; D-Biotin, 0.1 g/L; Folic acid, 0.1 g/L; p-Aminobenzoic acid, 0.1 g/L; Cobalamin, 0.1 g/L). Carbon sources were supplemented as specified.

As complete medium for propagation of mesophiles, Luria-Bertani (LB) broth was used: 10 g/l Bacto trypton (Difco), 5 g/l yeast extract (Difco), 10 g/l NaCl. For plate culturing, LB was solidified with 1.5% (w/v) of agar (Difco). For selection of either *E. coli*, *P. putida* S12 or *P. putida* KT2440 transformants carrying pBT'mcs-derived plasmids, 50 µg/ml of kanamycin (Km) was added to the media. Antibiotics were purchased from Sigma-Aldrich. *P. putida* was cultured at 30° C.; *E. coli* was cultured at 37° C.

As complete medium for propagation of thermophiles, TGP broth was used: 17 g/L trypton, 3 g/L soy pepton, 5 g/L NaCl, 2.5 g/L K2HPO4, 4 g/L glycerol and 4 g/L Na-pyruvate (pH7). For plate culturing, TGP was solidified with 1.5% (w/v) of agar (Difco). *Aeribacillus pallidus* was cultivated at 60° C.

Assays & Analytical Methods

Cell Dry Weight (CDW) Measurement:

CDW content of bacterial cultures was determined by measuring optical density at 600 nm ($OD_{600}$) using a Biowave Cell Density Meter (WPA Ltd) or a µQuant MQX200 universal microplate spectrophotometer (Biotek), using flat-bottom 96-well microplates (Greiner). An $OD_{600}$ of 1.0 corresponds to 0.56 g CDW/L (Biowave) or 1.4 g CDW/L (µQuant) for *P. putida*.

HPLC Analyses:

Furan compounds (FDCA, HMF, HMF-alcohol, HMFCA and FFA) were analyzed by RP-HPLC as described by Koopman et al. (2010a, Biores Technol 101: 6291-6196).

Chemicals

5-Hydroxymethylfurfural (HMF) was purchased at Eurolabs Ltd (Poynton, UK). Analytical standards of FDCA and 5-hydroxymethyl-furoic acid (HMFCA) were purchased from Immunosource B.V. (Halle-Zoersel, Belgium), respectively, Matrix Scientific (Columbia S.C., USA). All other chemicals were purchased from Sigma-Aldrich Chemie B.V. (Zwijndrecht, The Netherlands).

Molecular and Genetic Techniques:

Genomic DNA was isolated from *A. pallidus* CA1828 using the MasterPure™ Gram Positive DNA Purification Kit (Epicentre). Plasmid DNA was isolated with the JETSTAR Maxi Plasmid Purification Kit (GENOMED, ITK diagnostics). Agarose-trapped DNA fragments were isolated with the DNA Clean & Concentrator™ (Zymo research). PCR reactions were performed with Phusion Flash PCR Master Mix (Thermo Scientific) according to the manufacturer's instructions. Oligonucleotide primers (specified in the examples) were synthesized by Sigma-Aldrich. Plasmid DNA was introduced into electrocompetent cells using a Gene Pulser electroporation device (BioRad). Other standard molecular biology techniques were performed according to Sambrook and Russell (2001, supra).

Example I: Isolation of HMF Metabolizing *Aeribacillus pallidus* Strains

Compost (15 g) was mixed with 15 ml of 0.9% (w/v) NaCl solution and incubated for 40 min at 750 rpm and 80° C. The resulting compost slurry was incubated in TMM supplemented with 0.65 g/L of HMF in shake flasks at 60° C. and 180 rpm for 3 days. The culture was transferred at regular intervals to fresh TMM-HMF and plated on solid TMM-HMF. Single colonies were re-streaked on TMM-HMF and TGP plates, and reassessed for their ability to metabolize HMF and also FDCA. Two isolates that metabolized both HMF and FDCA (strain CA1809 and CA1828) were identified as *Aeribacillus pallidus* by 16S rDNA sequencing and selected for further study.

Example II: Identification of a Novel, Dehydrogenase-Catalysed HMF Catabolic Pathway in HMF Degrading *A. pallidus* Isolates The genomes of *A. pallidus* strains CA1809 and CA1828 were sequenced through PacBio sequencing, and automated ORF calling and annotation was performed. In the annotated genomes, homologues were identified of the hmfABCDE genes of *Cupriavidus basilensis* HMF14 which constitute the furoic acid degradation cluster (Koopman et al., 2010, Proc Nat Acad Sci USA 107: 4919-4924).

Considering the ability of strains CA1809 and CA1828 to metabolize FDCA in addition to HMF strongly suggested that HMF was metabolized via FDCA as in *C. basilensis* HMF14. However, unexpectedly no homologue of the hmfFGH cluster of *C. basilensis* HMF14 was found which constitutes the degradation pathway from HMF to furoic acid via FDCA. This result suggested that an alternative pathway for the oxidation of HMF to FDCA, and possibly the subsequent decarboxylation to furoic acid, existed in the *A. pallidus* isolates. Mining the genomes for gene clusters that comprised genes encoding both oxidizing and decarboxylating activities resulted in the identification of a putative HMF degradation cluster, comprising genes encoding an alcohol dehydrogenase, an aldehyde dehydrogenase, and two decarboxylases (Tables 1 A and B). Together, these genes encode a putative pathway for the oxidation of HMF to FDCA, via hydroxymethylfuroic acid (HMFCA), as in *C. basilensis* HMF14 but involving an alcohol dehydrogenase activity for the oxidation of HMFCA to formylfuroic acid (FFA) rather than an oxidase activity.

TABLE 1 A

Putative HMF degradation cluster of *A. pallidus* CA1809

| locus ID | best BLAST hit | % identity (x AA/y AA) | % similarity (x AA/y AA) | putative function | Corresponding locus in *C. basilensis* HMF14 | % identity (x AA/y AA) | % similarity (x AA/y AA) |
|---|---|---|---|---|---|---|---|
| 03430 | MFS transporter [*Geobacillus kaustophilus*] Sequence ID: ref WP_011229501.1 | 86 (384/446) | 93 (418/446) | MFS transporter | hmfT1 | 60 (270/450) | 75 (341/450) |
| 03431 | 4-hydroxybenzoate decarboxylase [*Geobacillus kaustophilus*] Sequence ID: ref| WP_011229502.1 | 87 (405/466) | 94 (442/466) | FDCA decarboxylase subunit | hmfF | 52 (240/462) | 68 (315/462) |

TABLE 1 A-continued

Putative HMF degradation cluster of *A. pallidus* CA1809

| locus ID | best BLAST hit | % identity (x AA/y AA) | % similarity (x AA/y AA) | putative function | Corresponding locus in *C. basilensis* HMF14 | % identity (x AA/y AA) | % similarity (x AA/y AA) |
|---|---|---|---|---|---|---|---|
| 03432 | alcohol dehydrogenase [*Geobacillus kaustophilus*] Sequence ID: ref\| WP_011229504.1 | 82 (320/392) | 92 (363/392) | HMFCA dehydrogenase | — | | |
| 03433 | aldehyde dehydrogenase [*Geobacillus kaustophilus*] Sequence ID: ref\| WP_011229505.1 | 88 (429/488) | 95 (466/488) | HMF/FFA dehydrogenase | aldh | 37 (174/470) | 55 (261/470) |
| 03434 | phenolic acid decarboxylase subunit B [*Geobacillus kaustophilus*] Sequence ID: ref\| WP_011229508.1\| | 91 (162/179) | 96 (172/179) | FDCA decarboxylase subunit | hmfG | 54 (99/183) | 74 (136/183) |

TABLE 1 B

Putative HMF degradation cluster of *A. pallidus* CA1828

| locus ID | best BLAST hit | % identity (x AA/y AA) | % similarity (x AA/y AA) | putative function | Corresponding locus in *C. basilensis* HMF14 | % identity (x AA/y AA) | % similarity (x AA/y AA) |
|---|---|---|---|---|---|---|---|
| 03227 | MFS transporter [*Geobacillus kaustophilus*] Sequence ID: ref\| WP_011229501.1 | 86 (384/446) | 93 (418/446) | MFS transporter | hmfT1 | 61 (232/383) | 76 (293/383) |
| 03228 | 4-hydroxybenzoate decarboxylase [*Geobacillus kaustophilus*] Sequence ID: ref\| WP_011229502.1 | 87 (405/466) | 94 (442/466) | FDCA decarboxylase subunit | hmfF | 52 (240/462) | 68 (315/462) |
| 03229 | alcohol dehydrogenase [*Geobacillus kaustophilus*] Sequence ID: ref\| WP_011229504.1 | 82 (320/392) | 92 (363/392) | HMFCA dehydrogenase | — | | |
| 03230 | aldehyde dehydrogenase [*Geobacillus kaustophilus*] Sequence ID: ref\| WP_011229505.1 | 88 (429/488) | 95 (466/488) | HMF/FFA dehydrogenase | aldh | 37 (174/470) | 55 (261/470) |
| 03231 | phenolic acid decarboxylase subunit B [*Geobacillus kaustophilus*] Sequence ID: ref\| WP_011229508.1\| | 91 (162/179) | 96 (172/179) | FDCA decarboxylase subunit | hmfG | 54 (99/183) | 74 (136/183) |

Example III: Expression of YiaY from *A. pallidus* in *P. putida* S12 Confers the Ability to Oxidize HMF to FDCA The yiaY gene was cloned as a 1988-bp synthetic XbaI-SalI fragment (SEQ ID NO: 15), including the PldhL1 promoter region from *B. coagulans* DSM1, in pBT'mcs yielding plasmid pKW007. Plasmid pKW007 was introduced into *P. putida* KT2440Δgcd (CA1877), yielding *P. putida* CA2101. *P. putida* KT2440Δgcd carrying pBT'mcs (strain CA2046) was tested as an empty vector control.

Figure 1B:
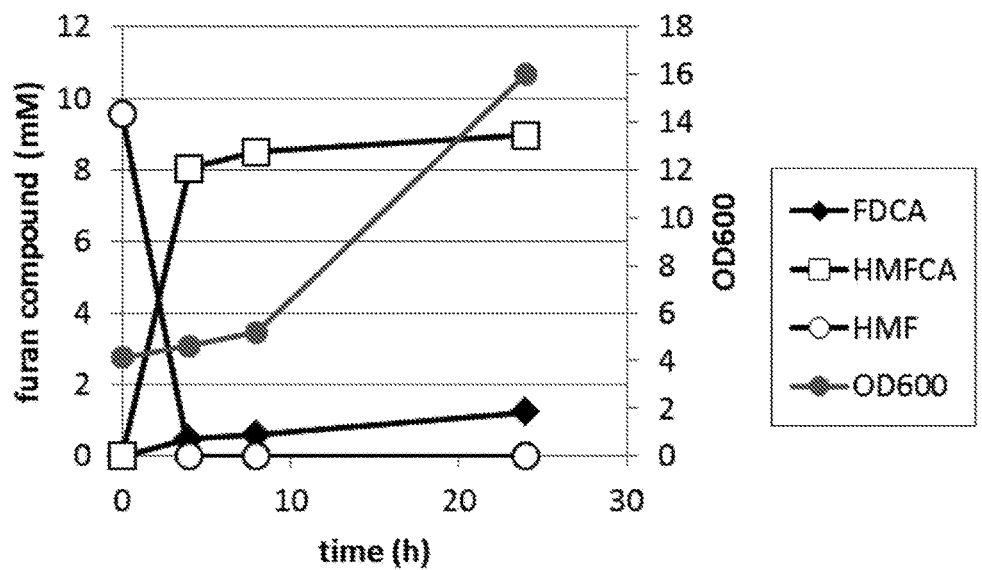
FIG. 1B: Biotransformation of HMF by *P. putida* CA2101; open circle: HMF (5-hydroxymethylfurfural); open square: HMFCA (5-hydroxymethylfuroic acid); filled diamond: FDCA (2,5-furan dicarboxylic acid); filled grey circle: OD600.

*P. putida* strains CA2101 and CA2046 were grown in 100-ml shake flasks containing 10 ml of MM+80 mM glycerol and 2 mM glucose supplemented with 50 mg/L kanamycin. Cells were harvested at the end of the log phase (OD600≈4), washed and resuspended in MM supplemented with 19.4 g/L of K2HPO4, 8.15 g/L of NaH2PO4, 80 mM glycerol and 50 mg/L kanamycin. Aliquots (10 ml) of washed cell suspensions (at an OD600 of 1-2) were incubated with HMF in 100-ml Erlenmeyer flasks and samples were drawn at regular intervals for analysis of FDCA. FIG. 1A shows that HMF is rapidly oxidized to hydroxymethyl-furoic acid (HMFCA) in the empty vector control, whereas FDCA formation was totally absent. When YiaY was expressed (FIG. 1B), the accumulated HMFCA was slowly oxidized to FDCA, which demonstrated the functionality of YiaY as an HMFCA-oxidizing dehydrogenase.

Example IV: Optimized Oxidation of HMF to FDCA Through Coexpression of YiaY from *A. pallidus* and Aldh and HmfT1 from *C. basilensis* HMF14

The yiaY gene of *A. pallidus* CA1828 was synthesized including the ribosome binding site TAG-GAAAGGAAGATTAACCC (SEQ ID NO: 21). The yiaY fragment (SEQ ID NO: 16) was digested with KpnI and XbaI to replace the hmfH gene in pBT'hmfH-adh (WO2012064195) yielding plasmid pKW010. Plasmid pKW010 was introduced into pJNNhmfT1(t) (WO2012064195)-harbouring *P. putida* S12Δgcd yielding *P. putida* CA2111, and into *P. putida* KT2440Δgcd (also harbouring pJNNhmfT1(t)) yielding *P. putida* CA2112. Thus, the HMFCA oxidizing alcohol dehydrogenase encoded by yiaY could be co-expressed with the HMF dehydrogenase and the HMFCA transporter from *C. basilensis* HMF14 to eliminate the bottlenecks of HMF oxidation to HMFCA and HMFCA uptake.

Figure 2:
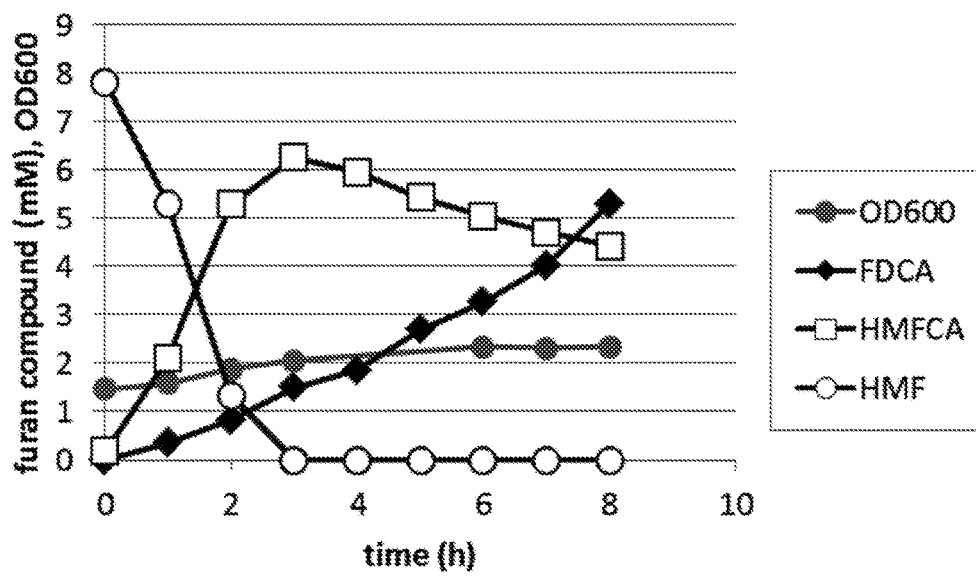
FIG. 2: Biotransformation of HMF by *P. putida* CA2111, coexpressing YiaY with Aldh and HmfT1 from *C. basilensis* HMF14; open circle: HMF (5-hydroxymethylfurfural); open square: HMFCA (5-hydroxymethylfuroic acid); filled diamond: FDCA (2,5-furan dicarboxylic acid); filled grey circle: OD600. Averages of duplicate cultures are shown.
Figure 3:
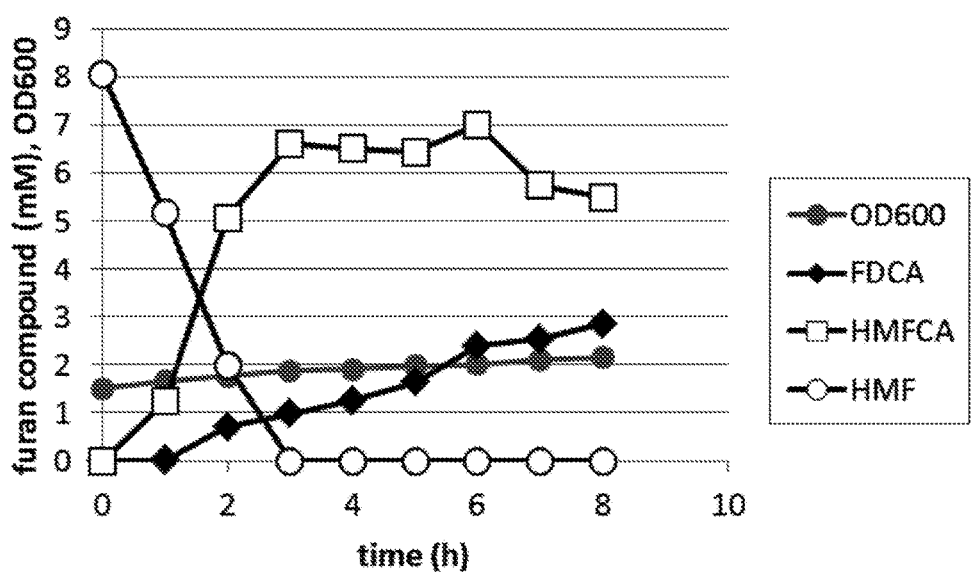
FIG. 3: Biotransformation of HMF by *P. putida* CA2112, coexpressing YiaY with Aldh and HmfT1 from *C. basilensis* HMF14; open circle: HMF (5-hydroxymethylfurfural); open square: HMFCA (5-hydroxymethylfuroic acid); filled diamond: FDCA (2,5-furan dicarboxylic acid); filled grey circle: OD600. Averages of duplicate cultures are shown.

*P. putida* CA2111 and CA2112 were grown in 100-ml shake flasks containing 10 ml of MM+80 mM glycerol and 2 mM glucose supplemented with 50 mg/L kanamycin, 30 mg/L of gentamicin and 100 µM of salycilic acid. Cells were harvested at the end of the log phase (OD600≈4), washed and resuspended in MM 50 mg/L kanamycin, 30 mg/L gentamicin and 10 µM of salicylic acid. Aliquots (10 ml) of washed cell suspensions (at an OD600 of 1-2) were incubated with HMF in 100-ml Erlenmeyer flasks and samples were drawn at regular intervals for analysis of FDCA. FIGS. 2 and 3 show that HMF is rapidly oxidized to HMFCA, which is further oxidized to FDCA. It is clear that coexpression of YiaY with Aldh and HmfT1 considerably accelerates the oxidation of HMF to FDCA.

Example V: Construction of Optimized Strains for Oxidation of HMF to FDCA Through Coexpression of Mesophilic HMFCA Alcohol Dehydrogenases and Aldh and HmfT1 from *C. basilensis* HMF14

The yiaY homologue of *Bacillus kribbensis* DSM17871, *Brevibacillus thermoruber* 423, *Bacillus* sp. FJAT-14578, and *Bacillus* sp. L1(2012) were synthesized including a ribosome binding site containing spacer TAG-GAAAGGAAGATTAACCC (SEQ ID NO: 21) as well as recognition sites for restriction enzymes (KpnI, resp., NheI; compatible with XbaI)) for cloning (SEQ ID NO.'s: 19, 36, 38 and 39).

The yiaY homologues of *Aneurinibacillus terranovensis* DSM18919 and *Brevibacillus panacihumi* W25 were synthesized including a ribosome binding site containing spacer GAATTCCACATGACAAGGGGAGACCGC (SEQ ID NO: 40) as well as recognition sites for restriction enzymes (KpnI, resp., XbaI) for cloning (SEQ ID NO.'s: 35 and 37). The coding nucleotide sequence for the *B. kribbensis* enzyme (SEQ ID NO: 19), the *B. thermoruber* enzyme (SEQ ID NO: 36) and both *Bacillus* sp. enzymes (SEQ ID NO: 38 and 39) were obtained via reverse translation of the amino acid sequences (http://www.bioinformatics.org/sms2/rev_trans.html) using the *P. putida* codon usage table of http://www.kazusa.or.jp/codon/. The coding nucleotide sequence for the *A. terranova* and *B. panacihumi* enzyme was obtained via reverse translation of the amino-acid sequences using the *E. coli* sequence optimization tool of GeneArt (https://www.thermofisher.com/nl/en/home/life-science/cloning/gene-synthesis/geneart-gene-synthesis/geneoptimizer.html).

The yiaY-homologue fragments of *B. kribbensis*, *B. thermoruber*, *Bacillus* sp. FJAT-14578, and *Bacillus* sp. L1(2012) were digested with KpnI and NheI (compatible with XbaI in pBT'hmfH-adh) to replace the hmfH gene in pBT'hmfH-adh (WO2012064195) yielding plasmids pKW2210, pKW2212, pKW2214, and pKW2215. The yiaY-homologue fragments of *A. terranovensis* and *B. panacihumi* were digested with KpnI and XbaI to replace the hmfH gene in pBT'hmfH-adh (WO2012064195) yielding plasmids pKW2211 and pKW2213.

Figure 4:
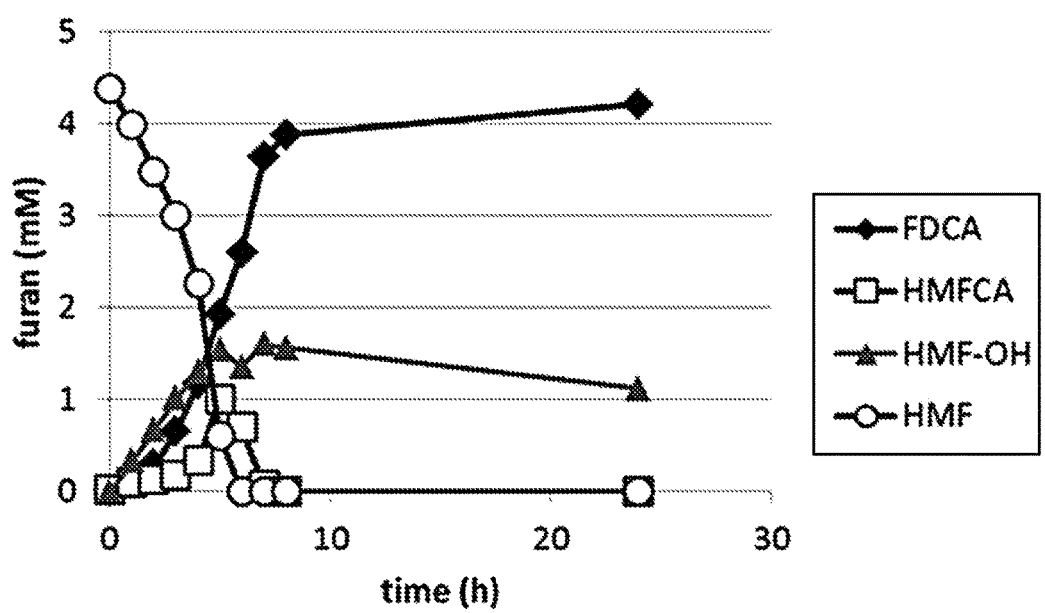
FIG. 4. HMF biotransformation by *P. putida* CA21780, co-expressing YiaY from *Bacillus kribbensis* DSM17871, and Aldh and HmfT1 from *C. basilensis*. HMF-OH is dihydroxymethyl furan, also referred to as "DHF" herein.
Figure 5:
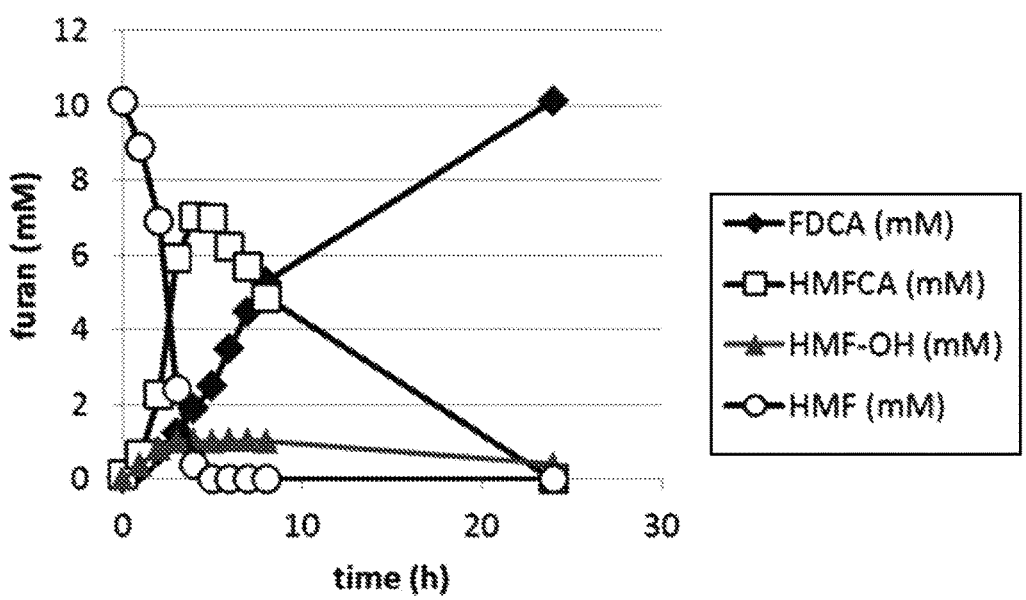
FIG. 5. HMF biotransformation by *P. putida* CA21781, co-expressing YiaY from *Aneurinibacillus terranovensis* DSM18919, and Aldh and HmfT1 from *C. basilensis*. HMF-OH is dihydroxymethyl furan, also referred to as "DHF" herein.
Figure 6:
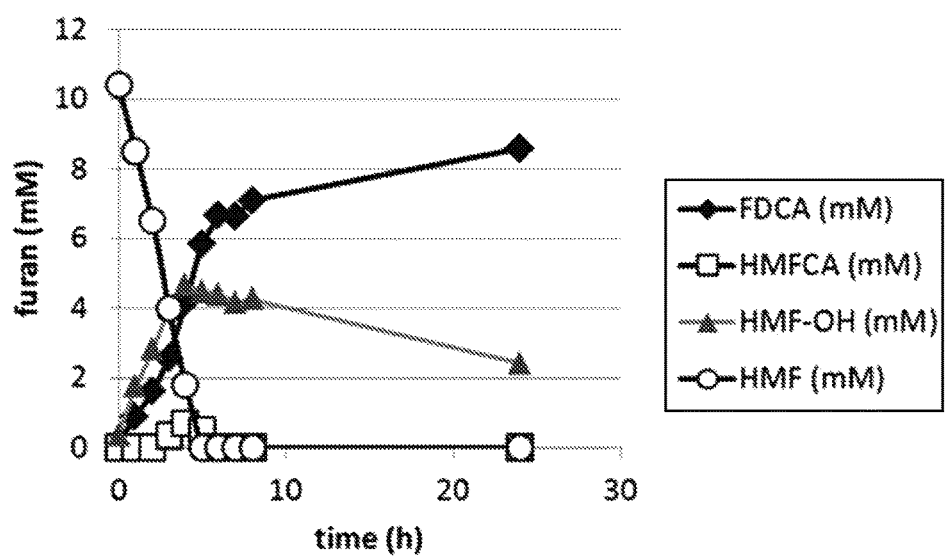
FIG. 6. HMF biotransformation by *P. putida* CA21783, co-expressing YiaY from *Brevibacillus panacihumi* W25, and Aldh and HmfT1 from *C. basilensis*. HMF-OH is dihydroxymethyl furan, also referred to as "DHF" herein.

Plasmids pKW2210, pKW2211, pKW2212, pKW2213, pKW2214 and pKW2215 were introduced into *P. putida* KT2440Δgcd_pJNNhmfT1 (CA1965), yielding, respectively, *P. putida* CA21780, CA21781, CA21782, CA21783, CA21784 and CA21785 for expression of the YiaY homologues in an optimized host background including aldh and hmfT1. For performance evaluation, *P. putida* strains CA21780, CA21781, CA21782, CA21783, CA21784 and CA21785 were grown in 100-ml shake flasks containing 10 ml of MM+80 mM glycerol and 2 mM glucose supplemented with 50 mg/L kanamycin, 30 mg/L of gentamicin and 100 µM of salicylic acid. Cells were harvested at the end of the log phase (OD600≈4), washed and resuspended in MM 50 mg/L kanamycin, 30 mg/L gentamicin and 10 µM of salicylic acid. Aliquots (10 ml) of washed cell suspensions (OD600 of 1-2) were incubated with HMF in 100-ml Erlenmeyer flasks and samples were drawn at regular intervals for analysis of FDCA. The results for *P. putida* CA21780, CA21781 and CA21783 are shown in FIGS. 4, 5 and 6, respectively. All three transformed strains produced FDCA from HMF. The different strains, however showed marked differences in transient accumulation of HMFCA and partial reduction of HMF to dihydroxymethyl furan (HMF-OH or DHF). Strains *P. putida* CA21782, CA21784 and CA21785 were also found to produce FDCA from HMF, demonstrating the functionality of all six alcohol dehydrogenases as HMFCA oxidizing enzymes.

Example VI: Construction of a *P. putida* Strain Expressing the *Aeribacillus pallidus* proP Encoded HMFCA Transporter The proP gene (SEQ ID NO: 18) was amplified from genomic DNA of *Aeribacillus pallidus* CA1828 by PCR using primers proP(f) (gccgaattcAT-GAAGAATATCGCTAATACG; SEQ ID NO: 22) and proP (r) (gccgctagcTTATTTGAGGTTTCCTTTTGTTTCC; SEQ ID NO: 23). The PCR product was introduced as a 1350-bp EcoRI-NheI fragment (SEQ ID NO: 20) in pJNNmcs(t) yielding pJNNproP(t). Plasmids pBT'hmfH aldh and pJN-NproP(t) were successively introduced into *P. putida* KT2440Δgcd (CA1877), yielding *P. putida* CA21783. *P. putida* CA21783 was cultured in 100-ml shake flasks containing 10 ml of MM+80 mM glycerol and 2 mM glucose supplemented with 50 mg/L kanamycin, 30 mg/L of gentamicin and 100 µM of salycilic acid. Cells were harvested at the end of the log phase (OD600=4), washed and resuspended in MM 50 mg/L kanamycin, 30 mg/L gentamicin and 10 µM of salicylic acid. Aliquots (10 ml) of washed cell suspensions (OD600 of 1-2) were incubated with HMF in 100-ml Erlenmeyer flasks and samples were drawn at regular intervals for analysis of FDCA. It is clear that expression of the proP-encoded HMFCA transporter considerably accelerates the oxidation of HMF to FDCA as compared to a corresponding control strain that does not express proP.

TABLE 2

YiaY amino acid sequence alignment

```
Adh_Bp      ---------MESPFSFHLPTNVQFGVGSASRLGEMLLSMGVRRVFLVTDQGVRQAGLLDE
Adh_Bk      ---------MDVEFSFHLPTLIEFGFGKASLLGERLLKLGVGNVFLVSDKGVASAGLLQK
Adh_Bt      --MSQTVQGTDFAFSFHLPTLIEFGYGRASRLGERLQHLGVTNVFVVTDKGVEAAGLLNG
Adh_At      --MSPAVKAINFEFSFNLPTLIEFGYGKMEKFGQQLISIGVKRIFMVTDKGVESAGLLAA
YiaY        MIGNYAKKAIDFEFTFYLPTLIEFGYGKASRMGEMLEQMGIKNVFLVTDKGVEAAGLLAG
Adh_Gk      MVGHYIQKEVEFEFSFHLPTSIQFGYGKASQLGNQLVDMGIKSAFLVTDRGVEATGLLAG
Adh_Bsp     ---------MYPSFEFHLPTKIHFGYNTIKQLDH--LPFEIKRAFIVTDQGVLNSGLVEN
Adh_BspL1   ------------------------------------------------------------
Adh_Pt      ------------------------------------------------------------
Adh_Dk      ------------------------------------------------------------
Adh_Dt      ----------------MKTTVCFGANIVSSIDDRCRDYNARHVLIVTDQGVEKAGILEK

Adh_Bp      VIHSLEEKGLHFQIYADVEPDPSLETIQAGAAMFQQQSFDCMVAIGGGSPIDTAKGIRVL
Adh_Bk      LEQSLQTSDIHFKTYLEVEPDPSLETIDLGARAFNSGKYDCIVAVGGGSAIDTAKGIRVV
Adh_Bt      LVGSLQSAGIAFDLYTEVEPDPGLETIDRGAAVFRAKPYDCLVAVGGGSPIDAAKGMRVV
Adh_At      LTDSLQAAAIQFDIYTDVESDPSLETIDRGVEVFQQKPYDCIVAVGGGSPIDTAKGIRVV
YiaY        IVQSLESSNIRYVIYSDVEPDPSLETIDRGASVFKEQSFDCILAVGGGSPIDTAKGIRVV
Adh_Gk      IIQSLESSNIQYCVYADVEPDPSLETIDQGAAAFKEQPFDCIVAIGGGSPIDTAKGIRVV
Adh_Bsp     VTNILKDHQISYVIYSEVEPDPSVETVDKAAQMFQREEADALIAIGGGSPIDTAKGVRVI
Adh_BspL1   -------------------PSVETVDKAAKAFAEAECDLLIAVGGGSPIDTAKGVRVV
Adh_Pt      ----------------VEPDPGLETVHKAAAFLGRTRPDCLVALGGGSSIDVAKGARVI
Adh_Dk      -------------------DPGLETIHRCASCFRENKCDLILAVGGGSPIDTAKGARVI
Adh_Dt      VEKVLSDAGIENVVFDDVEPDPGLETIHRCASCFRENKCDLFLAIGGGSPIDTAKGARII
                 *..:**:.    .   :       * ::*:**** **.*** *::

Adh_Bp      AANGGGIGQYAGVNRVPAASAIPLIAIPTTSGTGSEVTIFGVYSDWENHVKITVTSPHMA
Adh_Bk      AGNGGSIGDFAGVDKIGKAPQIPLIAVPTTSGTGSEVTIFGVYSDWVKNVKVTVTSQYMA
Adh_Bt      TSCGGSIADYAGVNRVPMAPAVPLVAVPTTSGTGSEVTMFGVYSDWHNHVKVTVTSPHMA
Adh_At      AANGGNIGHYAGVNQIPVAPTIPLLAIPTTSGTGSEVTNFGVYSDWQNNVKVTVTSQYMA
YiaY        VTNGGNIGDYAGVNRVAKKSEIPLVAVPTTSGTGSEVTIFGVYSDWENQVKVTVTSPYMA
Adh_Gk      ATNGGSIGDYAGVNRIKKKSEIPLIALPTTSGTGSEVTIFGVYSDWKNNVKVTVTSPYMA
Adh_Bsp     AGNGGSIRDYAGVNLIKQKSNIPLTATPTTSGTGSEVTIFAVFSDWEENRKVTVTSPFLA
Adh_BspL1   ASNGGSIRNYSGVNLVKEAPSVPLVAIPTTAGTGSEVTIFAVFSDDKENRKVTVTSSHLS
Adh_Pt      YDNGGKISDYAGVNKVKVKPSLPLMAVPTTAGTGSEVTVFAVLSDWEQNIKITVTSEYLA
Adh_Dk      VENGGHIRDYAGVNKVPRAPVTPLTATPTTSGTGSEVTTFAVLSDWENRMKITISSPFLA
Adh_Dt      VDNGGHIRDYAGVNKVPRAPRTPLLAIPTTSGTGSEVTTFAVLSDWENRMKITISSPFLA
                 ** *  .::**: :       **:*:***:******* *.* **    :. *:*::* .::

Adh_Bp      PSTALIDPALTLSLPAKMTAATGIDALAHGIETFFSLRSSPASDALAIHAMKMIAPHLRR
Adh_Bk      PTIALVDPELTMRLPRKMTAASGIDALAHGIESYFSLRSTSASRALSLEAINIVGNHLRQ
Adh_Bt      PTIALVDPALTVSLPAKMTAASGIDALAHGIETFFSVRSRPASDALAMEAIAAVNAHLRR
Adh_At      PTIAWVDPALTMSLPAKMTAASGIDALAHGIETFFSLGSSPASDALAIEAIHTVNRYLSR
YiaY        PEIALVDPELTMSLPQKMTAASGIDALAHGIETFFSLRSRPASDALAVEAMATVSAYLRR
Adh_Gk      PEIALVDPKLTMSLPKKITAASGIDALAHGIETFFSLRSQPISDVLAIEAMTTVNRYLRR
Adh_Bsp     PDISIVDPKMTMTAPPAITAASGFDAHGAETFVSRASQPASDVLAFSAMSTVSKYLRR
Adh_BspL1   PDVSIIDPKLTLTAPPSITAAAGFDAFAHAARAFVSRISQPPSDALALSAMKTVHTYLRR
Adh_Pt      PEAAFVDPLAMVSAPPGITAASGIDALSHAVEAYVSRAASPVSDNLALGAVELIGGHLRQ
Adh_Dk      PEVAVVDPLLTMTAPPSVTAASGIDALSHAIETYVSLKAQPPARALALKAIELIGESLRT
Adh_Dt      PEVAVVDPILTLTAPPSVTAASGIDALSHAIETYVSLKAQPPARALALKAIELIGESLRA
                 *    : :**   :   *   :***:*:**:.*. *:::.*   :      *:. *:    :    *

Adh_Bp      AVRDGADMEARIGMSQGSVLAGMAFNNGFLGLAHAIGSALSGHCHVPHGVAIGLLLPHVV
Adh_Bk      SVANGEDKEARCGMSHGSLLAGMAFNNGFLGLAHAIGSALSGHCHVPHGVAIGLLLPHVV
Adh_Bt      AVHDGSDVEARIGMSHGSLLAGMAFTNGFLGLAHAIGSALSGHCHVPHGIAIGLLLPHVV
Adh_At      AVHNGSDMEARIGMSHGSLLAGMAFNNGFLGLAHAIGSALSGHCHVPHGVAIGLLLPKVV
YiaY        AVEDGTDKEARIGMSQGSLLAGMAFNNGFLGLAHAIGSALSGHCHVSHGVAIGLLLPKVV
Adh_Gk      AVEDGTNKEARIGMSYGSLLAGMAFNNGFLGLAHAIGSALSGHCHVSHGVAIGLLLPKVV
Adh_Bsp     AVYNGEDVEARIKMAEASLLAGMAFNQSYLGLTHAIGSALSGHAHVSHGVAIGLLLPGVI
Adh_BspL1   AVYNGDDIEARMKMAEASLLAGMAFNQSYLGLAHAIGSAISVHAHVSHGVVIGLLLPKVI
Adh_Pt      AVANGGDLAARTGAALGSLLAGMAFNNAFLGLTHSIGAALSGHVHVSHGVAVGLLLPYVM
Adh_Dk      AVADGSDKEARTRMSLGSLLAGMAFNNSLLGLTHSIGAALSGHAHVSHGMAIGLLLPYVM
Adh_Dt      AVADGSNKEARTKMSLGSLLAGMAFNNSLLGLTHSIGAALSGHAHVSHGMAVGLLLPYVM
                 :* :*  :  **     :.*:******.*. ***:*:**:*:* *  ** **::*****.*:

Adh_Bp      AFNTPVRPEKAELIADVLGSV--QKET----GTAAELVGQLVQDIGLPQRLQEVGVPEAK
Adh_Bk      EFNSSECPDQAAEIAKILGVK--AEDERQLAEQASHAVGDLVKDIGLPTRLRDMNVPEEK
Adh_Bt      AFNAPARPDKAAQLARLLGVE--ANPREERGEETSAAVARMVADIGLPTRLRDVGVPEEK
Adh_At      EFNATVRPDKAAKIAGLMGMK--GEHSEELALQASPAMARLVEDIGLPTRLREVDVTEKK
YiaY        EFNARVRPEKAAKIAELLGVK--GDREEVLAEQAAPAVASLVKEIGLPTRLRDVDVSEEK
Adh_Gk      EFNSVVQPEKAAKIAELLGRK--GNQNT-LVQQAALAVASLVKEIGLPTRLRDVDVPKEK
Adh_Bsp     RYNSISRMDKHIEMAGAFREIDRSLSDWEIIDQLIEDVSRLRDDIGLPQRLQQVGVKEDQ
```

TABLE 2-continued

YiaY amino acid sequence alignment

```
Adh_BspL1  EYNLVAKIDKYAEAGKYIEQSSHGLSNYEAAALFSETVTQLRNDIGLPKQLREVNVKRAQ
Adh_Pt     EYNLMAKPDKFARLARAMGEVTEGKSLYRAASLAPRAVKAMVKSIGLPVRLKEIGVPEGA
Adh_Dk     EFNAMARMEKFSKIAVALGEDVKGLSLREAALRSVKAVRELVEDISLPRRLGDVGVTGDM
Adh_Dt     EFNAMARLEKYGKIAIALGEDVKGLSLREAALRSVKAVRELVEDISLPRRLGEVGVTGDM
             :*        ::       . :           *    : .*.** :* :: *

Adh_Bp     LVDIAKDSFKSGMMKWNPRLPTEQEVLELLQKAF
Adh_Bk     LADIARDSFQSGMMKFNPRRASESEVLELLHRVY
Adh_Bt     LPAIAKDAFKSGMMTCNPRQPTEQEVRELLRRAF
Adh_At     LFEIAKDSFKSGMMKFNPRQPSESEVLQLLKEIF
YiaY       LPDIARDAFKSGMMKFNPRQPSLSEVLTLLQQIY
Adh_Gk     LPDIAKDSFKSGMMRFNPRQPSEAEVMTLLQQIY
Adh_Bsp    LKMIAADSVKSGMWKFNPRQASEEEILELLKELY
Adh_BspL1  LEAISKDSIKSGMWQFNPRRASEQDVYQMLREML
Adh_Pt     LAAIAETALKHGMIKFNPRVPSREDILDIVKKAY
Adh_Dk     IEGMAKDAMGHGMLKFNPRAVTEKDIIAILRKAL
Adh_Dt     IEGMAKDAMGHGMLKFNPRVVTEKDIMAILQKAL
             :  ::   :.  **    ***   :   :: ::: .
```

Adh_Bp = SEQ ID NO: 6 (*Brevibacillus panacihumi*); Adh_Bk = SEQ ID NO: 2 (*Bacillus kribbensis*); Adh_Bt = SEQ ID NO: 5 (*Brevibacillus thermoruber*); Adh_At = SEQ ID NO: 4 (*Aneurinibacillus terranovensis*); YiaY = SEQ ID NO: 1 (*Aeribacillus pallidus*); Adh_Gk = SEQ ID NO: 3 (*Geobacillus kaustophilus*); Adh_Bsp = SEQ ID NO: 7 (*Bacillus sp.* FJAT-14578); Adh_BspL1 = SEQ ID NO: 10 (*Bacillus sp.* L1(2012)); Adh_Pt = SEQ ID NO: 11 (*Pelotomaculum thermopropionicum*); Adh_Dk = SEQ ID NO: 8 (*Desulfotomaculum kuznetsovii*); and Adh_Dt = SEQ ID NO: 9 (*Desulfurispora thermophila*). Symbols below the alignment indicate: * = invariant positions; : = strongly conserved positions; . = less strongly conserved positions; no symbol indicated non-conserved positions.

TABLE 3

Amino acid sequence alignment (Clustal Omega) of *A. pallidus* MFS transporter (HMFCA transporter) with 10 best BLAST hits

```
Aeribacillus transporter                        MKNIANTSTERPVNDASVKNRQMVRATIASLIGWSLDLYDLFLLLFVATTIGNLFFPASN
gi|499548718|ref|WP_011229501.1|:1-445          MDNITKTNIERPVE-VSIKNSQMVRATIASLIGWALDLYDLFLLLYVATTIGNLFFPASN
gi|651977233|ref|WP_026691821.1|:7-435          -----------------NNRQLVSATMASLLGWSFDLYDLFILLYVTPTIGSLFFPSSN
gi|654945126|ref|WP_028395291.1|:1-445          MSNVVAT--HSKQESVTVSKREVRSAMVASLLGWSFDLYDLFLLLFVAPTISVLFFPTTN
gi|737333963|ref|WP_035316274.1|:3-438          --------SSNQPPKVEISRRQMVNASIASLLGWALDLFDLFVLLYVAPVIGKLFFPTEL
gi|558617199|gb|EST53422.1|:11-446              --------SSNQPPKVEISRRQMVNASIASLLGWALDLFDLFVLLYVAPVIGKLFFPTEL
gi|737314460|ref|WP_035297308.1|:18-449         ------------RPPAAVGRKQMITAVLASLLGWSLDLYDLFILLYVTPVLGKLFFPADN
gi|656061131|ref|WP_029098927.1|:18-449         ------------RPPAAVGRKQMITAVLASLLGWSLDLYDLFILLYVTPVLGKLFFPADN
gi|503166469|ref|WP_013401130.1|:2-445          SANMETPVQQASALAAAISRKQMIIAVMASLLGWSLDLYDLFILLYVAPELGKLFFPTDK
gi|505187461|ref|WP_015374563.1|:8-445          ------NVQQTSSLTVSISKKQMITAVTASLLGWSLDLYDLFILLYVAPELGKLFFPADK
gi|612120256|gb|EZP78263.1|:2-445               SVNTETTVQQASPLTVSISRKQMIIAVMSSLLGWSLDLYDLFILLYVAPELGKLFFPTDK
                                                          . ::    *    :**:**:;:**:***:**.*:     :.  ****:

Aeribacillus transporter                        QTLSLAAVYASFAVTLLMRPLGSAIFGIYADKNGRKKAMTVAIIGAGLCTAAFGLLPTIH
gi|499548718|ref|WP_011229501.1|:1-445          QTLSLAAVYASFAVTLLMRPLGSAIFGVYADKNGRKKAMTVAIIGAGLSTTAFGLLPTIH
gi|651977233|ref|WP_026691821.1|:7-435          PTLSLAAVYASFAVTLLMRPLGSAIFGSYADKNGRKKAMTVAIVGVGVSTAVFGLLPTVP
gi|654945126|ref|WP_028395291.1|:1-445          PTLSLAAVYASFAVTLLMRPLGSAIFGSYADKNGRKKAMIVSVVGVGVSTAAFGLLPTVP
gi|737333963|ref|WP_035316274.1|:3-438          PTLSLAAVYASFAVTLLMRPIGSALFGSYADRKGRKKAMIVAVIGVGVATALFGALPTVH
gi|558617199|gb|EST53422.1|:11-446              PTLSLAAVYASFAVTLLMRPIGSALFGSYADRKGRKKAMIVAVIGVGVATALFGALPTVH
gi|737314460|ref|WP_035297308.1|:18-449         PTLSLAAVYASFAVTLLLRPFGSALFGSYADRNGRKRAMVVAVSGVGISTALFGVLPTVA
gi|656061131|ref|WP_029098927.1|:18-449         PTLSLAAVYASFAVTLLLRPFGSALFGSYADRNGRKRAMVVAVSGVGISTALFGVLPTVA
gi|503166469|ref|WP_013401130.1|:2-445          PTLSLAAVYASFAVTLFMRPLGSLAFGAYADRNGRKRAMVVAVSGVGISTALFGALPTVA
gi|505187461|ref|WP_015374563.1|:8-445          PTLSLAAVYASFAVTLFMRPLGSALFGSYADRNGRKRAMVVAVSGVGISTALFGALPTVE
gi|612120256|gb|EZP78263.1|:2-445               PTLSLAAVYASFAVTLFMRPLGSALFGTYADRNGRKRAMVVAVSGVGISTALFGALPTVA
                                                ***************:;**.:**;**  ***.;:***:**  *::  .*:.*: ** ***:

Aeribacillus transporter                        QVGVVAAIAFLILRLVQGVFVGGVVASTHTIGTESASPKYRGFMSGLIGGGGAGLGALFA
gi|499548718|ref|WP_011229501.1|:1-445          QVGVAASIAFLILRLVQGIFVGGVVASTHTIGTESASPKYRGLMSGLIGGGGAGLGALFA
gi|651977233|ref|WP_026691821.1|:7-435          QIGVFATIIFLVLRLCQGIFVGGVVASSHTIGTESAPPKLRGLMSGLIGGGGAGLGALFA
gi|654945126|ref|WP_028395291.1|:1-445          QIGFMASIIFLVLRLCQGIFVGGVVASSHTIGTESAPPKWRGLMSGLIGGGGAGLGALFA
gi|737333963|ref|WP_035316274.1|:3-438          IQGVGASIIFLILRLVQGIFVGGVVASTHTIGTESVPPKWRGFMSGFVGGGGAGLGALLA
gi|558617199|gb|EST53422.1|:11-446              QIGVGASIIFLILRLVQGIFVGGVVASTHTIGTESVPPKWRGFMSGFVGGGGAGLGALLA
gi|737314460|ref|WP_035297308.1|:18-449         HIGAAATILFIILRLIQGVFVGGVVASTHTIGRESVPEKWRGLVGGGGAGLGALLA
gi|656061131|ref|WP_029098927.1|:18-449         HIGAAATILFIILRLIQGVFVGGVVASTHTIGTESVPEKWRGLMSGLVGGGGAGLGALLA
gi|503166469|ref|WP_013401130.1|:2-445          QIGAAAAIIFIILRLVQGVFVGGVVASTHTIGTESVPEKWRGLMSGLVGGGGAALGALLA
gi|505187461|ref|WP_015374563.1|:8-445          QIGAAAAIIFIILRLIQGVFVGGVVASTHTIGTESVPEKWRGLMSGLVGGGGAALGALLA
gi|612120256|gb|EZP78263.1|:2-445               QIGAAAAIFIVLRLVQGVFVGGVVASTHTIGTESVPEKWRGLMSGLVGGGGAALGALLA
                                                  :*  *:*  *:;***  **  *:*******.*******    *  **:***  ****.*

Aeribacillus transporter                        SISYSVVTAIFPGEAFDVWGWRVMFFTGIIGSLFGLFIFRSLEESPLWKQLKEENSKGEV
gi|499548718|ref|WP_011229501.1|:1-445          SIAYSIVSAIFPGDAFDTLGWRIMFFTGIIGALFGLFIFRSLDESPLWKQLKEKQSKDKM
```

TABLE 3-continued

Amino acid sequence alignment (Clustal Omega) of *A. pallidus* MFS transporter
(HMFCA transporter) with 10 best BLAST hits

```
gi|651977233|ref|WP_026691821.1|:7-435    SIAFTVVSSFFPGEAFSEWGWRVMFFTGILGAIAGLFVFRTLDESPLWKGLQEEKKGKAV
gi|654945126|ref|WP_028395291.1|:1-445    SIAFAIISALFPGEAFNEWGWRVLFFTGLLGAGAGLIVFRSLNESPLWAQLHEEKKKTNE
gi|737333963|ref|WP_035316274.1|:3-438    SIVYFIVSEAFPGEAFDAWGWRFMFFAGILSAVLGVFVFKSLEESPLWLQAQQKKE---A
gi|558617199|gb|EST53422.1|:11-446        SIVYFIVSEAFPGEAFDAWGWRFMFFAGILSAVLGVFVFKSLEESPLWLQAQQKKE---A
gi|737314460|ref|WP_035297308.1|:18-449   SIVYFVLSSLFPGEAFSEWGWRFMFFTGILCSVLGLFVFRMLEESPLWVQHKNEQA---A
gi|656061131|ref|WP_029098927.1|:18-449   SIVYFVLSSLFPGEAFSEWGWRFMFFTGILCSVLGLFVFRMLEESPLWVQHKNEQA---A
gi|503166469|ref|WP_013401130.1|:2-445    SIVYFVLSSVFSGPEFSEWGWRFMFFTGILSSVLGLFVFKKLEESPLWMQHKKKQE---T
gi|505187461|ref|WP_015374563.1|:8-445    SIVYFVLSSIFPGPEFSEWGWRFMFFTGILSSVLGLFVFKKLEESPGWVQHKKQVQ---T
gi|612120256|gb|EZP78263.1|:2-445         SIVYFVLSNIFSGSEFSEWGWRFMFFTGILCSVLGLFIFKKLEESPLWVQHKKDQE---M
                                          **  :  :::   *    *.  ***.:**:*:  :   *:::*: *:***:*    :: :

Aeribacillus transporter                  -SEFQKAPLKTFFTKYYKVLLVNLMIVIGGGSGYYLTSGFIPTFLKVVNKVSASVSSGVL
gi|499548718|ref|WP_011229501.1|:1-445    -VEQQKSPFKMFLTKYYKVLFVNLMIVIGGGSGYYLTAGFIPTFLKVVNKVPAAVSSGVL
gi|651977233|ref|WP_026691821.1|:7-435    SHTIEQKPVKTLFTTYSKVLLVNLMIVIGGGTGYYLTAGFIPTFLTIINDVSPGTKSGIL
gi|654945126|ref|WP_028395291.1|:1-445    EDAVPQSPIKMLFKQYPGVLLVNVMIVMGGGSAYYLTSGFVPTFLKVVNEAPPNVISGVL
gi|737333963|ref|WP_035316274.1|:3-438    AKKPEGSPVKMIFTQYRNVLLVNLMLVTGGGTAYYLTSGYLPTFLNVINKVSSGTASLIL
gi|558617199|gb|EST53422.1|:11-446        AKKPEGSPVKMIFTQYRNVLLVNLMLVTGGGTAYYLTSGYLPTFLNVINKVSSGTASLIL
gi|737314460|ref|WP_035297308.1|:18-449   KPAGGQSPVKMVFTKYLPVLLVNLLIVIGGGSAYYLTSGYLPTFLNVINHVPQTTASMIL
gi|656061131|ref|WP_029098927.1|:18-449   KPAGGQSPVKMVFTKYLPVLLVNLLIVIGGGSAYYLTSGYLPTFLNVINHVPQTTSSMIL
gi|503166469|ref|WP_013401130.1|:2-445    KPEYQQSPVKMVFTKYLSVLLVNLMIVIGGGSAYYLTCGYLPTFLKVINNIPQTVSSIIL
gi|505187461|ref|WP_015374563.1|:8-445    KPENEQSPVKIVFTKYLSVLLINLMIVIGGGSAYYLTCGYLPTFLKVINNIPQTVSSMIL
gi|612120256|gb|EZP78263.1|:2-445         KPENQQSPVKMVFSKYLSVLLINLMIVIGGGSAYYLTCGYLPTFLKVINNIPQTVSSMIL
                                            *.*  .:.  *  **::*::* ***:.****.*::****.::*.    . * :*

Aeribacillus transporter                  IATSIMTIVAAVLVGHLSEVIGRKKTFLLIGILCLVGLPYFYLSLANSTTTTGIYLNALG
gi|499548718|ref|WP_011229501.1|:1-445    IATSITTILAAIVVGHLSELIGRKKTFMIIGILCVFGLPYFYLSLAHSTTTTSIYLNAIG
gi|651977233|ref|WP_026691821.1|:7-435    IASSVVTIISALLVGHLSEIIGRKKTFLAIGVVNIIGLPFFYLSLADAATTPSIYFYTMC
gi|654945126|ref|WP_028395291.1|:1-445    IASSIVTIISALLFGHLSELIGRKKVFLLVGVLNIIGLPYFYLALGDSVTTLSIYLNTMG
gi|737333963|ref|WP_035316274.1|:3-438    MGASVSAIISAVLFGYLSDVIGRKKTFLLIGFINLILLPVLFIQLGSATSIPMITFYALA
gi|558617199|gb|EST53422.1|:11-446        MGASVSAIISAVLFGYLSDVIGRKKTFLLIGFINLILLPVLFIQLGSATSIPMITFYALA
gi|737314460|ref|WP_035297308.1|:18-449   AASSIAAIIASVALGHLSTVIGRKKTFVLLGILNLMALPYLYTELAAAQDLSRIALYAMG
gi|656061131|ref|WP_029098927.1|:18-449   AASSIAAIIASVVLGHLSTIIGRKKTFVLLGILNLMALPYLYTELAAAQDLSRIALYAMG
gi|503166469|ref|WP_013401130.1|:2-445    MVSSISMVAAVVLGHLSTIIGRKKTFILLGIVNFLALPYLYTELADAQDLTMITLYAMG
gi|505187461|ref|WP_015374563.1|:8-445    IVSSISAMIAAIALGHLSTIIGRKKTFILLGIVNLIALPYLYTELADAQDMTSITLYAMG
gi|612120256|gb|EZP78263.1|:2-445         MVSSISAMIASIVLGHLSTIIGRKKTFILLGTVNLIALPYLYTELAAAQDLTLIILYAMG
                                           :*: :::::: .*:** :*****.*:  :*  :.  **  ::  *   :   * : ::

Aeribacillus transporter                  LIFLGNAAYAPVLIFLNERFPTSIRSTGTGLSWNMGFAIGGMMPTFVNLASGTVEHIPYT
gi|499548718|ref|WP_011229501.1|:1-445    LVFLGNASYAPVLIFLNERFPTEVRSTGRGLSWNVGFAIGGMMPTFVNLASGTVEHIPYT
gi|651977233|ref|WP_026691821.1|:7-435    VVFLGNAAYAPVLIFLNERFPTSIRSTGTGISWNMGFAVGGMMPTFVTLASGSVKNIPHT
gi|654945126|ref|WP_028395291.1|:1-445    LAFLGNAAYAPVLIFLNERFPTVIRSTGTGLSWNMGFAIGGMMPTFVTLASGKVENIPTT
gi|737333963|ref|WP_035316274.1|:3-438    LAFLGNAAYAPILIFLNERFPTSIRSSGTGLSWNMGFAVGGMMPTFVTLASGTTENIPYS
gi|558617199|gb|EST53422.1|:11-446        LAFLGNAAYAPILIFLNERFPTSIRSSGTGLSWNMGFAVGGMMPTFVTLASGTTENIPYS
gi|737314460|ref|WP_035297308.1|:18-449   LAFLGNASYAPVLIFLNERFPTAIRSTGTGLSWNMGFAIGGMMPTGVTMASGQTSEIPFF
gi|656061131|ref|WP_029098927.1|:18-449   LAFLGNASYAPVLIFLNERFPTAIRSTGTGLSWNMGFAIGGMMPTFVTMASGQTSEIPFY
gi|503166469|ref|WP_013401130.1|:2-445    LAFLGNGSYAPVLIFLNERFPTSIRSTGTGLSWNMGFAVGGMMPTFVTMASRQTSDIPSS
gi|505187461|ref|WP_015374563.1|:8-445    LAFLGNASYAPVLIFLNERFPTTIRSTGTGLSWNMGFAVGGMMPTFVTMASSQTSDIPLS
gi|612120256|gb|EZP78263.1|:2-445         LAFLGNGSYAPVLIFLNERFPTAIRSTGTGLSWNMGFAVGGMMPTFVTMTSSQTSDIPLS
                                          : ****.:***.***********  :**.***:***:********.::*    ...**

Aeribacillus transporter                  LMYFTIGIYLVYILGSLIIPETKGNLK
gi|499548718|ref|WP_011229501.1|:1-445    LMYFTIVIYLVYILGSFIIPETKGNLK
gi|651977233|ref|WP_026691821.1|:7-435    LMYFFIGIFLLYLIGSAVIKETKGNLN
gi|654945126|ref|WP_028395291.1|:1-445    LMYPAIGIFLVYIIGSIIVPETKGNLK
gi|737333963|ref|WP_035316274.1|:3-438    LMGFSIAVFVVYVIGSLVIPETKGNFE
gi|558617199|gb|EST53422.1|:11-446        LMGFSIAVFVVYVIGSLVIPETKGNFE
gi|737314460|ref|WP_035297308.1|:18-449   LAYFSIGLFLLYLVGSLIIPETKGNFQ
gi|656061131|ref|WP_029098927.1|:18-449   LAYFSIGLFLLYLVGSLIIPETKGNFQ
gi|503166469|ref|WP_013401130.1|:2-445    LAYFFIALFLLYLLGSFIIPETKGNFK
gi|505187461|ref|WP_015374563.1|:8-445    LTYFSIALFLLYLLGSFIIPETKGNFK
gi|612120256|gb|EZP78263.1|:2-445         LAYFSIALFLLYLLGSFIIPETKGNFK
                                          *  *   ::::*::**  :  *****::
```

Symbols below the alignment indicate: * = invariant positions; : = strongly conserved positions; . = less
strongly conserved positions; no symbol indicated non-conserved positions.

The invention claimed is:

1. A microbial cell comprising an expression construct for expression of a nucleotide sequence encoding a dehydrogenase having an amino acid sequence with at least 81.65% identity with the amino acid sequence of SEQ ID NO: 1, wherein, the expression construct is expressible in the cell and expression of 5-hydroxymethyl-2-furancarboxylic acid (HMFCA) dehydrogenase confers to or increases in the cell the ability to oxidize HMFCA to 5- formyl-2-furoic acid (FFA), as compared to a corresponding wild type cell lacking the expression construct.

2. The cell according to claim 1, wherein the cell further comprises at least one of:
   (a) an aldehyde dehydrogenase activity that oxidizes furanic aldehydes to the corresponding furanic carboxylic acids, and,
   (b) the ability of transporting furanic compounds into and/or out of the cell.

3. The cell according to claim 2, further comprising a second expression construct for expression of a nucleotide sequence encoding an aldehyde dehydrogenase comprising an amino acid sequence with at least 70% identity with any one of the amino acid sequence of SEQ ID NO: 24, 25, 26, 27, 28, 29 and 30, wherein the second expression construct is expressible in the cell and expression of the aldehyde dehydrogenase confers to or increases in the cell at least one of the abilities of i) oxidizing 5-hydroxymethylfurfural (HMF) to HMFCA, ii) oxidizing 2,5-diformyl furan (DFF) to FFA, and iii) oxidizing FFA into 2,5-furandicarboxylic acid (FDCA), as compared to a corresponding wild type cell lacking the second expression construct.

4. The cell according to claim 2, further comprising a third expression construct for expression of a nucleotide sequence encoding a polypeptide having the ability to transport at least HMFCA into the cell, which polypeptide comprises an amino acid sequence with at least 55% identity with any one of the amino acid sequence SEQ ID NO's: 17, 31, 32, 33 and 34, wherein, the third expression construct is expressible in the cell and expression of the polypeptide confers to or increases in the cell the ability to transport at least HMFCA into the cell, as compared to a corresponding wild type cell lacking the third expression construct.

5. The cell according to claim 1, wherein the microbial cell is a yeast or filamentous fungal cell selected from a genus from the group consisting of *Candida, Hansenula, Kluyveromyces, Pichia, Saccharomyces, Schizosaccharomyces, Yarrowia, Acremonium, Agaricus, Aspergillus, Aureobasidium, Myceliophthora, Chrysosporium, Coprinus, Cryptococcus, Filibasidium, Fusarium, Humicola, Magnaporthe, Mucor, Myceliophthora, Neocallimastix, Neuro-* spora, Paecilomyces, Penicillium, Piromyces, Panerochaete, Pleurotus, Schizophyllum, Talaromyces, Thermoascus, Thielavia, Tolypocladium, and Trichoderma.

6. The cell according to claim 5, wherein the yeast or filamentous fungal cell is selected from a species from the group consisting of Kluyveromyces lactis, S. cerevisiae, Hansenula polymorpha, Yarrowia lipolytica, Pichia pastoris, Aspergillus niger, Aspergillus awamori, Aspergillus foetidus, Aspergillus sojae, Aspergillus fumigatus, Talaromyces emersonii, Aspergillus oryzae, Myceliophthora thermophila, Trichoderma reesei and Penicillium chrysogenum.

7. The cell according to claim 1, wherein the microbial cell is a bacterial cell selected from a genus from the group consisting of Escherichia, Anabaena, Aeribacillus, Aneurinibacillus, Burkholderia, Bradyrhizobium, Caulobacter, Cupriavidus, Desulfotomaculum, Desulfurispora, Gluconobacter, Rhodobacter, Pelotomaculum, Pseudomonas, Paracoccus, Bacillus, Geobacillus, Brevibacillus, Brevibacterium, Corynebacterium, Rhizobium (Sinorhizobium), Flavobacterium, Klebsiella, Enterobacter, Lactobacillus, Lactococcus, Methylobacterium, Ralstonia, Rhodopseudomonas, Staphylococcus and Streptomyces.

8. The cell according to claim 7, wherein the bacterial cell is selected from a species from the group consisting of A. pallidus, A. terranovensis, B. subtilis, B. amyloliquefaciens, B. coagulans, B. kribbensis, B. licheniformis, B. puntis, B. megaterium, B. halodurans, B. pumilus, B. thermoruber, B. panacihumi, C. basilensis, D. kuznetsovii, D. thermophila, G. kaustophilus, Gluconobacter oxydans, Caulobacter crescentus CB 15, Methylobacterium extorquens, Rhodobacter sphaeroides, Pelotomaculum thermopropionicum, Pseudomonas zeaxanthinifaciens, Pseudomonas putida, Paracoccus denitrificans, E. coli, C. glutamicum, Staphylococcus carnosus, Streptomyces lividans, Sinorhizobium melioti and Rhizobium radiobacter.

9. A nucleic acid vector molecule comprising at least one of:
    (a) a nucleotide sequence encoding the polypeptide having HMFCA dehydrogenase activity, which polypeptide comprises an amino acid sequence that has at least 81.65% sequence identity with the amino acid sequence of SEQ ID NO: 1;
    (b) a nucleotide sequence as set out in SEQ ID NO: 12 or 13;
    (c) a nucleotide sequence which is the reverse complement of the nucleotide sequence as defined in (a) or (b).

10. The cell according to claim 1, wherein the nucleotide sequence encodes a dehydrogenase having an amino acid sequence with at least 95% identity with the amino acid sequence of SEQ ID NO: 1.

11. A process for oxidizing 5-hydroxymethyl-2-furancarboxylic acid (HMFCA) to 5-formyl-2-furoic acid (FFA), the process comprising incubating the cell of claim 1 in the presence of HMFCA.

12. The process according to claim 11, wherein the incubating is under conditions conducive to the oxidation of HMFCA by the cell.

13. A process for producing FDCA, comprising incubating the cell of claim 1 in a medium comprising one or more furanic precursors of FDCA, and, optionally recovery of the FDCA.

14. The process according to claim 13, wherein the incubating is under conditions conducive to the oxidation of furanic precursors of FDCA by the cell to FDCA.

15. The process according to claim 13, wherein at least one furanic precursor of FDCA is selected from the group consisting of HMF, 2,5-dihydroxymethyl furan (DHF), HMFCA, FFA and 2,5-diformyl furan (DFF).

16. The process according to claim 15, wherein at least one furanic precursor of FDCA is HMF.

17. The process according to claim 13, wherein the furanic precursors of FDCA are obtained from one or more hexose sugars, optionally by acid-catalyzed dehydration.

18. The process according to claim 13, comprising recovering the FDCA from the medium by acid or salt precipitation followed by cooling crystallization and/or solvent extraction.

19. A process for producing a polymer from one or more FDCA monomers, comprising:
    (a) preparing a FDCA monomer in a process according to claim 13; and,
    (b) producing a polymer from the FDCA monomer obtained in (a).

20. A method of biotransformation of one or more furanic precursors to FDCA, comprising incubating the cell of claim 1 in the presence of one or more furanic precursors to FDCA.

21. The method according to claim 20, wherein at least one furanic precursor of FDCA is selected from the group consisting of HMF, DHF, HMFCA, FFA and DFF.

* * * * *

SEQUENCE LISTING

<160> NUMBER OF SEQ ID NOS: 40

<210> SEQ ID NO 1
<211> LENGTH: 392
<212> TYPE: PRT
<213> ORGANISM: Aeribacillus pallidus

<400> SEQUENCE: 1

Met Ile Gly Asn Tyr Ala Lys Lys Ala Ile Asp Phe Glu Phe Thr Phe
1               5                   10                  15

Tyr Leu Pro Thr Leu Ile Glu Phe Gly Tyr Gly Lys Ala Ser Arg Met
            20                  25                  30

Gly Glu Met Leu Glu Gln Met Gly Ile Lys Asn Val Phe Leu Val Thr
        35                  40                  45

Asp Lys Gly Val Glu Ala Ala Gly Leu Leu Ala Gly Ile Val Gln Ser
    50                  55                  60

Leu Glu Ser Ser Asn Ile Arg Tyr Val Ile Tyr Ser Asp Val Glu Pro
65                  70                  75                  80

Asp Pro Ser Leu Glu Thr Ile Asp Arg Gly Ala Ser Val Phe Lys Glu
                85                  90                  95

Gln Ser Phe Asp Cys Ile Leu Ala Val Gly Gly Gly Ser Pro Ile Asp
            100                 105                 110

Thr Ala Lys Gly Ile Arg Val Val Thr Asn Gly Gly Asn Ile Gly
        115                 120                 125

Asp Tyr Ala Gly Val Asn Arg Val Ala Lys Lys Ser Glu Ile Pro Leu
    130                 135                 140

Val Ala Val Pro Thr Thr Ser Gly Thr Gly Ser Glu Val Thr Ile Phe
145                 150                 155                 160

Gly Val Tyr Ser Asp Trp Glu Asn Gln Val Lys Val Thr Val Thr Ser
                165                 170                 175

Pro Tyr Met Ala Pro Glu Ile Ala Leu Val Asp Pro Glu Leu Thr Met
            180                 185                 190

Ser Leu Pro Gln Lys Met Thr Ala Ala Ser Gly Ile Asp Ala Leu Ala
        195                 200                 205

His Gly Ile Glu Thr Phe Phe Ser Leu Arg Ser Arg Pro Ala Ser Asp
    210                 215                 220

Ala Leu Ala Val Glu Ala Met Ala Thr Val Ser Ala Tyr Leu Arg Arg
225                 230                 235                 240

Ala Val Glu Asp Gly Thr Asp Lys Glu Ala Arg Ile Gly Met Ser Gln
                245                 250                 255

Gly Ser Leu Leu Ala Gly Met Ala Phe Asn Asn Gly Phe Leu Gly Leu
            260                 265                 270

Ala His Ala Ile Gly Ser Ala Leu Ser Gly His Cys His Val Ser His
        275                 280                 285

Gly Val Ala Ile Gly Leu Leu Pro Lys Val Glu Phe Asn Ala
    290                 295                 300

Arg Val Arg Pro Glu Lys Ala Ala Lys Ile Ala Glu Leu Leu Gly Val
305                 310                 315                 320

Lys Gly Asp Arg Glu Glu Val Leu Ala Glu Gln Ala Ala Pro Ala Val
                325                 330                 335

Ala Ser Leu Val Lys Glu Ile Gly Leu Pro Thr Arg Leu Arg Asp Val
            340                 345                 350

Asp Val Ser Glu Glu Lys Leu Pro Asp Ile Ala Arg Asp Ala Phe Lys
        355                 360                 365

Ser Gly Met Met Lys Phe Asn Pro Arg Gln Pro Ser Leu Ser Glu Val
370                 375                 380

Leu Thr Leu Leu Gln Gln Ile Tyr
385                 390

<210> SEQ ID NO 2
<211> LENGTH: 383
<212> TYPE: PRT
<213> ORGANISM: Bacillus kribbensis

<400> SEQUENCE: 2

Met Asp Val Glu Phe Ser Phe His Leu Pro Thr Leu Ile Glu Phe Gly
1               5                   10                  15

Phe Gly Lys Ala Ser Leu Leu Gly Glu Arg Leu Leu Lys Leu Gly Val
                20                  25                  30

Gly Asn Val Phe Leu Val Ser Asp Lys Gly Val Ala Ser Ala Gly Leu
            35                  40                  45

Leu Gln Lys Leu Glu Gln Ser Leu Gln Thr Ser Asp Ile His Phe Lys
        50                  55                  60

Thr Tyr Leu Glu Val Glu Pro Asp Pro Ser Leu Glu Thr Ile Asp Leu
65                  70                  75                  80

Gly Ala Glu Ala Phe Asn Ser Gly Lys Tyr Asp Cys Ile Val Ala Val
                85                  90                  95

Gly Gly Gly Ser Ala Ile Asp Thr Ala Lys Gly Ile Arg Val Val Ala
            100                 105                 110

Gly Asn Gly Gly Ser Ile Gly Asp Phe Ala Gly Val Asp Lys Ile Gly
        115                 120                 125

Lys Ala Pro Gln Ile Pro Leu Ile Ala Val Pro Thr Thr Ser Gly Thr
130                 135                 140

Gly Ser Glu Val Thr Ile Phe Gly Val Tyr Ser Asp Trp Val Lys Asn
145                 150                 155                 160

Val Lys Val Thr Val Thr Ser Gln Tyr Met Ala Pro Thr Ile Ala Leu
                165                 170                 175

Val Asp Pro Glu Leu Thr Met Arg Leu Pro Arg Lys Met Thr Ala Ala
            180                 185                 190

Ser Gly Ile Asp Ala Leu Ala His Gly Ile Glu Ser Tyr Phe Ser Leu
        195                 200                 205

Arg Ser Thr Ser Ala Ser Arg Ala Leu Ser Leu Glu Ala Ile Asn Ile
210                 215                 220

Val Gly Asn His Leu Arg Gln Ser Val Ala Asn Gly Glu Asp Lys Glu
225                 230                 235                 240

Ala Arg Cys Gly Met Ser His Gly Ser Leu Leu Ala Gly Met Ala Phe
                245                 250                 255

Asn Asn Gly Phe Leu Gly Leu Ala His Ala Ile Gly Ser Ala Leu Ser
            260                 265                 270

Gly His Cys His Val Pro His Gly Val Ala Ile Gly Leu Leu Leu Pro
        275                 280                 285

His Val Val Glu Phe Asn Ser Ser Glu Cys Pro Asp Gln Ala Ala Glu
290                 295                 300

Ile Ala Lys Ile Leu Gly Val Lys Ala Glu Asp Glu Arg Gln Leu Ala
305                 310                 315                 320

Glu Gln Ala Ser His Ala Val Gly Asp Leu Val Lys Asp Ile Gly Leu
                325                 330                 335

Pro Thr Arg Leu Arg Asp Met Asn Val Pro Glu Glu Lys Leu Ala Asp
            340                 345                 350

Ile Ala Arg Asp Ser Phe Gln Ser Gly Met Met Lys Phe Asn Pro Arg
355                 360                 365

Arg Ala Ser Glu Ser Glu Val Leu Glu Leu Leu His Arg Val Tyr
370                 375                 380

<210> SEQ ID NO 3
<211> LENGTH: 391
<212> TYPE: PRT
<213> ORGANISM: Geobacillus kaustophilus

<400> SEQUENCE: 3

Met Val Gly His Tyr Ile Gln Lys Glu Val Glu Phe Glu Phe Ser Phe
1               5                   10                  15

His Leu Pro Thr Ser Ile Gln Phe Gly Tyr Gly Lys Ala Ser Gln Leu
            20                  25                  30

Gly Asn Gln Leu Val Asp Met Gly Ile Lys Ser Ala Phe Leu Val Thr
        35                  40                  45

Asp Arg Gly Val Glu Ala Thr Gly Leu Leu Ala Gly Ile Ile Gln Ser
    50                  55                  60

Leu Glu Ser Ser Asn Ile Gln Tyr Cys Val Tyr Ala Asp Val Glu Pro
65                  70                  75                  80

Asp Pro Ser Leu Glu Thr Ile Asp Gln Gly Ala Ala Phe Lys Glu
                85                  90                  95

Gln Pro Phe Asp Cys Ile Val Ala Ile Gly Gly Gly Ser Pro Ile Asp
            100                 105                 110

Thr Ala Lys Gly Ile Arg Val Val Ala Thr Asn Gly Gly Ser Ile Gly
        115                 120                 125

Asp Tyr Ala Gly Val Asn Arg Ile Lys Lys Ser Glu Ile Pro Leu
    130                 135                 140

Ile Ala Leu Pro Thr Thr Ser Gly Thr Gly Ser Glu Val Thr Ile Phe
145                 150                 155                 160

Gly Val Tyr Ser Asp Trp Lys Asn Asn Val Lys Val Thr Val Thr Ser
                165                 170                 175

Pro Tyr Met Ala Pro Glu Ile Ala Leu Val Asp Pro Lys Leu Thr Met
            180                 185                 190

Ser Leu Pro Lys Lys Ile Thr Ala Ala Ser Gly Ile Asp Ala Leu Ala
        195                 200                 205

His Gly Ile Glu Thr Phe Phe Ser Leu Arg Ser Gln Pro Ile Ser Asp
    210                 215                 220

Val Leu Ala Ile Glu Ala Met Thr Thr Val Asn Arg Tyr Leu Arg Arg
225                 230                 235                 240

Ala Val Glu Asp Gly Thr Asn Lys Glu Ala Arg Ile Gly Met Ser Tyr
                245                 250                 255

Gly Ser Leu Leu Ala Gly Met Ala Phe Asn Asn Gly Phe Leu Gly Leu
            260                 265                 270

Ala His Ala Ile Gly Ser Ala Leu Ser Gly His Cys His Val Ser His
        275                 280                 285

Gly Val Ala Ile Gly Leu Leu Leu Pro Lys Val Val Glu Phe Asn Ser
    290                 295                 300

Val Val Gln Pro Glu Lys Ala Lys Ile Ala Glu Leu Leu Gly Arg
305                 310                 315                 320

Lys Gly Asn Gln Asn Thr Leu Val Gln Gln Ala Ala Leu Ala Val Ala
                325                 330                 335

Ser Leu Val Lys Glu Ile Gly Leu Pro Thr Arg Leu Arg Asp Val Asp
            340                 345                 350

```
Val Pro Lys Glu Lys Leu Pro Asp Ile Ala Lys Asp Ser Phe Lys Ser
        355                 360                 365

Gly Met Met Arg Phe Asn Pro Arg Gln Pro Ser Glu Ala Glu Val Met
        370                 375                 380

Thr Leu Leu Gln Gln Ile Tyr
385                 390

<210> SEQ ID NO 4
<211> LENGTH: 390
<212> TYPE: PRT
<213> ORGANISM: Aneurinibacillus terranovensis

<400> SEQUENCE: 4

Met

```
                        325                 330                 335
Leu Val Glu Asp Ile Gly Leu Pro Thr Arg Leu Arg Glu Val Asp Val
                340                 345                 350
Thr Glu Lys Lys Leu Phe Glu Ile Ala Lys Asp Ser Phe Lys Ser Gly
            355                 360                 365
Met Met Lys Phe Asn Pro Arg Gln Pro Ser Glu Ser Glu Val Leu Gln
        370                 375                 380
Leu Leu Lys Glu Ile Phe
385                 390

<210> SEQ ID NO 5
<211> LENGTH: 390
<212> TYPE: PRT
<213> ORGANISM: Brevibacillus thermoruber

<400> SEQUENCE: 5

Met Ser Gln Thr Val Gln Gly Thr Asp Phe Ala Phe Ser Phe His Leu
1               5                   10                  15
Pro Thr Leu Ile Glu Phe Gly Tyr Gly Arg Ala Ser Arg Leu Gly Glu
                20                  25                  30
Arg Leu Gln His Leu Gly Val Thr Asn Val Phe Val Thr Asp Lys
            35                  40                  45
Gly Val Glu Ala Ala Gly Leu Leu Asn Gly Leu Val Gly Ser Leu Gln
    50                  55                  60
Ser Ala Gly Ile Ala Phe Asp Leu Tyr Thr Glu Val Glu Pro Asp Pro
65                  70                  75                  80
Gly Leu Glu Thr Ile Asp Arg Gly Ala Ala Val Phe Arg Ala Lys Pro
                85                  90                  95
Tyr Asp Cys Leu Val Ala Val Gly Gly Gly Ser Pro Ile Asp Ala Ala
            100                 105                 110
Lys Gly Met Arg Val Val Thr Ser Cys Gly Gly Ser Ile Ala Asp Tyr
        115                 120                 125
Ala Gly Val Asn Arg Val Pro Met Ala Pro Ala Val Pro Leu Val Ala
    130                 135                 140
Val Pro Thr Thr Ser Gly Thr Gly Ser Glu Val Thr Met Phe Gly Val
145                 150                 155                 160
Tyr Ser Asp Trp His Asn His Val Lys Val Thr Val Thr Ser Pro His
                165                 170                 175
Met Ala Pro Thr Ile Ala Leu Val Asp Pro Ala Leu Thr Val Ser Leu
            180                 185                 190
Pro Ala Lys Met Thr Ala Ala Ser Gly Ile Asp Ala Leu Ala His Gly
        195                 200                 205
Ile Glu Thr Phe Phe Ser Val Arg Ser Arg Pro Ala Ser Asp Ala Leu
    210                 215                 220
Ala Met Glu Ala Ile Ala Ala Val Asn Ala His Leu Arg Arg Ala Val
225                 230                 235                 240
His Asp Gly Ser Asp Val Glu Ala Arg Ile Gly Met Ser His Gly Ser
                245                 250                 255
Leu Leu Ala Gly Met Ala Phe Thr Asn Gly Phe Leu Gly Leu Ala His
            260                 265                 270
Ala Ile Gly Ser Ala Leu Ser Gly His Cys His Val Pro His Gly Ile
        275                 280                 285
Ala Ile Gly Leu Leu Leu Pro His Val Val Ala Phe Asn Ala Pro Ala
    290                 295                 300
```

```
Arg Pro Asp Lys Ala Ala Gln Leu Ala Arg Leu Leu Gly Val Glu Ala
305                 310                 315                 320

Asn Pro Arg Glu Glu Arg Gly Glu Glu Thr Ser Ala Ala Val Ala Arg
            325                 330                 335

Met Val Ala Asp Ile Gly Leu Pro Thr Arg Leu Arg Asp Val Gly Val
                340                 345                 350

Pro Glu Glu Lys Leu Pro Ala Ile Ala Lys Asp Ala Phe Lys Ser Gly
        355                 360                 365

Met Met Thr Cys Asn Pro Arg Gln Pro Thr Glu Gln Glu Val Arg Glu
370                 375                 380

Leu Leu Arg Arg Ala Phe
385                 390

<210> SEQ ID NO 6
<211> LENGTH: 379
<212> TYPE: PRT
<213> ORGANISM: Brevibacillus panacihumi

<400> SEQUENCE: 6

Met Glu Ser Pro Phe Ser Phe His Leu Pro Thr Asn Val Gln Phe Gly
1               5                   10                  15

Val Gly Ser Ala Ser Arg Leu Gly Glu Met Leu Leu Ser Met Gly Val
                20                  25                  30

Arg Arg Val Phe Leu Val Thr Asp Gln Gly Val Arg Gln Ala Gly Leu
            35                  40                  45

Leu Asp Glu Val Ile His Ser Leu Glu Glu Lys Gly Leu His Phe Gln
    50                  55                  60

Ile Tyr Ala Asp Val Glu Pro Asp Pro Ser Leu Glu Thr Ile Gln Ala
65                  70                  75                  80

Gly Ala Ala Met Phe Gln Gln Gln Ser Phe Asp Cys Met Val Ala Ile
                85                  90                  95

Gly Gly Gly Ser Pro Ile Asp Thr Ala Lys Gly Ile Arg Val Leu Ala
                100                 105                 110

Ala Asn Gly Gly Gly Ile Gly Gln Tyr Ala Gly Val Asn Arg Val Pro
            115                 120                 125

Ala Ala Ser Ala Ile Pro Leu Ile Ala Ile Pro Thr Thr Ser Gly Thr
    130                 135                 140

Gly Ser Glu Val Thr Ile Phe Gly Val Tyr Ser Asp Trp Glu Asn His
145                 150                 155                 160

Val Lys Ile Thr Val Thr Ser Pro His Met Ala Pro Ser Thr Ala Leu
                165                 170                 175

Ile Asp Pro Ala Leu Thr Leu Ser Leu Pro Ala Lys Met Thr Ala Ala
            180                 185                 190

Thr Gly Ile Asp Ala Leu Ala His Gly Ile Glu Thr Phe Phe Ser Leu
    195                 200                 205

Arg Ser Ser Pro Ala Ser Asp Ala Leu Ala Ile His Ala Met Lys Met
210                 215                 220

Ile Ala Pro His Leu Arg Arg Ala Val Arg Asp Gly Ala Asp Met Glu
225                 230                 235                 240

Ala Arg Ile Gly Met Ser Gln Gly Ser Val Leu Ala Gly Met Ala Phe
                245                 250                 255

Asn Asn Gly Phe Leu Gly Leu Ala His Ala Ile Gly Ser Ala Leu Ser
            260                 265                 270

Gly His Cys His Val Pro His Gly Val Ala Ile Gly Leu Leu Leu Pro
    275                 280                 285
```

His Val Val Ala Phe Asn Thr Pro Val Arg Pro Glu Lys Ala Glu Leu
            290                 295                 300

Ile Ala Asp Val Leu Gly Ser Val Gln Lys Glu Thr Gly Thr Ala Ala
305                 310                 315                 320

Glu Leu Val Gly Gln Leu Val Gln Asp Ile Gly Leu Pro Gln Arg Leu
                325                 330                 335

Gln Glu Val Gly Val Pro Glu Ala Lys Leu Val Asp Ile Ala Lys Asp
            340                 345                 350

Ser Phe Lys Ser Gly Met Met Lys Trp Asn Pro Arg Leu Pro Thr Glu
            355                 360                 365

Gln Glu Val Leu Glu Leu Leu Gln Lys Ala Phe
            370                 375

<210> SEQ ID NO 7
<211> LENGTH: 383
<212> TYPE: PRT
<213> ORGANISM: Bacillus sp. FJAT-14578

<400> SEQUENCE: 7

Met Tyr Pro Ser Phe Glu Phe His Leu Pro Thr Lys Ile His Phe Gly
1               5                   10                  15

Tyr Asn Thr Ile Lys Gln Leu Asp His Leu Pro Phe Glu Ile Lys Arg
            20                  25                  30

Ala Phe Ile Val Thr Asp Gln Gly Val Leu Asn Ser Gly Leu Val Glu
        35                  40                  45

Asn Val Thr Asn Ile Leu Lys Asp His Gln Ile Ser Tyr Val Ile Tyr
50                  55                  60

Ser Glu Val Glu Pro Asp Pro Ser Val Glu Thr Val Asp Lys Ala Ala
65                  70                  75                  80

Gln Met Phe Gln Arg Glu Glu Ala Asp Ala Leu Ile Ala Ile Gly Gly
                85                  90                  95

Gly Ser Pro Ile Asp Thr Ala Lys Gly Val Arg Val Ile Ala Gly Asn
            100                 105                 110

Gly Gly Ser Ile Arg Asp Tyr Ala Gly Val Asn Leu Ile Lys Gln Lys
        115                 120                 125

Ser Asn Ile Pro Leu Ile Ala Ile Pro Thr Thr Ser Gly Thr Gly Ser
130                 135                 140

Glu Val Thr Ile Phe Ala Val Phe Ser Asp Trp Glu Glu Asn Arg Lys
145                 150                 155                 160

Val Thr Val Thr Ser Pro Phe Leu Ala Pro Asp Ile Ser Ile Val Asp
                165                 170                 175

Pro Lys Met Thr Met Thr Ala Pro Pro Ala Ile Thr Ala Ala Ser Gly
            180                 185                 190

Phe Asp Ala Phe Ala His Gly Ala Glu Thr Phe Val Ser Arg Ala Ser
        195                 200                 205

Gln Pro Ala Ser Asp Val Leu Ala Phe Ser Ala Met Ser Thr Val Ser
    210                 215                 220

Lys Tyr Leu Arg Arg Ala Val Tyr Asn Gly Glu Asp Val Glu Ala Arg
225                 230                 235                 240

Ile Lys Met Ala Glu Ala Ser Leu Leu Ala Gly Met Ala Phe Asn Gln
                245                 250                 255

Ser Tyr Leu Gly Leu Thr His Ala Ile Gly Ser Ala Leu Ser Gly His
            260                 265                 270

Ala His Val Ser His Gly Val Ala Ile Gly Leu Leu Leu Pro Gly Val 275                 280                 285
Ile Arg Tyr Asn Ser Ile Ser Arg Met Asp Lys His Ile Glu Met Ala
    290                 295                 300

Gly Ala Phe Arg Glu Ile Asp Arg Ser Leu Ser Asp Trp Glu Ile Ile
305                 310                 315                 320

Asp Gln Leu Ile Glu Asp Val Ser Arg Leu Arg Asp Asp Ile Gly Leu
                325                 330                 335

Pro Gln Arg Leu Gln Gln Val Gly Val Lys Glu Asp Gln Leu Lys Met
            340                 345                 350

Ile Ala Ala Asp Ser Val Lys Ser Gly Met Trp Lys Phe Asn Pro Arg
        355                 360                 365

Gln Ala Ser Glu Glu Glu Ile Leu Glu Leu Leu Lys Glu Leu Tyr
    370                 375                 380

<210> SEQ ID NO 8
<211> LENGTH: 384
<212> TYPE: PRT
<213> ORGANISM: Desulfotomaculum kuznetsovii

<400> SEQUENCE: 8

Met Glu Ala Phe Thr Phe Gln Leu Lys Thr Thr Val Cys Phe Gly Ala
1               5                   10                  15

Asn Val Val Ser Gly Ile Val Asp Trp Cys Arg Asn Tyr Asn Ala Lys
            20                  25                  30

Arg Val Leu Ile Val Thr Asp Gln Gly Val Arg Lys Ala Gly Ile Leu
        35                  40                  45

Glu Lys Val Glu Lys Ile Leu Ser Asp Ala Gly Ile Glu Asn Val Val
    50                  55                  60

Phe Asp Asp Val Glu Pro Asp Pro Gly Leu Glu Thr Ile His Arg Cys
65                  70                  75                  80

Ala Ser Cys Phe Arg Glu Asn Lys Cys Asp Leu Ile Leu Ala Val Gly
                85                  90                  95

Gly Gly Ser Pro Ile Asp Thr Ala Lys Gly Ala Arg Val Ile Val Glu
            100                 105                 110

Asn Gly Gly His Ile Arg Asp Tyr Ala Gly Val Asn Lys Val Pro Arg
        115                 120                 125

Ala Pro Val Thr Pro Leu Ile Ala Ile Pro Thr Thr Ser Gly Thr Gly
    130                 135                 140

Ser Glu Val Thr Thr Phe Ala Val Leu Ser Asp Trp Glu Asn Arg Met
145                 150                 155                 160

Lys Ile Thr Ile Ser Ser Pro Phe Leu Ala Pro Glu Val Ala Val Val
                165                 170                 175

Asp Pro Leu Leu Thr Met Thr Ala Pro Pro Ser Val Thr Ala Ala Ser
            180                 185                 190

Gly Ile Asp Ala Leu Ser His Ala Ile Glu Thr Tyr Val Ser Leu Lys
        195                 200                 205

Ala Gln Pro Pro Ala Glu Ala Leu Ala Leu Lys Ala Ile Glu Leu Ile
    210                 215                 220

Gly Glu Ser Leu Arg Thr Ala Val Ala Asp Gly Ser Asp Lys Glu Ala
225                 230                 235                 240

Arg Thr Arg Met Ser Leu Gly Ser Leu Leu Ala Gly Met Ala Phe Asn
                245                 250                 255

Asn Ser Leu Leu Gly Leu Thr His Ser Ile Gly Ala Ala Leu Ser Gly
            260                 265                 270

```
His Ala His Val Ser His Gly Met Ala Ile Gly Leu Leu Leu Pro Tyr
            275                 280                 285

Val Met Glu Phe Asn Ala Met Ala Arg Met Glu Lys Phe Ser Lys Ile
290                 295                 300

Ala Val Ala Leu Gly Glu Asp Val Lys Gly Leu Ser Leu Arg Glu Ala
305                 310                 315                 320

Ala Leu Arg Ser Val Lys Ala Val Arg Glu Leu Val Glu Asp Ile Ser
                325                 330                 335

Leu Pro Arg Arg Leu Gly Asp Val Gly Val Thr Gly Asp Met Ile Glu
            340                 345                 350

Gly Met Ala Lys Asp Ala Met Gly His Gly Met Leu Lys Phe Asn Pro
            355                 360                 365

Arg Ala Val Thr Glu Lys Asp Ile Ile Ala Ile Leu Arg Lys Ala Leu
            370                 375                 380

<210> SEQ ID NO 9
<211> LENGTH: 377
<212> TYPE: PRT
<213> ORGANISM: Desulfurispora thermophila

<400> SEQUENCE: 9

Met Lys Thr Thr Val Cys Phe Gly Ala Asn Ile Val Ser Ser Ile Asp
1               5                   10                  15

Asp Arg Cys Arg Asp Tyr Asn Ala Arg His Val Leu Ile Val Thr Asp
            20                  25                  30

Gln Gly Val Glu Lys Ala Gly Ile Leu Glu Lys Val Glu Lys Val Leu
        35                  40                  45

Ser Asp Ala Gly Ile Glu Asn Val Val Phe Asp Val Glu Pro Asp
50                  55                  60

Pro Gly Leu Glu Thr Ile His Arg Cys Ala Ser Cys Phe Arg Glu Asn
65                  70                  75                  80

Lys Cys Asp Leu Phe Leu Ala Ile Gly Gly Gly Ser Pro Ile Asp Thr
                85                  90                  95

Ala Lys Gly Ala Arg Ile Ile Val Asp Asn Gly Gly His Ile Arg Asp
            100                 105                 110

Tyr Ala Gly Val Asn Lys Val Pro Arg Ala Pro Arg Thr Pro Leu Leu
        115                 120                 125

Ala Ile Pro Thr Thr Ser Gly Thr Gly Ser Glu Val Thr Thr Phe Ala
    130                 135                 140

Val Leu Ser Asp Trp Glu Asn Arg Met Lys Ile Thr Ile Ser Ser Pro
145                 150                 155                 160

Phe Leu Ala Pro Glu Val Ala Val Asp Pro Ile Leu Thr Leu Thr
                165                 170                 175

Ala Pro Pro Ser Val Thr Ala Ala Ser Gly Ile Asp Ala Leu Ser His
            180                 185                 190

Ala Ile Glu Thr Tyr Val Ser Leu Lys Ala Gln Pro Pro Ala Glu Ala
        195                 200                 205

Leu Ala Leu Lys Ala Ile Glu Leu Ile Gly Glu Ser Leu Arg Ala Ala
    210                 215                 220

Val Ala Asp Gly Ser Asn Lys Glu Ala Arg Thr Lys Met Ser Leu Gly
225                 230                 235                 240

Ser Leu Leu Ala Gly Met Ala Phe Asn Asn Ser Leu Leu Gly Leu Thr
                245                 250                 255

His Ser Ile Gly Ala Ala Leu Ser Gly His Ala His Val Ser His Gly
            260                 265                 270
```

```
Met Ala Val Gly Leu Leu Pro Tyr Val Met Glu Phe Asn Ala Met
            275                 280                 285

Ala Arg Leu Glu Lys Tyr Gly Lys Ile Ala Ile Ala Leu Gly Glu Asp
        290                 295                 300

Val Lys Gly Leu Ser Leu Arg Glu Ala Ala Leu Arg Ser Val Lys Ala
305                 310                 315                 320

Val Arg Glu Leu Val Glu Asp Ile Ser Leu Pro Arg Arg Leu Gly Glu
                325                 330                 335

Val Gly Val Thr Gly Asp Met Ile Glu Gly Met Ala Lys Asp Ala Met
                340                 345                 350

Gly His Gly Met Leu Lys Phe Asn Pro Arg Val Val Thr Glu Lys Asp
            355                 360                 365

Ile Met Ala Ile Leu Gln Lys Ala Leu
            370                 375

<210> SEQ ID NO 10
<211> LENGTH: 383
<212> TYPE: PRT
<213> ORGANISM: Bacillus sp. L1(2012)

<400> SEQUENCE: 10

Met Tyr Thr Ser Phe Asn Phe His Leu Pro Thr Arg Ile Gln Phe Gly
1               5                   10                  15

Tyr Glu Lys Val Lys Glu Leu Lys Asn Leu Pro Phe Gln Ala Asn Arg
            20                  25                  30

Ala Phe Ile Val Thr Asp Lys Gly Val Glu Lys Ala Gly Leu Leu Asn
        35                  40                  45

Asp Val Ile Asp Ala Ile Lys Gln Ala Asn Met Thr Tyr Lys Ile Tyr
    50                  55                  60

Arg Asp Val Glu Pro Asp Pro Ser Val Glu Thr Val Asp Lys Ala Ala
65                  70                  75                  80

Lys Ala Phe Ala Glu Ala Glu Cys Asp Leu Leu Ile Ala Val Gly Gly
                85                  90                  95

Gly Ser Pro Ile Asp Thr Ala Lys Gly Val Arg Val Val Ala Ser Asn
            100                 105                 110

Gly Gly Ser Ile Arg Asn Tyr Ser Gly Val Asn Leu Val Lys Glu Ala
        115                 120                 125

Pro Ser Val Pro Leu Val Ala Ile Pro Thr Thr Ala Gly Thr Gly Ser
    130                 135                 140

Glu Val Thr Ile Phe Ala Val Phe Ser Asp Asp Lys Glu Asn Arg Lys
145                 150                 155                 160

Val Thr Val Thr Ser Ser His Leu Ser Pro Asp Val Ser Ile Ile Asp
                165                 170                 175

Pro Lys Leu Thr Leu Thr Ala Pro Pro Ser Ile Thr Ala Ala Ala Gly
            180                 185                 190

Phe Asp Ala Phe Ala His Ala Ala Glu Ala Phe Val Ser Arg Ile Ser
        195                 200                 205

Gln Pro Pro Ser Asp Ala Leu Ala Leu Ser Ala Met Lys Thr Val His
    210                 215                 220

Thr Tyr Leu Arg Arg Ala Val Tyr Asn Gly Asp Asp Ile Glu Ala Arg
225                 230                 235                 240

Met Lys Met Ala Glu Ala Ser Leu Leu Ala Gly Met Ala Phe Asn Gln
                245                 250                 255

Ser Tyr Leu Gly Leu Ala His Ala Ile Gly Ser Ala Ile Ser Val His
```

```
            260                 265                 270
Ala His Val Ser His Gly Val Val Ile Gly Leu Leu Leu Pro Lys Val
                275                 280                 285
Ile Glu Tyr Asn Leu Val Ala Lys Ile Asp Lys Tyr Ala Glu Ala Gly
                290                 295                 300
Lys Tyr Ile Glu Gln Ser Ser His Gly Leu Ser Asn Tyr Glu Ala Ala
305                 310                 315                 320
Ala Leu Phe Ser Glu Thr Val Thr Gln Leu Arg Asn Asp Ile Gly Leu
                325                 330                 335
Pro Lys Gln Leu Arg Glu Val Asn Val Lys Glu Ala Gln Leu Glu Ala
                340                 345                 350
Ile Ser Lys Asp Ser Ile Lys Ser Gly Met Trp Gln Phe Asn Pro Arg
                355                 360                 365
Arg Ala Ser Glu Gln Asp Val Tyr Gln Met Leu Arg Glu Met Leu
                370                 375                 380

<210> SEQ ID NO 11
<211> LENGTH: 387
<212> TYPE: PRT
<213> ORGANISM: Pelotomaculum thermopropionicum

<400> SEQUENCE: 11

Met Ala Asp Tyr Asn Phe Ser Phe Ala Val Arg Thr Lys Val Phe Phe
1               5                   10                  15
Gly Arg Gly Val Val Phe Glu Gln Leu Pro Gly Ala Val Arg Glu Met
                20                  25                  30
Gly Cys Lys Lys Ala Val Leu Val Ser Asp Pro Gly Ile Val Gly Thr
            35                  40                  45
Gly Leu Ala Asp Arg Val Lys Asp Leu Leu Ala Gly Gly Val Ala
        50                  55                  60
Val Glu Val Phe Ser Glu Val Glu Pro Asp Pro Gly Leu Glu Thr Val
65                  70                  75                  80
His Lys Ala Ala Ala Phe Leu Gly Arg Thr Arg Pro Asp Cys Leu Val
                85                  90                  95
Ala Leu Gly Gly Gly Ser Ser Ile Asp Val Ala Lys Gly Ala Arg Val
                100                 105                 110
Ile Tyr Asp Asn Gly Gly Lys Ile Ser Asp Tyr Ala Gly Val Asn Lys
            115                 120                 125
Val Lys Val Lys Pro Ser Leu Pro Leu Met Ala Val Pro Thr Thr Ala
130                 135                 140
Gly Thr Gly Ser Glu Val Thr Val Phe Ala Val Leu Ser Asp Trp Glu
145                 150                 155                 160
Gln Asn Ile Lys Ile Thr Val Thr Ser Glu Tyr Leu Ala Pro Glu Ala
                165                 170                 175
Ala Phe Val Asp Pro Leu Ala Met Val Ser Ala Pro Gly Ile Thr
                180                 185                 190
Ala Ala Ser Gly Ile Asp Ala Leu Ser His Ala Val Glu Ala Tyr Val
            195                 200                 205
Ser Arg Ala Ala Ser Pro Val Ser Asp Asn Leu Ala Leu Gly Ala Val
        210                 215                 220
Glu Leu Ile Gly Gly His Leu Arg Gln Ala Val Ala Asn Gly Asp
225                 230                 235                 240
Leu Ala Ala Arg Thr Gly Ala Leu Gly Ser Leu Leu Ala Gly Met
                245                 250                 255
```

```
Ala Phe Asn Asn Ala Phe Leu Gly Leu Thr His Ser Ile Gly Ala Ala
            260                 265                 270

Leu Ser Gly His Val His Val Ser His Gly Val Ala Val Gly Leu Leu
        275                 280                 285

Leu Pro Tyr Val Met Glu Tyr Asn Leu Met Ala Lys Pro Asp Lys Phe
    290                 295                 300

Ala Arg Leu Ala Arg Ala Met Gly Glu Val Thr Glu Gly Lys Ser Leu
305                 310                 315                 320

Tyr Arg Ala Ala Ser Leu Ala Pro Arg Ala Val Lys Ala Met Val Lys
                325                 330                 335

Ser Ile Gly Leu Pro Val Arg Leu Lys Glu Ile Gly Val Pro Glu Gly
            340                 345                 350

Ala Leu Ala Ala Ile Ala Glu Thr Ala Leu Lys His Gly Met Ile Lys
        355                 360                 365

Phe Asn Pro Arg Val Pro Ser Arg Glu Asp Ile Leu Asp Ile Val Lys
    370                 375                 380

Lys Ala Tyr
385

<210> SEQ ID NO 12
<211> LENGTH: 1176
<212> TYPE: DNA
<213> ORGANISM: Aeribacillus pallidus

<400> SEQUENCE: 12
atgatcggaa attacgcaaa aaaggcgatt gatttcgagt tcacttttta tcttcctaca      60
ttgatcgaat tcggatacgg caaggcttcc cgaatgggag agatgcttga acagatgggt     120
ataaagaacg ttttttttggt taccgacaaa ggagtggaag ctgcgggtct gttggcagga     180
atcgttcagt ctctggaatc atccaatatc cgatatgtta tttattcaga cgtagaacct     240
gacccgagct tagagacgat tgatcgtggt gcgtccgttt ttaaggagca gtcttttgac     300
tgtatcttag ctgtgggtgg aggaagtccg attgatacag ctaaggggat ccgtgtcgta     360
gtgacgaacg gaggaaacat cggtgactat gccggtgtta accgtgttgc gaaaaaatct     420
gaaattcctt tggtggctgt gccgactaca tccggcacgg gcagtgaagt aaccattttc     480
ggagtctact ccgattggga aaatcaagta aaggtgacgg taacaagccc atatatggcg     540
ccggagatcg ctttggtaga ccccgaactt accatgagtc taccgcaaaa aatgacagca     600
gcatcgggaa ttgatgctct agctcatggg attgaaactt tcttctcctt gcgttctcga     660
cctgcatccg atgccctagc ggtcgaagcg atggcgacgg tgagtgctta tttgcgccgt     720
gcggtggaag atggtacgga taagaagcg aggatcggca tgtcccaggg cagtttgttg     780
gcagggatgg cattcaacaa tggcttctta ggtttggccc atgcgatcgg tagtgctttg     840
tctggccatt gtcatgtgtc ccatggtgtc gcaatcggtt tgttgctacc gaaagtggtg     900
gaatttaatg ctagggtgcg cccggaaaaa gctgcaaaaa tcgcagaatt gttgggagta     960
aaaggggatc gagaggaggt tcttgcggag caggcagctc ctgcagtcgc ctcgttagtc    1020
aaagagattg gtcttcccac tcgttttgcgt gatgttgatg tttctgaaga aaagctccca    1080
gatatcgcaa gagatgcatt taaaagcggt atgatgaagt taacccacg ccaaccaagt    1140
ttgtcagaag tgcttacact tttgcagcag atttat                                1176

<210> SEQ ID NO 13
<211> LENGTH: 1179
<212> TYPE: DNA
```

<213> ORGANISM: Artificial
<220> FEATURE:
<223> OTHER INFORMATION: Synthetic codon optimised for expression in P. putida

<400> SEQUENCE: 13

```
atgatcggca actacgccaa gaaggccatc gacttcgagt tcaccttcta cctgccgacc      60
ctgatcgagt tcggctacgg caaggccagc cgcatgggcg agatgctgga acaaatgggt     120
atcaagaacg tgttcctggt gaccgacaag ggcgtggaag ccgccggtct gctgccggc      180
atcgtgcaga gcctggaaag cagcaacatc cgctacgtga tctacagcga cgtggaaccg     240
gacccgagcc tggaaaccat cgaccgcggc gccagcgtgt tcaaagaaca gagcttcgac     300
tgcatcctgg ccgtgggcgg cggcagcccg atcgacaccg ccaagggcat ccgcgtggtg     360
gtgaccaacg cggcaacat cggcgactac gccggcgtga accgcgtggc caagaagtcg     420
gagatcccgc tggtcgccgt gccaaccacc tcgggcaccg gcagcgaagt gaccatcttc     480
ggcgtgtaca gcgactggga gaaccaggtg aaggtgaccg tgaccagccc gtacatggcc     540
ccggaaatcg ccctggtgga cccggaactg accatgagcc tgccgcagaa gatgaccgcc     600
gccagcggca tcgacgccct ggcccacggc atcgaaacct tcttcagcct gcgcagccgc     660
ccagcctcgg atgccctggc ggtggaagcc atggccaccg tgagcgccta cctgcgccgc     720
gccgtcgagg acggcaccga caagaagccc gcatcggca tgagccaggg cagcctgctg     780
gcgggcatgg ccttcaacaa cggcttcctg ggcctggccc atgccatcgg cagcgccctg     840
agcggccatt gccatgtgag ccacggcgtg gccatcggcc tgctgctgcc gaaggtggtg     900
gaattcaacg cccgcgtgcg cccggaaaag gccgccaaga tcgccgaact gctgggcgtg     960
aagggcgacc gcgaagaggt gctggccgaa caggccgccc cagccgtggc cagcctggtg    1020
aaagaaatcg gcctgccgac cgcctgcgc gacgtggacg tgagcgaaga aagctgccg    1080
gacatcgccc gcgacgcctt caagagcggc atgatgaagt tcaacccgcg ccagccgagc    1140
ctgagcgagg tgctgaccct gctgcagcag atctactga                           1179
```

<210> SEQ ID NO 14
<211> LENGTH: 1152
<212> TYPE: DNA
<213> ORGANISM: Artificial
<220> FEATURE:
<223> OTHER INFORMATION: Synthetic codon optimised for expression in P. putida

<400> SEQUENCE: 14

```
atggacgtgg aattcagctt ccatctgccg accctgatcg agttcggctt cggcaaggcc      60
agcctgctgg cgagcgcct gctgaagctg ggcgtgggca cgtgttcct ggtgagcgac      120
aagggcgtgg ccagcgcagg cctgctgcag aagctggaac agagcctgca gaccagcgac     180
atccacttca gacctacct ggaagtggaa ccggacccga gcctggaaac catcgacctg     240
ggtgccgagg ccttcaacag cggcaagtac gactgcatcg tggccgtggg tggtggcagc     300
gccatcgaca ccgccaaggg catccgcgtg gtggcaggca cgtggcag atcggcgac       360
ttcgcaggcg tggacaagat cggcaaggca ccgcagatcc cgctgatcgc cgtgccgacc     420
acctcgggca ccggcagcga agtgaccatc ttcggcgtgt acagcgactg ggtgaagaac     480
gtgaaggtga ccgtgaccag ccagtacatg gcaccgacca ttgccctggt ggacccggaa     540
ctgaccatgc cctgccacg caagatgacc gcagccagcg catcgacgc cctgcccac       600
ggcatcgaga gctacttcag cctgcgcagc accagcgcca gccgtgccct gtcgctggaa     660
```

```
gccatcaaca tcgtgggcaa ccatctgcgc cagagcgtgg cgaacggcga ggacaaggaa       720
gcacgctgcg gcatgagcca cggcagcctg ctggcaggac tggcgttcaa caacggcttc       780
ctgggcctgg cccatgccat cggcagcgca ctgagcggtc actgccacgt gccgcacggc       840
gtggccatcg gcctgctgct gccgcacgtg gtggaattca acagcagcga gtgcccagac       900
caggcagccg agatcgccaa gatcctgggc gtgaaggccg aggacgaacg ccagctggcc       960
gaacaggcca gccacgccgt gggcgacctg gtgaaggaca tcggcctgcc gacccgtctg      1020
cgcgacatga acgtgccgga agagaagctg gccgacattg cacgcgacag cttccagagc      1080
ggcatgatga agttcaaccc acgtcgtgcc agcgagagcg aggtgctgga actgctgcac      1140
cgcgtgtact ga                                                         1152
```

<210> SEQ ID NO 15
<211> LENGTH: 1994
<212> TYPE: DNA
<213> ORGANISM: Artificial
<220> FEATURE:
<223> OTHER INFORMATION: Synthetic XbaI-SalI fragment

<400> SEQUENCE: 15

```
tctagatctt ctttgataat aaatgaaagc agccggtatg gagagaaaaa agtgcactta        60
tatgaagttg attttatggt cggctttatt ttgcccgtcg tactggctgt ccacacgatg       120 ttcattttg atgcacaatt gaatggctgt acagttgcgt ttttgtcgat gtctggcggg       180
cacgcctcca tgcatgtgaa gcagattctt ttaagcgggc agcacccgct tttttggagg       240
gcaggcattc aggagcaaaa atggcagaga tcagttgggc gggatcagcc atttattcct       300
ccatccgggg cactttgtga aaatcagcac aagaatgaat aacgctttca tatctggctt       360
tttcaaataa aaccatttgt gaaaaatgta aacggatgat tttgaaaaac cgtcattttc       420
cttaaaaacc gggcatttgg gcagataaat tttcaaattt cgccataaa atatgtgaat       480 ctaatcacaa aaatagtggt atacttaccc atgtggaatg aaggaaaatg aacggaacga       540
tccatttcag cctaaaaagg gcatgccgtc catctatttc acaaaccgca cggcagcatt       600
tgctgcaaaa gtttaatcgt cctgctttaa aggaaaagca gtatggaatc cattaggagt       660
tggcacaata tccatagact ggatagggg ccgccatgcc gggcttgcaa aactgctttc       720
atacagtgga aatattttt actttttgatg gggaggaaga ttatatatga tcggaaatta       780
cgcaaaaaag gcgattgatt tcgagttcac tttttatctt cctacattga tcgaattcgg       840
atacggcaag gcttcccgaa tgggagagat gcttgaacag atgggtataa agaacgtttt       900
tttggttacc gacaaaggag tggaagctgc gggtctgttg gcaggaatcg ttcagtctct       960
ggaatcatcc aatatccgat atgttatta ttcagacgta gaacctgacc cgagcttaga      1020
gacgattgat cgtggtgcgt ccgttttaa ggagcagtct tttgactgta tcttagctgt       1080
gggtggagga agtccgattg atacagctaa ggggatccgt gtcgtagtga cgaacggagg      1140
aaacatcggt gactatgccg gtgttaaccg tgttgcgaaa aaatctgaaa ttcctttggt      1200
ggctgtgccg actacatccg gcacgggcag tgaagtaacc attttcggag tctactccga      1260
ttgggaaaat caagtaaagg tgacggtaac aagcccatat atggcgccgg agatcgcttt      1320
ggtagacccc gaacttacca tgagtctacc gcaaaaaatg acagcagcat cgggaattga      1380
tgctctagct catgggattg aaactttctt ctccttgcgt tctcgacctg catccgatgc      1440
cctagcggtc gaagcgatgg cgacggtgag tgcttatttg cgccgtgcgg tggaagatgg      1500
```

```
tacggataaa gaagcgagga tcggcatgtc ccagggcagt tgttggcag  ggatggcatt    1560 caacaatggc ttcttaggtt tggcccatgc gatcggtagt gctttgtctg ccattgtca    1620 tgtgtcccat ggtgtcgcaa tcggtttgtt gctaccgaaa gtggtggaat taatgctag    1680 ggtgcgcccg aaaaagctg caaaaatcgc agaattgttg ggagtaaaag gggatcgaga    1740
ggaggttctt gcggagcagg cagctcctgc agtcgcctcg ttagtcaaag agattggtct    1800
tcccactcgt ttgcgtgatg ttgatgtttc tgaagaaaag ctcccagata tcgcaagaga    1860
tgcatttaaa agcggtatga tgaagtttaa cccacgccaa ccaagtttgt cagaagtgct    1920 tacactttg cagcagattt attaattgtt cgggtttcag tgttccattt tcaaatattc     1980
cgttaagggt cgac                                                       1994

<210> SEQ ID NO 16
<211> LENGTH: 1258
<212> TYPE: DNA
<213> ORGANISM: Artificial
<220> FEATURE:
<223> OTHER INFORMATION: Synthetic KpnI-XbaI fragment

<400> SEQUENCE: 16
ggtaccttca cacaggaaac aggaggtaca atgatcggaa attacgcaaa aaaggcgatt      60
gatttcgagt tcacttttta tcttcctaca ttgatcgaat tcggatacgg caaggcttcc    120
cgaatgggag agatgcttga acagatgggt ataaagaacg ttttttttggt taccgacaaa    180 ggagtggaag ctgcgggtct gttggcagga atcgttcagt ctctggaatc atccaatatc    240
cgatatgtta tttattcaga cgtagaacct gacccgagct tagagacgat tgatcgtggt    300
gcgtccgttt taaggagca gtcttttgac tgtatcttag ctgtgggtgg aggaagtccg    360
attgatacag ctaaggggat ccgtgtcgta gtgacgaacg aggaaacat cggtgactat     420 gccggtgtta accgtgttgc gaaaaaatct gaaattcctt tggtggctgt gccgactaca    480
tccggcacgg gcagtgaagt aaccattttc ggagtctact ccgattggga aaatcaagta    540
aaggtgacgg taacaagccc atatatggcg ccggagatcg cttggtaga ccccgaactt     600 accatgagtc taccgcaaaa aatgacagca gcatcgggaa ttgatgctct agctcatggg    660
attgaaactt tcttctcctt gcgttctcga cctgcatccg atgccctagc ggtcgaagcg    720
atggcgacgg tgagtgctta tttgcgccgt gcggtggaag atggtacgga taaagaagcg    780
aggatcggca tgtcccaggg cagtttgttg cagggatgg cattcaacaa tggcttctta     840
ggtttggccc atgcgatcgg tagtgctttg tctggccatt gtcatgtgtc ccatggtgtc    900
gcaatcggtt tgttgctacc gaaagtggtg gaatttaatg ctagggtgcg cccggaaaaa    960
gctgcaaaaa tcgcagaatt gttgggagta aaagggatc gagaggaggt tcttgcggag   1020
caggcagctc ctgcagtcgc ctcgttagtc aaagagattg gtcttcccac tcgtttgcgt   1080
gatgttgatg tttctgaaga aaagctccca gatatcgcaa gagatgcatt taaaagcggt   1140
atgatgaagt ttaacccacg ccaaccaagt ttgtcagaag tgcttacact tttgcagcag   1200
atttattaat tgttcgggtt tcagtgttcc attttcaaat attccgttaa ggtctaga     1258

<210> SEQ ID NO 17
<211> LENGTH: 446
<212> TYPE: PRT
<213> ORGANISM: Aeribacillus pallidus

<400> SEQUENCE: 17

Met Lys Asn Ile Ala Asn Thr Ser Thr Glu Arg Pro Val Asn Asp Ala
```

-continued

```
1               5                   10                  15
Ser Val Lys Asn Arg Gln Met Val Arg Ala Thr Ile Ala Ser Leu Ile
            20                  25                  30

Gly Trp Ser Leu Asp Leu Tyr Asp Leu Phe Leu Leu Leu Phe Val Ala
            35                  40                  45

Thr Thr Ile Gly Asn Leu Phe Phe Pro Ala Ser Asn Gln Thr Leu Ser
 50                  55                  60

Leu Ala Ala Val Tyr Ala Ser Phe Ala Val Thr Leu Leu Met Arg Pro
 65                  70                  75                  80

Leu Gly Ser Ala Ile Phe Gly Ile Tyr Ala Asp Lys Asn Gly Arg Lys
                85                  90                  95

Lys Ala Met Thr Val Ala Ile Ile Gly Ala Gly Leu Cys Thr Ala Ala
            100                 105                 110

Phe Gly Leu Leu Pro Thr Ile His Gln Val Gly Val Val Ala Ala Ile
            115                 120                 125

Ala Phe Leu Ile Leu Arg Leu Val Gln Gly Val Phe Val Gly Gly Val
            130                 135                 140

Val Ala Ser Thr His Thr Ile Gly Thr Glu Ser Ala Ser Pro Lys Tyr
145                 150                 155                 160

Arg Gly Phe Met Ser Gly Leu Ile Gly Gly Gly Ala Gly Leu Gly
                165                 170                 175

Ala Leu Phe Ala Ser Ile Ser Tyr Ser Val Val Thr Ala Ile Phe Pro
            180                 185                 190

Gly Glu Ala Phe Asp Val Trp Gly Trp Arg Val Met Phe Phe Thr Gly
            195                 200                 205

Ile Ile Gly Ser Leu Phe Gly Leu Phe Ile Phe Arg Ser Leu Glu Glu
210                 215                 220

Ser Pro Leu Trp Lys Gln Leu Lys Glu Glu Asn Ser Lys Gly Glu Val
225                 230                 235                 240

Ser Glu Phe Gln Lys Ala Pro Leu Lys Thr Phe Phe Thr Lys Tyr Tyr
            245                 250                 255

Lys Val Leu Leu Val Asn Leu Met Ile Val Ile Gly Gly Ser Gly
            260                 265                 270

Tyr Tyr Leu Thr Ser Gly Phe Ile Pro Thr Phe Leu Lys Val Val Asn
            275                 280                 285

Lys Val Ser Ala Ser Val Ser Ser Gly Val Leu Ile Ala Thr Ser Ile
290                 295                 300

Met Thr Ile Val Ala Ala Val Leu Val Gly His Leu Ser Glu Val Ile
305                 310                 315                 320

Gly Arg Lys Lys Thr Phe Leu Leu Ile Gly Ile Leu Cys Leu Val Gly
            325                 330                 335

Leu Pro Tyr Phe Tyr Leu Ser Leu Ala Asn Ser Thr Thr Thr Thr Gly
            340                 345                 350

Ile Tyr Leu Asn Ala Leu Gly Leu Ile Phe Leu Gly Asn Ala Ala Tyr
            355                 360                 365

Ala Pro Val Leu Ile Phe Leu Asn Glu Arg Phe Pro Thr Ser Ile Arg
            370                 375                 380

Ser Thr Gly Thr Gly Leu Ser Trp Asn Met Gly Phe Ala Ile Gly Gly
385                 390                 395                 400

Met Met Pro Thr Phe Val Asn Leu Ala Ser Gly Thr Val Glu His Ile
            405                 410                 415

Pro Tyr Thr Leu Met Tyr Phe Thr Ile Gly Ile Tyr Leu Val Tyr Ile
            420                 425                 430
```

Leu Gly Ser Leu Ile Ile Pro Glu Thr Lys Gly Asn Leu Lys
        435                 440                 445

<210> SEQ ID NO 18
<211> LENGTH: 1338
<212> TYPE: DNA
<213> ORGANISM: Aeribacillus pallidus

<400> SEQUENCE: 18

| | | | | | |
|---|---|---|---|---|---|
| gtgaagaata | tcgctaatac | gagtaccgaa | cgacctgtaa | atgatgcttc agttaagaat | 60 |
| cgtcaaatgg | tgcgagctac | gattgcctcg | ctcataggt | ggtcactcga tctttacgat | 120 |
| ttatttctgc | tgcttttgt | tgcgacgacc | atagggaatt | tgttttttcc cgccagcaat | 180 |
| caaacacttt | ctttggctgc | cgtgtatgct | tcctttgccg | ttacgctttt gatgcggcct | 240 |
| ttgggttccg | ccatttcgg | catttatgcg | ataaaaacg | ggagaaagaa agcgatgact | 300 |
| gtggcaatca | ttggagcagg | cttgtgcacg | gcggctttcg | gtctgttacc tacgatccac | 360 |
| caagttggag | tggtcgctgc | gatcgccttc | ttgattttac | gtttagttca aggagtgttt | 420 |
| gtcggcggag | tggttgcttc | cacccatacg | ataggaacgg | aatccgcatc gccaaaatat | 480 |
| cgggggttta | tgtcgggatt | gatcgtggt | ggcggagcag | gattgggagc actgtttgct | 540 |
| tctatttctt | attcggttgt | gacggcaatt | tttccgggag | aggcttttga tgtttgggga | 600 |
| tggcgtgtca | tgttttttcac | aggcattatc | ggttccctct | tcggccttttt catattccgg | 660 |
| tcccttgagg | aatctcctct | ctggaaacaa | ttgaagaag | aaaatagtaa aggcgaagtg | 720 |
| tccgagtttc | agaaagcacc | gctgaagacg | ttttttcacta | aatattacaa ggtattgctc | 780 |
| gtcaacctta | tgatcgtcat | cggtggtggc | tccggttatt | atctgactag tggattattt | 840 |
| cctacatttt | taaaggtagt | taacaaagta | tcagcctctg | tttcgtcggg ggtactcatt | 900 |
| gcgacaagta | ttatgaccat | tgtagccgcc | gttctcgtgg | gacacctgag cgaggtcatc | 960 |
| ggcagaaaga | aaacatttct | gttaatcggt | attctttgtc | ttgtcggact tccgtatttt | 1020 |
| tatctgtcat | tggcaaactc | aactacgaca | acgggcatct | acttaaatgc tcttggactc | 1080 |
| atattcttgg | ggaatgctgc | atatgcaccg | gtactcatct | tcttgaacga acgttttccc | 1140 |
| acatcgatcc | gttcaacagg | taccggatta | tcatggaaca | tgggtttcgc cattggcggg | 1200 |
| atgatgccga | cgtttgtgaa | cttagccagt | ggtacggtgg | aacatattcc ttacacgctg | 1260 |
| atgtatttta | ctatcggaat | ttacttggtt | tatatccttg | gcagcctgat tattccggaa | 1320 |
| acaaaaggaa | acctcaaa | | | | 1338 |

<210> SEQ ID NO 19
<211> LENGTH: 1184
<212> TYPE: DNA
<213> ORGANISM: Artificial
<220> FEATURE:
<223> OTHER INFORMATION: Synthetic KpnI - NheI fragment with codon
      optimized B.kribbensis YiaY

<400> SEQUENCE: 19

| | | | | | |
|---|---|---|---|---|---|
| ggtacctagg | aaaggaagat | taacccatgg | acgtggaatt | cagcttccat ctgccgaccc | 60 |
| tgatcgagtt | cggcttcggc | aaggccagcc | tgctgggcga | cgcctgctg aagctgggcg | 120 |
| tgggcaacgt | gttcctggtg | agcgacaagg | gcgtggccag | cgcaggcctg ctgcagaagc | 180 |
| tggaacagag | cctgcagacc | agcgacatcc | acttcaagac | ctacctggaa gtggaaccgg | 240 |
| acccgagcct | ggaaaccatc | gacctgggtg | ccgaggcctt | caacagcggc aagtacgact | 300 |

```
gcatcgtggc cgtgggtggt ggcagcgcca tcgacaccgc caagggcatc cgcgtggtgg    360
caggcaacgg tggcagcatc ggcgacttcg caggcgtgga caagatcggc aaggcaccgc    420
agatcccgct gatcgccgtg ccgaccacct cgggcaccgg cagcgaagtg accatcttcg    480
gcgtgtacag cgactgggtg aagaacgtga aggtgaccgt gaccagccag tacatggcac    540
cgaccattgc cctggtggac ccggaactga ccatgcgcct gccacgcaag atgaccgcag    600
ccagcggcat cgacgccctg gcccacggca tcgagagcta cttcagcctg cgcagcacca    660
gcgccagccg tgccctgtcg ctggaagcca tcaacatcgt gggcaaccat ctgcgccaga    720
gcgtggcgaa cggcgaggac aaggaagcac gctgcggcat gagccacggc agcctgctgg    780
caggcatggc gttcaacaac ggcttcctgg gcctggccca tgccatcggc agcgcactga    840
gcggtcactg ccacgtgccg cacggcgtgg ccatcggcct gctgctgccg cacgtggtgg    900
aattcaacag cagcgagtgc ccagaccagg cagccgagat cgccaagatc ctgggcgtga    960
aggccgagga cgaacgccag ctggccgaac aggccagcca cgccgtgggc gacctggtga   1020
aggacatcgg cctgccgacc cgtctgcgcg acatgaacgt gccggaagag aagctggccg   1080
acattgcacg cgacagcttc cagagcggca tgatgaagtt caacccacgt cgtgccagcg   1140
agagcgaggt gctggaactg ctgcaccgcg tgtactgagc tagc                    1184
```

<210> SEQ ID NO 20
<211> LENGTH: 1359
<212> TYPE: DNA
<213> ORGANISM: Artificial
<220> FEATURE:
<223> OTHER INFORMATION: EcoRI-NheI PCR fragment with A.pallidus proP
      coding sequence

<400> SEQUENCE: 20

```
gccgaattca tgaagaatat cgctaatacg agtaccgaac gacctgtaaa tgatgcttca     60
gttaagaatc gtcaaatggt gcgagctacg attgcctcgc tcatagggtg gtcactcgat    120
ctttacgatt tatttctgct gcttttttgtt gcgacgacca tagggaattt gttttttccc    180
gccagcaatc aaaacacttt ctttggctgc cgtgtatgct tcctttgccgt tacgcttttg    240 atgcggcctt tgggttccgc cattttcggc atttatgcgg ataaaaacgg gagaaagaaa    300
gcgatgactg tggcaatcat tggagcaggc ttgtgcacgg cggctttcgg tctgttacct    360
acgatccacc aagttggagt ggtcgctgcg atcgccttct tgattttacg tttagttcaa    420
ggagtgtttg tcggcggagt ggttgcttcc acccatacga taggaacgga atccgcatcg    480
ccaaaatatc gggggtttat gtcgggattg atcggtggtg gcggagcagg attgggagca    540
ctgtttgctt ctatttctta ttcggttgtg acggcaattt ttccgggaga ggcttttgat    600
gtttggggat ggcgtgtcat gttttttcaca ggcattatcg gttccctctt cggccttttc    660
atattccggt cccttgagga atctcctctc tggaaacaat gaaagaaga aaatagtaaa    720 ggcgaagtgt ccgagtttca gaaagcaccg ctgaagacgt ttttcactaa atattacaag    780
gtattgctcg tcaaccttat gatcgtcatc ggtggtggct ccggttatta tctgactagt    840
ggatttattc ctacatttt aaaggtagtt aacaaagtat cagcctctgt ttcgtcgggg    900
gtactcattg cgacaagtat tatgaccatt gtagccgccg ttctcgtggg acacctgagc    960
gaggtcatcg gcagaaagaa aacatttctg ttaatcggta ttctttgtct tgtcggactt   1020
ccgtattttt atctgtcatt ggcaaactca actacgacaa cgggcatcta cttaaatgct   1080
cttggactca tattcttggg gaatgctgca tatgcaccgg tactcatctt cttgaacgaa   1140
```

```
cgttttccca catcgatccg ttcaacaggt accggattat catggaacat gggtttcgcc      1200
attggcggga tgatgccgac gtttgtgaac ttagccagtg gtacggtgga acatattcct      1260
tacacgctga tgtattttac tatcggaatt tacttggttt atatccttgg cagcctgatt      1320
attccggaaa caaaaggaaa cctcaaataa gctagcggc                              1359
```

<210> SEQ ID NO 21
<211> LENGTH: 20
<212> TYPE: DNA
<213> ORGANISM: Artificial
<220> FEATURE:
<223> OTHER INFORMATION: ribosome binding site

<400> SEQUENCE: 21

```
taggaaagga agattaaccc                                                   20
```

<210> SEQ ID NO 22
<211> LENGTH: 30
<212> TYPE: DNA
<213> ORGANISM: Artificial
<220> FEATURE:
<223> OTHER INFORMATION: PCR primer proP(f)

<400> SEQUENCE: 22

```
gccgaattca tgaagaatat cgctaatacg                                        30
```

<210> SEQ ID NO 23
<211> LENGTH: 34
<212> TYPE: DNA
<213> ORGANISM: Artificial
<220> FEATURE:
<223> OTHER INFORMATION: PCR primer proP(r)

<400> SEQUENCE: 23

```
gccgctagct tatttgaggt ttccttttgt ttcc                                   34
```

<210> SEQ ID NO 24
<211> LENGTH: 500
<212> TYPE: PRT
<213> ORGANISM: Cupriavidus basilensis

<400> SEQUENCE: 24

```
Met Asn Ala Gln His Trp Ile Ala Gly Ala Trp Thr Gly Glu Pro Ser
1               5                   10                  15

Ala Asp Ser Val Asn Pro Ala Asp Gly Thr Leu Ile Gly Gln Phe Ala
            20                  25                  30

Asp Gly Gly Thr Trp Gln Ala Glu Ala Ala Ile Ala Ala Ala Arg His
        35                  40                  45

Val Phe Glu Arg Thr Thr Trp Gly Gln Asp Ala Arg Leu Arg Gln Asp
    50                  55                  60

Val Leu Leu Ala Trp Ala Gly Ala Leu Glu Ala Glu Arg Glu Arg Leu
65                  70                  75                  80

Ala Ser Leu Leu Thr Ala Glu Asn Gly Lys Pro Val Ala Gln Ala Arg
                85                  90                  95

Gly Glu Val Gly Ala Ala Ile Ser Glu Val Arg Tyr Tyr Ala Gly Leu
            100                 105                 110

Ala Arg His Ile Pro Gly His Val Leu Glu Pro Glu Pro Gly Thr Ile
        115                 120                 125

Ser Thr Ile Leu Arg Glu Pro Ala Gly Val Ala Ala Ile Ile Val Pro
    130                 135                 140
```

```
Trp Asn Ala Pro Ala Val Leu Leu Val Arg Ser Leu Ala Pro Ala Leu
145                 150                 155                 160

Ala Ala Gly Cys Thr Ala Val Val Lys Ser Ala Ala Gln Thr Thr Leu
            165                 170                 175

Phe Thr Ala Ala Met Leu Arg Leu Phe Glu Arg Thr Ala Leu Pro Ala
        180                 185                 190

Gly Ala Val Asn Leu Val Cys Glu Thr Gly Tyr Ala Ala Ala Asp His
    195                 200                 205

Leu Val Arg Ser Arg Asp Val Asp Val Ser Phe Thr Gly Ser Thr
210                 215                 220

Ala Thr Gly Lys Lys Ile Met Ile Ala Ala Asp Ser Val Lys Lys
225                 230                 235                 240

Leu Ser Leu Glu Leu Gly Gly Lys Ser Cys Cys Leu Val Phe Asp Asp
                245                 250                 255

Val Asp Ala Gln Ala Val Ala Lys Arg Leu Ala Leu Ala Ala Thr Val
            260                 265                 270

Ile Ser Gly Gln Gln Cys Thr Ala Ala Arg Arg Val Leu Val His Glu
        275                 280                 285

Ala Ile Ala Pro Gln Met Arg Arg His Leu Thr Glu Ala Leu Ala Ala
    290                 295                 300

Leu Arg Leu Gly Pro Gly Ile Glu Pro Asp Thr Gln Ile Gly Pro Leu
305                 310                 315                 320

Ile Asp His Pro Thr Arg Ala Met Val Ser Ala Gln Val Glu Arg Ala
                325                 330                 335

Cys Asp Glu Ala Asp Thr Val Leu Leu Arg Gly Thr Met Pro Gly Gly
            340                 345                 350

Ala Leu Ala Arg Gly Ala Phe Leu Ser Pro Thr Leu Val Glu His Ser
        355                 360                 365

Asp Pro Gly Ala Phe Phe Cys Gln Glu Glu Ile Phe Gly Pro Phe Val
    370                 375                 380

Thr Phe Glu Thr Phe Ala Thr Glu Asp Glu Ala Leu Ala Lys Ala Asn
385                 390                 395                 400

Asn Thr Val Phe Gly Leu Ser Ala Ser Val Trp Thr His His Gly Glu
                405                 410                 415

Arg Ala Ile Arg Leu Ala Arg Ala Leu Arg Asn Gly Thr Val Trp Val
            420                 425                 430

Asn Asp His Asn Arg Leu Phe Ala Glu Ala Glu Thr Gly Gly Tyr Arg
        435                 440                 445

Gln Ser Gly Leu Gly Arg Leu His Gly Tyr Asp Ala Leu Ala Asp Phe
    450                 455                 460

Thr Glu Leu Lys His Ile Cys Ile Gln Ala Gly Leu Pro Lys Gly Met
465                 470                 475                 480

Ser Gln Ala Gly Cys Arg Leu Ser Gly Val Ala Ala Arg Glu Arg Met
                485                 490                 495

Gly Val Ser Val
            500

<210> SEQ ID NO 25
<211> LENGTH: 479
<212> TYPE: PRT
<213> ORGANISM: Burkholderia sp. CCGE1002

<400> SEQUENCE: 25

Met Asn Ala Arg His Trp Ile Ala Gly Glu Trp Thr Gly Thr Pro Asn
1               5                   10                  15
```

```
Ile Asp Ser Ile Asp Pro Ala Thr Gly Asp Ala Ile Gly Arg Phe Ala
         20                  25                  30

Asp Gly Gly Ser Ser Glu Ala Asp Ala Ala Ile Ala Ala Ala Arg His
     35                  40                  45

Ala Phe Asp Arg Thr Thr Trp Ala Gln Asp Ala Arg Leu Arg Gln Asp
 50                  55                  60

Val Leu Leu Gly Trp Ala Ser Ala Leu Glu Ala Glu Arg Asp Met Leu
 65                  70                  75                  80

Ala Thr Leu Leu Thr Arg Glu Asn Gly Lys Ala Ile Ala Gln Ser Arg
                 85                  90                  95

Asp Glu Ile Ala Gly Ala Ile Ser Glu Val Arg Tyr Tyr Ala Gly Leu
            100                 105                 110

Ala Arg His Ile Ala Gly His Val Leu Glu Pro Glu Pro Gly Thr Ile
         115                 120                 125

Ser Thr Met Leu Arg Glu Ala Ala Gly Val Ala Ala Ile Ile Val Pro
 130                 135                 140

Trp Asn Ala Pro Ala Val Leu Leu Val Arg Ser Leu Ala Pro Ala Leu
145                 150                 155                 160

Ala Ala Gly Cys Thr Val Ile Val Lys Pro Ala Ala Gln Thr Ser Leu
                165                 170                 175

Leu Thr Ala Ala Met Leu Arg Cys Phe Glu His Thr Ala Leu Pro Glu
            180                 185                 190

Gly Ala Val Asn Leu Val Asn Glu Arg Gly Tyr Ala Ala Ser Gln Arg
         195                 200                 205

Leu Val Asp Ser His Gly Val Asp Val Val Ser Phe Thr Gly Ser Thr
 210                 215                 220

Ala Thr Gly Lys Lys Ile Met Ala Ala Ala Asp Ser Met Lys Lys
225                 230                 235                 240

Leu Ser Leu Glu Leu Gly Gly Lys Ser Cys Cys Val Val Phe Asp Asp
                245                 250                 255

Ala Asp Val Ala Ala Ile Ala Pro Arg Leu Ala Arg Ala Ala Thr Ile
            260                 265                 270

Ile Ser Gly Gln Gln Cys Thr Ala Ala Arg Arg Val Leu Val His Ala
         275                 280                 285

Ser Arg Ala Ala Gln Met Arg Glu Gln Leu Ala Ser Ala Leu Ala Ser
 290                 295                 300

Leu Arg Val Gly Pro Gly Ile Asp Pro Ala Thr Asp Ile Gly Ala Leu
305                 310                 315                 320

Ile Asp Gly Thr Thr Arg Asp Ala Val Ala Arg Thr Ile Glu Arg Ala
                325                 330                 335

Cys Gly Thr Ala Glu Arg Val Leu Leu Arg Gly Thr Cys Ser Gly His
            340                 345                 350

Ala Phe Leu Ser Pro Thr Leu Val Glu His Asp Asp Pro Lys Ala Phe
         355                 360                 365

Phe Cys Gln Asp Glu Ile Phe Gly Pro Phe Val Thr Leu Glu Val Phe
 370                 375                 380

Glu Asn Glu Met Glu Ala Ile Glu Lys Ala Asn Asp Thr Val Phe Gly
385                 390                 395                 400

Leu Ser Ala Ser Val Trp Thr His Asp Gly Ala Arg Ala Leu Arg Val
                405                 410                 415

Ala Arg Ala Leu Arg Asn Gly Thr Val Trp Ile Asn Asp His Asn Lys
            420                 425                 430
```

```
Leu Phe Ala Glu Ala Glu Thr Gly Gly Tyr Arg Gln Ser Gly Leu Gly
        435                 440                 445

Arg Leu His Gly Tyr Asp Ala Leu Ala Asp Phe Thr Glu Leu Lys His
    450                 455                 460

Ile Cys Met Pro Ala Gly Val Ala Glu Gly Ile Ala Pro Leu Arg
465                 470                 475

<210> SEQ ID NO 26
<211> LENGTH: 483
<212> TYPE: PRT
<213> ORGANISM: Burkholderia graminis C4D1M

<400> SEQUENCE: 26

Met Glu Arg Asp Ala Met Asn Trp Ile Ala Gly Glu Trp Ala Gly Lys
1               5                   10                  15

Pro Val Leu Ala Ser Ser Asp Pro Ser Asn Gly Glu Thr Leu Gly Arg
            20                  25                  30

Phe Val Ser Ser Asn Thr Gln Asp Ala Asp Ala Ala Val Ser Ala Ala
        35                  40                  45

Arg His Thr Phe Asp His Thr Thr Trp Ala Gln Asp Ala Arg Arg Arg
    50                  55                  60

Gln Asp Val Leu Leu Arg Trp Ala Gln Ala Leu Glu Leu Ser Val Glu
65                  70                  75                  80

Pro Leu Ala Glu Leu Leu Thr His Glu Asn Gly Lys Thr Ile Gly Gln
                85                  90                  95

Ala Arg Gly Glu Met Arg Ala Ala Ile Ser Glu Val Arg Tyr Tyr Ala
            100                 105                 110

Gly Leu Ala Arg His Ile Ala Gly His Val Ile Glu Pro Glu Pro Gly
        115                 120                 125

Thr Ile Ser Thr Met Leu Arg Glu Ala Ala Gly Val Ala Ala Ile Ile
    130                 135                 140

Val Pro Trp Asn Ala Pro Ala Val Leu Leu Val Arg Ser Leu Ala Pro
145                 150                 155                 160

Ala Leu Ala Ala Gly Cys Thr Ala Ile Val Lys Pro Ala Ala Gln Thr
                165                 170                 175

Ser Leu Ile Thr Ala Ala Met Ile Arg Cys Leu Asp Gln Pro Ala Leu
            180                 185                 190

Pro Ala Gly Ala Val Asn Leu Leu Leu Glu Asn Gly Ala Glu Ala Ala
        195                 200                 205

Ala Arg Leu Val Glu Ser Ala Asp Val Asp Val Ile Ser Phe Thr Gly
    210                 215                 220

Ser Thr Glu Val Gly Lys Arg Ile Met Arg Ala Ala Ala Asp Ser Met
225                 230                 235                 240

Lys Arg Leu Ser Leu Glu Leu Gly Gly Lys Ser Cys Cys Leu Val Phe
                245                 250                 255

Glu Asp Ser Asp Val Lys Ala Ile Ala Pro Arg Leu Ala Arg Ala Ala
            260                 265                 270

Thr Ile Ile Ser Gly Gln Gln Cys Thr Ala Ala Arg Arg Ile Leu Val
        275                 280                 285

His Val Ser Lys Ala Asp Gln Met Arg Asp Glu Leu Val Lys Ala Leu
    290                 295                 300

Ala Ser Leu Lys Val Gly Pro Gly Ile Asp Pro Ala Ser Asp Ile Gly
305                 310                 315                 320

Ala Leu Ile Asp Ala Ala Ser Arg Asp Ala Val Gln Thr Thr Val Glu
                325                 330                 335
```

```
Arg Ala Cys Asp Leu Ala Asp Arg Val Leu Arg Gly Thr Ser Ser
            340                 345                 350

Gly Pro Gly Ala Phe Leu Ser Pro Thr Leu Val Glu His Gly Glu Pro
        355                 360                 365

His Ala Phe Phe Cys Gln Asp Glu Ile Phe Gly Pro Phe Val Thr Leu
370                 375                 380

Glu Thr Phe Val Thr Glu Lys Glu Ala Val Glu Lys Ala Asn Asn Thr
385                 390                 395                 400

Val Phe Gly Leu Ser Ala Ser Val Trp Thr His Asp Ser Ala Arg Ala
                405                 410                 415

Phe Arg Ile Ala Arg Ala Leu Arg Asp Gly Thr Val Trp Ile Asn Asp
                420                 425                 430

His Asn Arg Leu Phe Ala Glu Ala Glu Thr Gly Gly Tyr Arg Gln Ser
            435                 440                 445

Gly Leu Gly Arg Leu His Gly Tyr Asp Ala Leu Ala Asp Phe Thr Glu
        450                 455                 460

Ile Lys His Ile Cys Val Gly Ala Gly Val Leu Gly Ile Glu Val
465                 470                 475                 480

Leu Gly Ser

<210> SEQ ID NO 27
<211> LENGTH: 483
<212> TYPE: PRT
<213> ORGANISM: Azospirillum sp. B510

<400> SEQUENCE: 27

Met Thr Asn Leu Asp Ser Arg His Trp Ile Asp Gly Ala Trp Val Pro
1               5                   10                  15

Gly Thr Asp Arg Phe Ala Ser Ile Asn Pro Ala Asp Gly Ser Val Leu
            20                  25                  30

Gly His Ala Ala Asp Gly Gly Arg Ala Glu Ala Glu Ala Ala Ile Ala
        35                  40                  45

Ala Ala His Ala Ala Phe Asn Arg Pro Asp Trp Ala Gln Asn Pro Arg
50                  55                  60

Leu Arg Gln Ser Ile Leu Gly Trp Ala Asp Arg Leu Asp Thr Gln
65                  70                  75                  80

Ala Glu Asp Leu Ala Arg Leu Leu Thr Leu Glu Asn Gly Lys Ala Ile
                85                  90                  95

Ala Gln Ser Arg Gly Glu Ile Ala Gly Ala Ile Ser Glu Ile Arg Tyr
            100                 105                 110

Tyr Gly Gly Leu Ala Arg His Val Pro Gly His Val Leu Glu Val Glu
        115                 120                 125

Pro Gly Val Leu Ser Thr Met Leu Arg Glu Pro Ala Gly Val Ala Ala
    130                 135                 140

Leu Ile Ile Pro Trp Asn Ala Pro Ala Val Leu Leu Ala Arg Ala Ile
145                 150                 155                 160

Gly Pro Ala Leu Ala Cys Gly Cys Thr Val Val Lys Pro Ala Ala
                165                 170                 175

Gln Thr Thr Leu Leu Thr Ala Ala Phe Leu Arg Ala Leu Ser Glu Val
            180                 185                 190

Pro Ser Leu Pro Arg Gly Val Cys Asn Met Ile Ser Glu Thr Gly His
        195                 200                 205

Ala Ala Ala Ala Arg Leu Val Asp Ser Pro Leu Val Asp Val Val Ser
    210                 215                 220
```

Phe Thr Gly Ser Thr Ala Thr Gly Lys Arg Ile Met Val Ala Ala
225                 230                 235                 240

Asp Thr Met Lys Lys Leu Ser Leu Glu Leu Gly Gly Lys Ser Cys Cys
            245                 250                 255

Leu Val Phe Pro Asp Ala Asp Pro Ala Glu Thr Ala Ala Arg Ile Ala
        260                 265                 270

Thr Ala Ala Thr Ile Ile Ser Gly Gln Gln Cys Thr Ala Ala Arg Arg
            275                 280                 285

Val Leu Val His Ala Ser Ala Phe Asp Ala Met Lys Thr His Leu Arg
        290                 295                 300

Ala Ala Leu Ala Ala Met Thr Val Gly Asn Gly Leu Asp Pro Ala Ile
305                 310                 315                 320

Arg Met Gly Pro Leu Ile Asp Arg Pro Ala Arg Asp Gln Val Gln Thr
            325                 330                 335

Gln Val Glu Arg Ala Phe Asp Ala Cys Asp Glu Val Leu Leu Arg Gly
        340                 345                 350

Gly Val Pro Thr Asp Ser Pro Ala Ala Ala Ser Phe Leu Thr Pro Ser
            355                 360                 365

Leu Val Ala His Asp Asp Pro Ser Ala Phe Phe Cys Gln Asp Glu Ile
        370                 375                 380

Phe Gly Pro Phe Val Val Leu Glu Arg Phe Glu Thr Glu Ala Glu Ala
385                 390                 395                 400

Val Ala Lys Ala Asn Asn Thr Val Phe Gly Leu Ser Ala Ser Val Trp
                405                 410                 415

Thr Arg Asp Gly Ala Arg Ala Leu Arg Met Ala Arg Ala Leu Arg Asn
            420                 425                 430

Gly Thr Val Trp Ile Asn Asp His Asn Arg Leu Phe Ala Glu Ala Glu
        435                 440                 445

Thr Gly Gly Tyr Arg Gln Ser Gly Leu Gly Arg Leu His Gly Tyr Asp
    450                 455                 460

Ala Phe Ala Asp Phe Thr Glu Leu Lys His Val Cys Gln Thr Val Gly
465                 470                 475                 480

Thr Ile Gly

<210> SEQ ID NO 28
<211> LENGTH: 480
<212> TYPE: PRT
<213> ORGANISM: Pseudomonas putida

<400> SEQUENCE: 28

Met Gln Ser Gln His Tyr Ile Asp Gly Gln Trp Thr Ser Thr Asp Arg
1               5                   10                  15

Trp Thr Asp Ser Leu Asp Pro Ala Ser Gly Glu Leu Ile Gly Cys Phe
            20                  25                  30

Ala Asp Gly Gly Glu Ala Glu Ala Ala Val Ala Ala Ala Ala
        35                  40                  45

Arg Ala Phe Asn Asp Pro Gln Trp Ala Gln Asn Pro Arg Leu Arg Gln
    50                  55                  60

Gln Leu Leu Leu Glu Trp Ala Ala Gly Leu Lys Ala Arg Gln Glu Gln
65                  70                  75                  80

Leu Ala Gln Leu Leu Thr Arg Glu Asn Gly Lys Ala Leu Ala Gln Ser
                85                  90                  95

Arg Gly Glu Ile Gly Gly Ala Ile Ser Glu Ile Leu Tyr Tyr Ala Gly
            100                 105                 110

Leu Ala Arg His Asn Pro Gly His Met Leu Glu Val Ala Pro Gly Glu
            115                 120                 125

Phe Ser Ser Met Leu Arg Glu Pro Ala Gly Val Ala Gly Leu Ile Ile
        130                 135                 140

Pro Trp Asn Ala Pro Ala Val Leu Leu Val Arg Ala Leu Ala Pro Ala
145                 150                 155                 160

Ile Ala Ala Gly Cys Thr Val Val Ile Lys Pro Ala Pro Gln Thr Ala
                165                 170                 175

Leu Phe Asn Ala Ala Met Leu Glu Pro Leu Phe Ala Leu Pro Gly Leu
            180                 185                 190

Pro Ala Gly Ala Val Asn Leu Phe Ala Glu Ser Gly His Ala Gly Ala
        195                 200                 205

Ala His Leu Val Ala Ser Pro Arg Val Asp Val Leu Ser Phe Thr Gly
210                 215                 220

Ser Thr Ala Thr Gly Gln Arg Ile Met Arg Asp Cys Ala Ala Thr Met
225                 230                 235                 240

Lys Lys Leu Ser Leu Glu Leu Gly Gly Lys Ser Cys Cys Leu Val Phe
                245                 250                 255

Glu Asp Ala Asp Ile Ala Ala Ile Ala Pro Lys Leu Ala Ala Ala Ala
            260                 265                 270

Thr Ile Ile Ser Gly Gln Gln Cys Thr Ala Ala Arg Arg Val Leu Val
        275                 280                 285

His Ala Ser Arg Phe Ala Glu Met Lys Thr Ala Leu Ser Ala Ala Leu
    290                 295                 300

Gly Gln Ile Arg Leu Gly Asn Gly Leu Asp Pro Ala Asn Asn Met Gly
305                 310                 315                 320

Pro Leu Ile Asp Trp His Ser Arg Asp Ser Val Glu Arg Arg Ile Gly
                325                 330                 335

Glu Ala Leu Asp Ser Cys Asp Glu Val Leu Leu Ala Gly Gly Arg Pro
            340                 345                 350

Gln Gly Glu Leu Ser Lys Gly Ala Phe Leu Ala Pro Ser Leu Ile Ala
        355                 360                 365

His Arg Asp Ser Ser Ala Phe Phe Cys Gln Glu Ile Phe Gly Pro
    370                 375                 380

Leu Leu Val Leu Glu Ser Phe Glu Asp Glu Thr Glu Ala Val Ala Arg
385                 390                 395                 400

Ala Asn His Thr Glu Phe Gly Leu Ser Ala Ser Val Trp Thr Asp Gln
                405                 410                 415

Gly Ala Arg Ala Trp Arg Val Ala Arg Ala Leu Arg Asn Gly Thr Val
            420                 425                 430

Trp Leu Asn Asp His Asn Arg Leu Phe Ala Glu Ala Glu Thr Gly Gly
        435                 440                 445

Tyr Arg Lys Ser Gly Leu Gly Arg Leu His Gly Val Asp Ala Leu Leu
    450                 455                 460

Asp Phe Ser Glu Leu Lys His Ile Tyr Gln Asn Val Gly Thr Leu Gly
465                 470                 475                 480

<210> SEQ ID NO 29
<211> LENGTH: 486
<212> TYPE: PRT
<213> ORGANISM: Rhodopseudomonas palustris

<400> SEQUENCE: 29

Met Gly Met Thr Ala Leu His Ala Asp Asn Leu Ile Asp Gly Ala Trp

-continued

```
1               5                   10                  15
Gln Pro Ala Gln Ser Gly Ala Thr Ala Pro Ser Leu Asp Pro Ser Ser
            20                  25                  30
Gly Gly Thr Ile Gly Gly Phe Ala Ala Gly Gly Ala Ala Asp Ala Gln
            35                  40                  45
Ala Ala Val Ala Ala Ala Arg Ala Phe Glu Arg Pro Glu Trp Ser
    50                  55                  60
Gln Asn Pro Arg Ala Arg Gln Met Val Met Leu Arg Trp Ala Asp Arg
65                  70                  75                  80
Met Glu Ala Gln Ala Asp Gln Leu Ala Arg Leu Leu Thr Leu Glu Asn
                85                  90                  95
Gly Lys Pro Leu Pro Gln Ser Arg Gly Glu Ile Ala Gly Ser Val Ser
            100                 105                 110
Glu Ile Arg Tyr Tyr Ala Gly Leu Thr Arg Tyr Ile Pro Gly His Val
            115                 120                 125
Phe Glu Val Glu Pro Gly Ser Phe Ser Thr Leu Leu Lys Glu Pro Ala
    130                 135                 140
Gly Val Ala Gly Leu Ile Ile Pro Trp Asn Ala Pro Ala Val Leu Leu
145                 150                 155                 160
Ile Arg Ala Leu Thr Pro Ala Leu Ala Ala Gly Cys Thr Val Ile
                165                 170                 175
Lys Pro Ala Pro Gln Thr Ala Gln Ile Thr Ala Ile Ile Lys Cys
            180                 185                 190
Leu His Glu Val Asp Gly Leu Pro Arg Gly Val Val Asn Leu Val Ser
        195                 200                 205
Glu Gln Gly His Gln Val Ala Glu His Leu Val Thr Ser Asn Asp Val
    210                 215                 220
Asp Val Ile Ser Phe Thr Gly Ser Asn Ala Thr Gly Ala Arg Ile Met
225                 230                 235                 240
Ala Ala Ala Ala Pro Thr Met Lys Lys Leu Ser Leu Glu Leu Gly Gly
                245                 250                 255
Lys Ser Ala Cys Leu Val Phe Asp Asp Ala Asp Ile Ala Asp Val Ala
            260                 265                 270
Pro Lys Leu Ala Ala Ala Ala Thr Ile Ile Ala Gly Gln Gln Cys Thr
        275                 280                 285
Ala Ala Arg Arg Val Leu Val His Ala Ser Arg Tyr Asp Glu Met Lys
    290                 295                 300
Ala Ala Leu Lys Ala Ala Leu Ala Asn Ile Arg Ile Ala Pro Gly Ser
305                 310                 315                 320
Ala Ala Gly Ala Glu Met Gly Pro Leu Ile Asp Ala Ala Ser Leu Ala
                325                 330                 335
Ala Val Ala Lys Arg Ala Asp Glu Met Gln Ala Ala Asp Glu Val
            340                 345                 350
Val Leu Arg Gly Gly Arg Pro Ala Gly Asp Leu Ala Asn Gly Tyr Phe
        355                 360                 365
Leu Ser Pro Thr Leu Val Ala His Arg Asp Thr Ser Ala Phe Phe Val
    370                 375                 380
Gln Glu Glu Ile Phe Gly Pro Leu Val Val Leu Glu Lys Phe Glu Asp
385                 390                 395                 400
Glu Lys Glu Ala Val Ala Arg Ala Asn His Ser Asp Tyr Gly Leu Ser
                405                 410                 415
Ala Ser Val Trp Thr His Asp Gly Ala Arg Ala Met Arg Val Ala Arg
            420                 425                 430
```

Ala Leu Arg Asn Gly Thr Val Trp Ile Asn Asp His Asn Lys Leu Phe
        435                 440                 445

Ala Glu Ala Glu Thr Gly Gly Tyr Arg Arg Ser Gly Leu Gly Arg Leu
    450                 455                 460

His Gly Tyr Asp Ala Leu Ile Asp Phe Leu Glu Ile Lys His Val Tyr
465                 470                 475                 480

Gln Ser Cys Gly Val Val
                485

<210> SEQ ID NO 30
<211> LENGTH: 485
<212> TYPE: PRT
<213> ORGANISM: Dinoroseobacter shibae DFL 12

<400> SEQUENCE: 30

Met Thr Thr Thr Asp Leu Ile Ala Arg His Met Ile Gly Gly Ser Tyr
1               5                   10                  15

Ser Asp Ala Gly Asp Lys Ile Ala Ser Ile Asn Pro Ala Thr Gly Ala
            20                  25                  30

Val Val Gly His Val Arg Ala Asp Gly Ala Gln Ala Thr Ala Ala
        35                  40                  45

Ile Ala Ala Ala Arg Ala Ala Phe Asp Thr Thr Leu Trp Pro Gln Ser
50                  55                  60

Pro Arg Asp Arg Gln Met Ala Leu Leu Arg Trp Ala Asp Ala Leu Glu
65                  70                  75                  80

Ala Asp Leu Ala Arg Leu Ala Glu Leu Leu Thr Leu Thr Asn Gly Lys
                85                  90                  95

Pro Leu Gly Ala Ser Lys Gly Glu Leu Gly Ala Ala Ile Ser Glu Ile
            100                 105                 110

Arg Tyr Tyr Ala Gly Leu Thr Arg His Asn Pro Gly His Ala Met Glu
        115                 120                 125

Val Ala Pro Gly Glu Leu Ser Val Met Leu Arg Glu Pro Ala Gly Val
    130                 135                 140

Ala Gly Ile Ile Val Pro Trp Asn Ala Pro Ala Val Leu Leu Ile Arg
145                 150                 155                 160

Ser Leu Ala Pro Ala Leu Ala Val Gly Cys Thr Thr Val Thr Lys Pro
                165                 170                 175

Ala Pro Gln Thr Ala Leu Phe Thr Ala Ala Cys Met Ala Pro Leu Phe
            180                 185                 190

Glu Asp Ala Ala Ile Pro Ala Gly Val Val Asn Val Val Phe Glu Val
        195                 200                 205

Gly His Asp Ala Ala Gln Thr Leu Val Thr Ser Pro Asp Val Asp Val
    210                 215                 220

Ile Ser Phe Thr Gly Ser Asn Ala Val Gly Gln Arg Ile Met Ala Asp
225                 230                 235                 240

Ala Ala Pro Thr Met Lys Lys Leu Ser Leu Glu Leu Gly Gly Lys Ser
                245                 250                 255

Cys Cys Ile Val Leu Asp Asp Ala Asp Ile Gly Val Val Ala Pro Lys
            260                 265                 270

Leu Ala Ala Ala Ala Thr Ile Ile Ser Gly Gln Gln Cys Thr Ala Ala
        275                 280                 285

Arg Arg Val Leu Val His Glu Ser Arg Leu Asp Glu Ala Lys Ser Ala
    290                 295                 300

Leu Ser Ala Ala Leu Gln Ala Val Ser Ile Gly Asp Gly Met Ser Asp

```
            305                 310                 315                 320
Gly Thr Ala Met Gly Pro Leu Ile Asp Ile Gln Ser Arg Asp Arg Val
                    325                 330                 335

Met Arg Asp Cys Gly Thr Val Tyr Asp Thr Ala Asp Glu Val Val Leu
                    340                 345                 350

Arg Gly Gly Pro Leu Asp Gly Pro Lys Gly Ser Ala Phe Met Ser Pro
                    355                 360                 365

Ala Leu Val Val His Ser Asp Pro Asn Ala Ser Phe Val Gln Asp Glu
                    370                 375                 380

Ile Phe Gly Pro Leu Val Val Leu Glu Thr Phe Arg Asp Glu Ala Asp
385                 390                 395                 400

Ala Val Ala Lys Ala Asn Asn Thr Val Tyr Gly Leu Ser Ala Ser Ile
                    405                 410                 415

Trp Thr His Arg Gly Asp Ala Ser Trp Arg Leu Ala Arg Ala Leu Arg
                    420                 425                 430

Asn Gly Thr Val Trp Ile Asn Asp His Asn Arg Leu Phe Ala Glu Ala
                    435                 440                 445

Glu Thr Gly Gly Tyr Arg Arg Ser Gly Leu Gly Arg Leu His Gly Phe
                    450                 455                 460

Asp Gly Leu Leu Asp Phe Cys Glu Leu Lys His Val Tyr Gln Asn Val
465                 470                 475                 480

Gly Val Val Gly His
                    485

<210> SEQ ID NO 31
<211> LENGTH: 447
<212> TYPE: PRT
<213> ORGANISM: Cupriavidus basilensis

<400> SEQUENCE: 31

Met Glu Ala Val Ala Lys Lys Arg Thr Glu Thr Ile Ser Glu Ala Leu
1               5                   10                  15

Pro Ala Ala Thr Asn Arg Gln Val Phe Gly Ala Val Thr Ala Ser Cys
                20                  25                  30

Met Gly Trp Ala Leu Asp Leu Phe Asp Leu Phe Ile Leu Leu Phe Val
            35                  40                  45

Ala Pro Val Ile Gly Arg Leu Phe Phe Pro Ser Glu His Ala Met Leu
        50                  55                  60

Ser Leu Ala Ala Val Tyr Ala Ser Phe Ala Val Thr Leu Leu Met Arg
65                  70                  75                  80

Pro Leu Gly Ser Ala Ile Phe Gly Thr Tyr Ala Asp Arg His Gly Arg
                85                  90                  95

Lys Gly Ala Met Val Val Ala Val Thr Gly Val Gly Leu Ser Thr Ala
                100                 105                 110

Ala Phe Gly Leu Leu Pro Thr Val Gly Gln Val Gly Leu Leu Ala Pro
            115                 120                 125

Ala Leu Phe Ile Leu Leu Arg Leu Val Gln Gly Ile Phe Val Gly Gly
        130                 135                 140

Val Val Ala Ser Thr His Thr Ile Gly Thr Glu Ser Val Pro Pro Ser
145                 150                 155                 160

Trp Arg Gly Ala Val Ser Gly Leu Val Gly Gly Gly Ala Gly Ile
                165                 170                 175

Gly Ala Leu Leu Ala Ser Ile Thr Tyr Met Ala Met Thr Ala Leu Phe
            180                 185                 190
```

```
Pro Gly Glu Ala Phe Asp Ala Trp Gly Trp Arg Cys Met Phe Phe Ser
            195                 200                 205

Gly Ile Ile Ser Ser Val Leu Gly Leu Phe Ile Phe Asn Ser Leu Glu
210                 215                 220

Glu Ser Pro Leu Trp Lys Gln Leu Gln Ala Ala Lys Gly His Ala Ala
225                 230                 235                 240

Pro Val Glu Asn Pro Leu Arg Val Ile Phe Ser Arg Gln Tyr Arg Gly
            245                 250                 255

Val Leu Phe Val Asn Ile Leu Leu Thr Val Gly Gly Ser Ala Tyr
            260                 265                 270

Tyr Leu Thr Ser Gly Tyr Leu Pro Thr Phe Leu Lys Val Val Lys
            275                 280                 285

Ala Pro Ala Gly Ala Ser Ala Ala Ile Leu Met Ala Ser Ser Val Gly
            290                 295                 300

Val Ile Val Ala Ser Ile Ile Ala Gly His Leu Ser Thr Leu Ile Gly
305                 310                 315                 320

Arg Lys Arg Ala Phe Leu Leu Ile Gly Ala Leu Asn Val Val Leu Leu
                325                 330                 335

Pro Leu Ile Tyr Gln Arg Met Pro Ala Ala Pro Asp Val Thr Thr Leu
            340                 345                 350

Gly Ile Tyr Ala Val Ala Leu Ala Met Leu Gly Ser Thr Gly Phe Ala
            355                 360                 365

Pro Ile Leu Ile Phe Leu Asn Glu Arg Phe Pro Thr Ser Ile Arg Ala
            370                 375                 380

Thr Gly Thr Gly Leu Ser Trp Asn Ile Gly Phe Ala Ile Gly Gly Met
385                 390                 395                 400

Met Pro Thr Phe Ala Ser Leu Cys Ala Ser Thr Pro Ala Asp Leu Pro
                405                 410                 415

Lys Val Leu Gly Ile Phe Val Ala Val Val Thr Ala Ile Tyr Leu Ala
            420                 425                 430

Gly Ala Ala Ile Val Pro Glu Thr Ala Gly Arg Leu Gly Glu Lys
            435                 440                 445

<210> SEQ ID NO 32
<211> LENGTH: 449
<212> TYPE: PRT
<213> ORGANISM: Cupriavidus basilensis

<400> SEQUENCE: 32

Met Glu Ala Val Ala Lys Lys Ser Ala Ala Thr Ile Ser Glu Ala Leu
1               5                   10                  15

Pro Ala Ala Ser Asn Arg Gln Val Phe Gly Ala Val Ala Ala Ser Cys
            20                  25                  30

Met Gly Trp Ala Leu Asp Leu Asp Leu Phe Ile Leu Leu Phe Val
        35                  40                  45

Ala Pro Val Ile Gly Arg Leu Phe Phe Pro Ser Glu His Ala Met Leu
    50                  55                  60

Ser Leu Ala Ala Val Tyr Ala Ser Phe Ala Val Thr Leu Leu Met Arg
65                  70                  75                  80

Pro Leu Gly Ser Ala Ile Phe Gly Ser Tyr Ala Asp Arg His Gly Arg
                85                  90                  95

Lys Gly Ala Met Val Val Ala Val Thr Gly Val Gly Leu Ser Thr Ala
            100                 105                 110

Ala Phe Gly Leu Leu Pro Thr Val Gly Gln Val Gly Leu Leu Ala Pro
            115                 120                 125
```

Ala Leu Phe Ile Leu Leu Arg Leu Val Gln Gly Ile Phe Val Gly Gly
130                 135                 140

Val Val Ala Ser Thr His Thr Ile Gly Thr Glu Ser Val Pro Pro Ser
145                 150                 155                 160

Trp Arg Gly Ala Val Ser Gly Leu Val Gly Gly Gly Ala Gly Leu
                165                 170                 175

Gly Ala Leu Leu Ala Ser Ile Thr Tyr Met Ala Met Thr Ala Leu Phe
                180                 185                 190

Pro Gly Glu Ala Phe Asp Ala Trp Gly Trp Arg Cys Met Phe Phe Ser
                195                 200                 205

Gly Ile Ile Ser Ser Val Leu Gly Leu Phe Ile Phe Asn Ser Leu Glu
210                 215                 220

Glu Ser Pro Leu Trp Lys Gln Leu Gln Ala Ala Lys Gly His Ala Ala
225                 230                 235                 240

Pro Val Glu Asn Pro Leu Arg Val Ile Phe Ser Arg Gln Tyr Arg Gly
                245                 250                 255

Val Leu Phe Val Asn Ile Leu Leu Thr Val Gly Gly Ser Ala Tyr
                260                 265                 270

Tyr Leu Thr Ser Gly Tyr Leu Pro Thr Phe Leu Lys Val Val Lys
                275                 280                 285

Ala Ser Ala Gly Glu Ser Ala Ala Ile Leu Met Ala Ser Ser Leu Gly
290                 295                 300

Val Ile Val Ala Ser Ile Leu Ala Gly His Leu Ser Thr Met Ile Gly
305                 310                 315                 320

Arg Lys Arg Ala Phe Leu Leu Ile Gly Ala Leu Asn Val Val Val Leu
                325                 330                 335

Pro Leu Leu Tyr Gln Trp Met Pro Ala Ala Pro Asp Thr Thr Thr Leu
                340                 345                 350

Gly Leu Tyr Ala Val Val Leu Ser Met Leu Gly Cys Ser Gly Phe Ala
                355                 360                 365

Pro Ile Leu Ile Phe Leu Asn Glu Arg Phe Pro Thr Ser Ile Arg Ala
370                 375                 380

Thr Gly Thr Gly Leu Ser Trp Asn Ile Gly Phe Ala Val Gly Gly Met
385                 390                 395                 400

Met Pro Thr Phe Ala Ser Leu Cys Ala Ser Thr Pro Ala Glu Leu Pro
                405                 410                 415

Met Val Leu Gly Ile Phe Leu Ala Val Val Thr Ile Ile Tyr Leu Val
                420                 425                 430

Gly Ala Phe Ile Val Pro Glu Thr Val Gly Arg Leu Gly Asp Asn Gly
                435                 440                 445

Ala

<210> SEQ ID NO 33
<211> LENGTH: 449
<212> TYPE: PRT
<213> ORGANISM: Methylobacterium radiotolerans

<400> SEQUENCE: 33

Met Gln Thr Ala Ala Thr Phe Ser Asp Pro Pro Ala Leu Ala Lys
1               5                   10                  15

Pro Thr Gly Arg Gln Thr Val Thr Ala Ala Met Ala Ser Leu Phe Gly
                20                  25                  30

Trp Gly Leu Asp Leu Phe Asp Leu Phe Ile Leu Leu Tyr Val Ala Pro
                35                  40                  45

```
Val Val Gly Thr Leu Phe Phe Pro Ala Asp Lys Pro Met Leu Ser Leu
 50                  55                  60

Ala Gly Ala Tyr Ala Ser Phe Ala Val Thr Leu Leu Ile Arg Pro Leu
 65                  70                  75                  80

Gly Ser Ala Leu Phe Gly Ser Tyr Ala Asp Arg Phe Gly Arg Arg Arg
                 85                  90                  95

Ala Leu Met Val Ala Val Val Gly Val Gly Ile Ser Thr Ala Val Phe
            100                 105                 110

Gly Leu Leu Pro Thr Val Gly Gln Ile Gly Trp Leu Ala Thr Ala Val
        115                 120                 125

Phe Leu Phe Phe Arg Leu Val Gln Gly Ile Phe Val Gly Gly Val Val
    130                 135                 140

Ala Ala Ser His Thr Ile Gly Thr Glu Ser Val Pro Glu Arg Trp Arg
145                 150                 155                 160

Gly Leu Met Ser Gly Ala Val Gly Gly Gly Ser Ala Ile Gly Gly
                165                 170                 175

Leu Leu Ala Ser Leu Val Phe Tyr Val Val Ser Leu Met Ala Pro Gly
                180                 185                 190

Glu Ala Phe Ala Glu Trp Gly Trp Arg Leu Met Phe Phe Ser Gly Leu
                195                 200                 205

Leu Thr Ser Val Ile Gly Leu Ile Leu Phe Arg Asn Leu Glu Glu Ser
    210                 215                 220

Pro Ile Phe Lys Glu Leu Gln Ala Arg Lys Ala Ala Leu Arg Ala Gly
225                 230                 235                 240

Ala Pro Ala Glu Ala Ser Pro Ile Arg Ser Leu Phe Ser Pro Ser Asn
                245                 250                 255

Arg Gly Ser Phe Ala Val Ala Thr Leu Ile Ser Phe Gly Gly Gly Ala
                260                 265                 270

Ala Tyr Tyr Leu Thr Ser Gly Tyr Leu Pro Thr Leu Leu Lys Leu Val
                275                 280                 285

Asn Gly Val Pro Asn Ala Thr Ala Ser Met Ile Leu Ile Gly Ala Asn
    290                 295                 300

Val Ala Ala Ala Ile Gly Ala Cys Gly Met Gly Glu Leu Ser Gln His
305                 310                 315                 320

Ile Gly Arg Lys Arg Ser Phe Leu Leu Met Gly Val Ile Arg Leu Leu
                325                 330                 335

Ala Phe Pro Ala Leu Phe Leu Thr Met Ala Asn Thr Thr Ser Leu Val
                340                 345                 350

Gly Val Ala Ala Cys Ala Phe Leu Leu Ala Leu Ile Ala Asn Gly Ser
                355                 360                 365

Tyr Gly Pro Leu Leu Ile Phe Leu Asn Glu Lys Phe Pro Thr Ala Val
    370                 375                 380

Arg Ala Thr Gly Thr Gly Leu Thr Trp Asn Ile Gly Phe Ala Leu Gly
385                 390                 395                 400

Gly Met Leu Pro Thr Leu Val Ser Leu Val Ala Asp Gly Pro Thr Gln
                405                 410                 415

Ile Pro Met Val Leu Ala Val Ile Thr Thr Gly Val Thr Leu Val Tyr
                420                 425                 430

Leu Val Gly Ala Phe Leu Thr Asp Glu Thr Gln Gly Asn Leu Asp Arg
        435                 440                 445

Ala
```

```
<210> SEQ ID NO 34
<211> LENGTH: 443
<212> TYPE: PRT
<213> ORGANISM: Sulfolobus acidocaldarius

<400> SEQUENCE: 34
```

| | | | | | | | | | | | | | | |
|---|---|---|---|---|---|---|---|---|---|---|---|---|---|---|
| Met | Lys | Lys | Glu | Glu | Lys | Phe | Thr | Ser | Asn | His | Phe | Lys | Trp | Thr | Leu |
| 1 | | | | 5 | | | | | 10 | | | | | 15 | |

Ala Thr Phe Phe Thr Trp Thr Phe Asp Leu Tyr Asp Leu Phe Thr Ile
                    20                  25                  30

Leu Leu Val Ala Pro Tyr Ile Ser Ser Leu Phe Phe Pro Ser Ser Ile
                35                  40                  45

Thr Phe Leu Ser Ile Ala Ala Thr Tyr Ala Gly Phe Ala Thr Ser Leu
    50                  55                  60

Ile Met Arg Pro Val Gly Ala Thr Val Phe Gly Ser Arg Val Ser Asp
65                  70                  75                  80

Lys Val Gly Arg Lys Arg Ala Ile Phe Tyr Gly Leu Ile Gly Leu Val
                85                  90                  95

Ile Thr Ser Thr Leu Gln Gly Ala Leu Pro Thr Tyr Gln Val Val Gly
                100                 105                 110

Val Ile Ala Pro Ile Leu Leu Ala Val Arg Leu Ile Gln Gly Val
                115                 120                 125

Phe Ile Gly Gly Ile Thr Ala Gly Ser His Val Ile Gly Pro Glu Ser
    130                 135                 140

Val Pro Glu Arg Tyr Arg Gly Ile Val Gly Gly Leu Gly Phe Ser Ala
145                 150                 155                 160

Ala Gly Val Ala Tyr Leu Ile Ala Ala Gly Trp Phe Phe Leu Thr Thr
                165                 170                 175

Ile Leu Tyr Pro Gly Ser Ser Tyr Leu Val Trp Gly Trp Arg Val Met
                180                 185                 190

Phe Phe Gly Gly Leu Leu Ser Leu Ala Val Leu Gly Phe Val Asn Tyr
    195                 200                 205

Leu Val Pro Glu Ser Glu Val Trp Thr Lys Ile Lys Lys Arg Gly Ser
210                 215                 220

Val Val Lys Ser Pro Leu Lys Glu Ile Phe Ser Lys Tyr Arg Tyr Gln
225                 230                 235                 240

Leu Gly Val Ala Leu Leu Leu Ser Ile Gly Trp Gly Ala Ser Phe Tyr
                245                 250                 255

Val Thr Asp Gly Ile Leu Pro Thr Phe Leu Ser Ser Val Asn Lys Leu
                260                 265                 270

Ala Lys Thr Glu Ile Ala Ile Val Met Ile Ile Gly Ser Ile Gly Met
                275                 280                 285

Ser Ile Gly Pro Leu Ile Gly Gly Glu Ile Ser Gln Ile Ile Gly Arg
    290                 295                 300

Lys Ile Thr Ser Leu Ile Gly Ala Ile Val Leu Ala Val Val Gly
305                 310                 315                 320

Pro Leu Phe Leu Ser Leu Gly Ser Leu Lys Ser Gly Asp Leu Asn Gln
                325                 330                 335

Ile Ile Leu His Ser Phe Ala Ile Leu Phe Leu Val Asp Ile Gly Gly
                340                 345                 350

Gly Met Leu Met Thr Tyr Leu Asn Glu Ile Tyr Pro Ala Ser Val Arg
    355                 360                 365

Gly Thr Gly Val Gly Phe Thr Trp Asn Thr Gly Phe Ala Ile Gly Gly
    370                 375                 380

Thr Ile Pro Thr Ile Ile Ser Leu Ala Val Ala Ser Ala Gly Leu Ser
385                 390                 395                 400

Ala Phe Pro Ser Ile Met Phe Tyr Thr Leu Ile Val Val Ser Val Ile
                405                 410                 415

Ile Leu Val Gly Thr Val Leu Thr Lys Glu Thr Lys Gly Thr Ile Ser
            420                 425                 430

Lys Glu Glu Tyr Glu Ile Gln Lys Glu Thr Leu
        435                 440

<210> SEQ ID NO 35
<211> LENGTH: 1240
<212> TYPE: DNA
<213> ORGANISM: Artificial
<220> FEATURE:
<223> OTHER INFORMATION: Synthetic KpnI-NheI fragment for expression of
      alcohol dehydrogenase of Aneurinibacillus terranovensis

<400> SEQUENCE: 35

| | |
|---|---|
| ggtaccgaat tccacatgac aaggggagac cgcatgacca ttagtccggc agttaaagcc | 60 |
| atcaactttg aattttcatt taacctgccg accctgatcg aatttggtta tggtaaaatg | 120 |
| gaaaaattcg gccagcagct gattagcatt ggtgttaaac gcatttttat ggtgaccgat | 180 |
| aaaggtgttg aaagcgcagg tctgctggca gcactgaccg attcactgca ggcagcagca | 240 |
| attcagtttg atatctatac cgatgtggaa agcgatccga gcctggaaac cattgatcgt | 300 |
| ggtgttgaag ttttttcagca gaaaccgtat gattgcattg ttgcagttgg tggtggtagc | 360 |
| ccgattgata ccgcaaaagg tattcgtgtt gttgcagcaa atggtggtaa tattggtcat | 420 |
| tatgccggtg ttaatcagat tccggttgca ccgaccattc cgctgctggc aattccgacc | 480 |
| accagtggca ccggtagcga agttaccaat tttggtgttt atagcgattg cagaacaac | 540 |
| gttaaagtta ccgttaccag ccagtatatg gcaccgacaa ttgcatgggt tgatccggca | 600 |
| ctgaccatga gcctgcctgc aaaaatgacc gcagcaagcg gtattgatgc actggcacat | 660 |
| ggtattgaaa cctttttag cctgggtagc agtccggcaa gtgatgccct ggcaattgaa | 720 |
| gcaattcata ccgttaatcg ttatctgagc cgtgcagttc ataatggtag cgatatggaa | 780 |
| gcacgtattg gtatgagcca tggtagcctg ctggctggca tggcatttaa caatggtttt | 840 |
| ctgggtctgg cccatgccat tggtagcgca ctgagcggtc attgtcatgt tccgcatggt | 900 |
| gttgcaattg gtctgctgct gccgaaagtt gttgaattta tgcaaccgt tcgtccggat | 960 |
| aaagcagcaa aaattgcagg tctgatgggt atgaaaggtg aacatagcga agaactggcc | 1020 |
| ctgcaggcat caccggcagt tgcacgtctg gttgaagata ttggcctgcc gacacgtctg | 1080 |
| cgtgaagttg atgttaccga aaaaaaactg ttcgagatcg ccaaagatag ctttaaaagc | 1140 |
| ggcatgatga aattcaatcc gcgtcagccg agcgaaagcg aagttctgca gctgctgaaa | 1200 |
| gaaatctttt gaagaccgaa gcgaattcct cgagtctaga | 1240 |

<210> SEQ ID NO 36
<211> LENGTH: 1205
<212> TYPE: DNA
<213> ORGANISM: Artificial
<220> FEATURE:
<223> OTHER INFORMATION: Synthetic KpnI-NheI fragment for expression of
      alcohol dehydrogenase of Brevibacillus thermoruber

<400> SEQUENCE: 36

| | |
|---|---|
| ggtacctagg aaaggaagat taacccatga gccagaccgt gcagggcacc gacttcgcct | 60 |
| tcagcttcca cctgccgacc ctgatcgagt tcggctacgg ccgcgccagc cgcctgggcg | 120 |

```
agcgcctgca gcacctgggc gtgaccaacg tgttcgtggt gaccgacaag ggcgtggagg      180
ccgccggcct gctgaacggc ctggtgggca gcctgcagag cgccggcatc gccttcgacc      240
tgtacaccga ggtggagccg acccgggcc tggagaccat cgaccgcggc gccgccgtgt      300
tccgcgccaa gccgtacgac tgcctggtgg ccgtgggcgg cggcagcccg atcgacgccg      360
ccaagggcat gcgcgtggtg accagctgcg gcggcagcat cgccgactac gccggcgtga      420
accgcgtgcc gatggccccg gccgtgccgc tggtggccgt gccgaccacc agcggcaccg      480
gcagcgaggt gaccatgttc ggcgtgtaca gcgactggca caaccacgtg aaggtgaccg      540
tgaccagccc gcacatggcc ccgaccatcg ccctggtgga cccggccctg accgtgagcc      600
tgccggccaa gatgaccgcc gccagcggca tcgacgccct ggcccacggc atcgagacct      660
tcttcagcgt gcgcagccgc ccggccagcg acgccctggc catggaggcc atcgccgccg      720
tgaacgccca cctgcgccgc gccgtgcacg acggcagcga cgtggaggcc cgcatcggca      780
tgagccacgg cagcctgctg gccggcatgg ccttcaccaa cggcttcctg ggcctggccc      840
acgccatcgg cagcgccctg agcggccact gccacgtgcc gcacggcatc gccatcggcc      900
tgctgctgcc gcacgtggtg gccttcaacg ccccggcccg cccggacaag gccgcccagc      960
tggcccgcct gctgggcgtg gaggccaacc gcgcgagga gcgcggcgag gagaccagcg     1020
ccgccgtggc ccgcatggtg gccgacatcg gcctgccgac ccgcctgcgc gacgtgggcg     1080
tgccggagga gaagctgccg gccatcgcca aggacgcctt caagagcggc atgatgacct     1140
gcaacccgcg ccagccgacc gagcaggagg tgcgcgagct gctgcgccgc gccttctgag     1200
ctagc                                                                 1205
```

<210> SEQ ID NO 37
<211> LENGTH: 1228
<212> TYPE: DNA
<213> ORGANISM: Artificial
<220> FEATURE:
<223> OTHER INFORMATION: Synthetic KpnI-NheI fragment for expression of
    alcohol dehydrogenase of Brevibacillus panacihumi

<400> SEQUENCE: 37

```
ggtaccgaat tccacatgac aagggagac cgcatgagcg caaatcagag cgttcagggt       60
attgaaagcc cgtttagctt tcatctgccg accaatgttc agtttggtgt tggtagcgca      120
agccgtctgg gtgaaatgct gctgagcatg ggtgttcgtc gtgttttct ggttaccgat       180 cagggtgtgc gtcaggcagg tctgctggat gaagttattc atagcctgga agaaaaaggc      240
ctgcactttc agatttatgc agatgttgaa ccggatccga gcctggaaac cattcaggca      300
ggcgcagcaa tgtttcagca gcagagcttt gattgtatgg ttgcaattgg tggtggtagt      360
ccgattgata ccgcaaaagg tattcgtgtt ctggcagcaa atggtggcgg tattggtcag      420
tatgccggtg ttaatcgcgt tccggcagca agcgcaattc cgctgattgc aattccgacc      480
accagtggca ccggtagcga agttaccatt tttggtgttt atagcgattg ggagaaccac      540
gtgaaaatta ccgttaccag tccgcatatg gcaccgagca ccgcactgat tgatccggca      600 ctgacctga gctgcctgc aaaaatgacc gcagcaaccg tattgatgc actggcacat        660 ggcattgaaa cctttttag cctgcgtagc agtccggcaa gtgatgccct ggcaattcat      720
gcaatgaaaa tgattgcacc gcatctgcgt cgtgcagttc gtgatggtgc agatatggaa      780
gcacgtattg gtatgagcca gggtagcgtg ctggcaggta tggcatttaa caatggtttt      840
ctgggtctgg cccatgccat tggtagtgca ctgagcggtc attgtcatgt tccgcatggt      900
```

```
gttgcgattg gcctgctgct gccgcatgtg gttgcattta atacaccggt tcgtccggaa      960
aaagcagaac tgattgccga tgttctgggt agcgttcaga agaaaccgg caccgcagcc      1020 gaactggttg tcagctggt tcaggatatt ggtctgccgc agcgtctgca agaagttggc      1080
gttccggaag cgaaactggt tgatattgca aaagatagc ttaaaagcgg catgatgaaa      1140
tggaatccgc gtctgccgac agaacaagaa gttctggaac tgctgcagaa agccttttga    1200
agaccgaagc gaattcctcg agtctaga                                       1228
```

<210> SEQ ID NO 38
<211> LENGTH: 1184
<212> TYPE: DNA
<213> ORGANISM: Artificial
<220> FEATURE:
<223> OTHER INFORMATION: Synthetic KpnI-NheI fragment for expression of alcohol dehydrogenase of Bacillus sp. FJAT-14578

<400> SEQUENCE: 38

```
ggtacctagg aaaggaagat taacccatgt acccgagctt cgagttccac ctgccgacca     60
agatccactt cggctacaac accatcaagc agctggacca cctgccgttc gagatcaagc    120
gcgccttcat cgtgaccgac cagggcgtgc tgaacagcgg cctggtggag aacgtgacca    180
acatcctgaa ggaccaccag atcagctacg tgatctacag cgaggtggag ccggacccga    240
gcgtggagac cgtggacaag gccgcccaga tgttccagcg cgaggaggcc gacgccctga    300
tcgccatcgg cggcggcagc ccgatcgaca ccgccaaggg cgtgcgcgtg atcgccggca    360
acggcggcag catccgcgac tacgccgcg tgaacctgat caagcagaag agcaacatcc    420
cgctgatcgc catcccgacc accagcggca ccggcagcga ggtgaccatc ttcgccgtgt    480
tcagcgactg ggaggagaac cgcaaggtga ccgtgaccag cccgttcctg gccccggaca    540
tcagcatcgt ggacccgaag atgaccatga ccgccccgcc ggccatcacc gccgccagcg    600
gcttcgacgc cttcgcccac ggcgccgaga ccttcgtgag ccgcgccagc cagcggcca    660 gcgacgtgct ggccttcagc gccatgagca ccgtgagcaa gtacctgcgc gcgccgtgt    720 acaacggcga ggacgtggag gcccgcatca agatggccga ggccagcctg ctggccggca    780
tggccttcaa ccagagctac ctgggcctga cccacgccat cggcagcgcc ctgagcggcc    840
acgcccacgt gagccacggc gtggccatcg gcctgctgct gccgggcgtg atccgctaca    900
acagcatcag ccgcatggac aagcacatcg agatggccgg cgccttccgc gagatcgacc    960
gcagcctgag cgactgggag atcatcgacc agctgatcga ggacgtgagc cgcctgcgcg   1020
acgacatcgg cctgccgcag cgcctgcagc aggtgggcgt gaaggaggac cagctgaaga   1080
tgatcgccgc cgacagcgtg aagagcggca tgtggaagtt caacccgcgc caggccagcg   1140
aggaggagat cctggagctg ctgaaggagc tgtactgagc tagc                    1184
```

<210> SEQ ID NO 39
<211> LENGTH: 1184
<212> TYPE: DNA
<213> ORGANISM: Artificial
<220> FEATURE:
<223> OTHER INFORMATION: Synthetic KpnI-NheI fragment for expression of alcohol dehydrogenase of Bacillus sp. L1(2012)

<400> SEQUENCE: 39

```
ggtacctagg aaaggaagat taacccatgt acaccagctt caacttccac ctgccgaccc     60
gcatccagtt cggctacgag aaggtgaagg agctgaagaa cctgccgttc caggccaacc    120
```

```
gcgccttcat cgtgaccgac aagggcgtgg agaaggccgg cctgctgaac gacgtgatcg      180
acgccatcaa gcaggccaac atgacctaca agatctaccg cgacgtggag ccggacccga      240
gcgtggagac cgtggacaag gccgccaagg ccttcgccga ggccgagtgc gacctgctga      300
tcgccgtggg cggcggcagc ccgatcgaca ccgccaaggg cgtgcgcgtg gtggccagca      360
acggcggcag catccgcaac tacagcggcg tgaacctggt gaaggaggcc ccgagcgtgc      420
cgctggtggc catcccgacc accgccggca ccggcagcga ggtgaccatc ttcgccgtgt      480
tcagcgacga caaggagaac cgcaaggtga ccgtgaccag cagccacctg agcccggacg      540
tgagcatcat cgaccgaag ctgaccctga ccgccccgcc gagcatcacc gccgccgccg      600
gcttcgacgc cttcgcccac gccgccgagg ccttcgtgag ccgcatcagc cagccgccga      660
gcgacgccct ggccctgagc gccatgaaga ccgtgcacac ctacctgcgc cgcgccgtgt      720
acaacggcga cgacatcgag gcccgcatga agatggccga ggccagcctg ctggccggca      780
tggccttcaa ccagagctac ctgggcctgg cccacgccat cggcagcgcc atcagcgtgc      840
acgcccacgt gagccacggc gtggtgatcg gcctgctgct gccgaaggtg atcgagtaca      900
acctggtggc caagatcgac aagtacgccg aggccggcaa gtacatcgag cagagcagcc      960
acggcctgag caactacgag gccgccgccc tgttcagcga gaccgtgacc cagctgcgca    1020
acgacatcgg cctgccgaag cagctgcgcg aggtgaacgt gaaggaggcc cagctggagg    1080
ccatcagcaa ggacagcatc aagagcggca tgtggcagtt caacccgcgc cgcgccagcg    1140
agcaggacgt gtaccagatg ctgcgcgaga tgctgtgagc tagc                     1184

<210> SEQ ID NO 40
<211> LENGTH: 27
<212> TYPE: DNA
<213> ORGANISM: Artificial
<220> FEATURE:
<223> OTHER INFORMATION: ribosome binding site containing spacer no. 2

<400> SEQUENCE: 40
gaattccaca tgacaagggg agaccgc                                          27
```